(12) United States Patent
Fabiilli et al.

(10) Patent No.: US 10,709,812 B2
(45) Date of Patent: Jul. 14, 2020

(54) BIODEGRADABLE HYDROGEL FOR TISSUE EXPANSION

(71) Applicant: THE REGENTS OF THE UNIVERSITY OF MICHIGAN, Ann Arbor, MI (US)

(72) Inventors: Mario L. Fabiilli, Plymouth, MI (US); Alexander Moncion, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/751,671

(22) PCT Filed: Sep. 23, 2016

(86) PCT No.: PCT/US2016/053556
§ 371 (c)(1),
(2) Date: Feb. 9, 2018

(87) PCT Pub. No.: WO2017/058672
PCT Pub. Date: Apr. 6, 2017

(65) Prior Publication Data
US 2018/0243474 A1    Aug. 30, 2018

Related U.S. Application Data

(60) Provisional application No. 62/234,422, filed on Sep. 29, 2015.

(51) Int. Cl.
*A61L 27/36* (2006.01)
*A61K 9/107* (2006.01)
(Continued)

(52) U.S. Cl.
CPC .......... *A61L 27/362* (2013.01); *A61K 9/0024* (2013.01); *A61K 9/107* (2013.01);
(Continued)

(58) Field of Classification Search
CPC ........ A61L 27/362; A61L 27/16; A61L 27/18; A61L 2300/252; A61L 2300/258;
(Continued)

(56) References Cited

U.S. PATENT DOCUMENTS 3,687,808 A   8/1972   Merigan, Jr. et al.
4,845,205 A   7/1989   Huynh Dinh et al.
(Continued)

FOREIGN PATENT DOCUMENTS

EP   1072679 A2   1/2001
WO   WO-1997/012896 A1   4/1997

OTHER PUBLICATIONS

Ammi et al., "Ultrasonic Contrast Agent Shall Rupture Detected by Inertial Cavitation and Rebound Signals," Ieee Transactions on Ultrasonics Ferroelectrics and Frequency Control 53:126-36 (2006).
(Continued)

*Primary Examiner* — Trevor Love
(74) *Attorney, Agent, or Firm* — Marshall, Gerstein & Borun LLP

(57) ABSTRACT

The present invention is directed to compositions and methods for delivering a tissue scaffold comprising a perfluorocarbon emulsion to an individual in need of tissue expansion.

19 Claims, 18 Drawing Sheets

(51) Int. Cl.
  A61K 9/00    (2006.01)
  A61K 41/00   (2020.01)
  A61K 47/24   (2006.01)
  A61K 35/33   (2015.01)
  A61K 35/34   (2015.01)
  A61L 27/16   (2006.01)
  A61L 27/18   (2006.01)
  A61K 35/12   (2015.01)
(52) U.S. Cl.
  CPC .............. *A61K 35/33* (2013.01); *A61K 35/34* (2013.01); *A61K 41/0028* (2013.01); *A61K 47/24* (2013.01); *A61L 27/16* (2013.01); *A61L 27/18* (2013.01); *A61K 35/12* (2013.01); *A61L 2300/252* (2013.01); *A61L 2300/258* (2013.01)
(58) Field of Classification Search
  CPC .. A61K 9/107; A61K 9/0024; A61K 41/0028; A61K 47/24; A61K 35/33; A61K 35/34; A61K 35/12
  See application file for complete search history.

(56) References Cited

U.S. PATENT DOCUMENTS

| | | | |
|---|---|---|---|
| 5,130,302 | A | 7/1992 | Spielvogel et al. |
| 5,134,066 | A | 7/1992 | Rogers et al. |
| 5,175,273 | A | 12/1992 | Bischofberger et al. |
| 5,270,163 | A | 12/1993 | Gold et al. |
| 5,367,066 | A | 11/1994 | Urdea et al. |
| 5,432,272 | A | 7/1995 | Benner |
| 5,457,187 | A | 10/1995 | Gmeiner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,637,459 | A | 6/1997 | Burke et al. |
| 5,645,985 | A | 7/1997 | Froehler et al. |
| 5,681,941 | A | 10/1997 | Cook et al. |
| 5,750,692 | A | 5/1998 | Cook et al. |
| 5,763,588 | A | 6/1998 | Matteucci et al. |
| 5,830,653 | A | 11/1998 | Froehler et al. |
| 6,005,096 | A | 12/1999 | Matteucci et al. |
| 7,223,833 | B1 | 5/2007 | Nielsen et al. |
| 7,611,728 | B2 | 11/2009 | Kidane et al. |
| 7,667,004 | B2 | 2/2010 | Zhong et al. |
| 2009/0214649 | A1 | 8/2009 | Gazit et al. |
| 2010/0082019 | A1 | 4/2010 | Neev |
| 2010/0222802 | A1* | 9/2010 | Gillespie, Jr. ........... A61B 90/02 606/192 |
| 2013/0330389 | A1 | 12/2013 | Fabiilli et al. |

OTHER PUBLICATIONS

Apfel et al., "Gauging the Likelihood of Cavitation From Short-Pulse, Low-Duty Cycle Diagnostic Ultrasound," Ultrasound in Medicine and Biology 17(2):179-185 (1991).
Apfel, "Possibility of Microcavitation From Diagnostic Ultrasound," IEEE Transactions on Ultrasonics Ferroelectrics and Frequency Control 33:139-42 (1986).
Atchley et al., "Thresholds for Cavitation Produced in Water by Pulsed Ultrasound," Ultrasonics 26:280-285 (1988).
Barthes et al., "Cell Microenvironment Engineering and Monitoring for Tissue Engineering and Regenerative Medicine: The Recent Advances," Biomed Research International, 18 pages (2014).
Bos et al., "Growth factor expression in cartilage wound healing: temporal and spatial immunolocalization in a rabbit auricular cartilage wound model," Osteoarthritis and Cartilage 9:382-9 (2001).
Brennen, "Fission of collapsing cavitation bubbles," Journal of Fluid Mechanics 472:153-66 (2002).
Chen et al., "A comparison of the fragmentation thresholds and inertial cavitation doses of different ultrasound contrast agents," Journal of the Acoustical Society of America 113:643-51 (2003).
Chen et al., "The disappearance of ultrasound contrast bubbles: Observations of bubble dissolution and cavitation nucleation," Ultrasound Med Biol 28:793-803 (2002).
Chin et al., "Hydrogel-Perfluorocarbon Ccomposite Scaffold Promotes Oxygen Transport to Immobilized Cells," Biotechnology Progress, 24:358-366 (2008).
Concise Encyclopedia of Polymer Science and Engineering, "Polynucleotides," J. I. Kroschwitz Ed., John Wiley & Sons, pp. 858-859 (1990).
Cook, "Medicinal chemistry of antisense oligonucleotides—future opportunities," Anti-Cancer Drug Design 6:585-607 (1991).
Crawford et al., "Peptide aptamers: Tools for biology and drug discovery," Briefings in Functional Genomics and Proteomics 2(1): 72-79 (2003).
Dayton et al., "Optical and acoustical observations of the effects of ultrasound on contrast agents," IEEE Transactions on Ultrasonics Ferroelectrics and Frequency Control 46:220-32 (1999).
Dehghani et al., "Engineering porous scaffolds using gas-based techniques," Current Opinion in Biotechnology 22:661-666 (2011).
Dias et al., "Solubility of oxygen in liquid perfluorocarbons," Fluid Phase Equilibria 222:325-30 (2004).
Diaz-Lopez et al., "Liquid perfluorocarbons as contrast agents for ultrasonography and 19F-MRI," Pharmaceutical Research 27(1):1-16 (2010).
Engler et al., "Matrix Elasticity Directs Stem Cell Lineage Specification," Cell 126:677-689 (2006).
Englisch et al., "Chemically Modified Oligonucleotides as Probes and Inhibitors," Angewandte Chemie, International Edition, 30:613-722 (1991).
Epstein et al., "On the stability of gas bubbles in liquid-gas solutions," Journal of Chemical Physics 18:1505-9 (1950).
Epstein-Barash et al., "A microcomposite hydrogel for repeated on-demand ultrasound-triggered drug delivery," Biomaterials 31:5208-17 (2010).
Fabiilli et al., "Acoustic droplet-hydrogel composites for spatial and temporal control of growth factor delivery and scaffold stiffness," Acta Biomater. 97(7):7399-7409 (2013).
Fabiilli et al., "Delivery of water-soluble drugs using acoustically triggered perfluorocarbon double emulsions," Pharm Res. 27:2753-2765 (2010).
Fabiilli et al., "The Tole of Inertial Cavitation in Acoustic Droplet Vaporization," IEEE Trans Ultrason Ferroelectr Freq Control 56:1006-17 (2009).
Faithfull, "Oxygen Delivery From Fluorocarbon Emulsions—Aspects of Convective and Diffusive Transport," Biomaterials Artificial Cells and Immobilization Biotechnology 20:797-804 (1992).
Ferrara et al., "Ultrasound microbubble contrast agents: fundamentals and application to gene and drug delivery," Annual Review of Biomedical Engineering 9:425-47 (2007).
Flynn et al., "A Mechanism for the Generation of Cavitation Maxima by Pulsed Ultrasound," Journal of the Acoustical Society of America 76:505-12 (1984).
Fowlkes et al., "Cavitation Threshold Measurements for Microsecond Length Pulses of Ultrasound," Journal of the Acoustical Society of America 83:2190-201 (1988).
Freier et al., "The ups and downs of nucleic acid duplex stability: structure-stability studies on chemically-modified DNA:RNA duplexes," Nucleic Acids Research, 25:4429-4443 (1997).
Frimpong et al., "Synthesis and temperature response analysis of magnetic-hydrogel nanocomposites," Journal of Biomedical Materials Research Part A 80A:1-6 (2007).
Fujie et al., "Micropatterned Polymeric Nanosheets for Local Delivery of an Engineered Epithelial Monolayer.," Advanced Materials 26:1699-705 (2014).
Giesecke et al., "Ultrasound-Mediated Cavitation Thresholds of Liquid Perfluorocarbon Droplets in Vitro," Ultrasound in Medicine and Biology 29:1359-1365 (2003).

(56) References Cited

OTHER PUBLICATIONS

Hallow et al., "Measurement and correlation of acoustic cavitation with cellular bioeffects," Ultrasound in Medicine and Biology 32:1111-22 (2006).
Holland et al., "An improved theory for the prediction of microcavitation thresholds," IEEE Transactions on Ultrasonics, Ferroelectrics, and Frequency Control 36:204-8 (1989).
Huebsch et al. ,"Ultrasound-triggered disruption and self-healing of reversibly cross-linked hydrogels for drug delivery and enhanced chemotherapy," Proceedings of the National Academy of Sciences of the United States of America 111:9762-7 (2014).
Hwang et al., "Correlation between inertial cavitation dose and endothelial cell damage in vivo," Ultrasound in Medicine and Biology 32:1611-9 (2006).
Ibsen et al., "A Novel Nested Liposome Drug Delivery Vehicle Capable of Ultrasound Triggered Release of its Payload," Journal of Controlled Release 155(3):358-66 (2011).
International Search Report and Written Opinion from International Application No. PCT/US2016/053556 dated Dec. 8, 2016.
Javadi et al., "Ultrasonic gene and drug delivery using eLiposomes," Journal of Controlled Release 167:92-100 (2013).
Johnson et al., "In vitro comparison of dodecafluoropentane (DDFP), perfluorodecalin (PFD), and perfluoroctylbromide (PFOB) in the facilitation of oxygen exchange," Artificial cells, blood substitutes, and biotechnology 37:156-62 (2009).
Kandadai et al., "Comparison of surfactants used to prepare aqueous perfluoropentane emulsions for pharmaceutical applications," Langmuir 26:4655-60 (2010).
Katz, "The Reversible Reaction of Sodium Thymonucleate and Mercuric Chloride," J. Am. Chem. Soc., 74:2238-2245 (1952).
Kawabata et al., "Nanoparticles with Multiple Perfluorocarbons for Controllable Ultrasonically Induced Phase Shifting," Japanese Journal of Applied Physics 44:4548-52 (2005).
Kniazeva et al., "Effects of Extracellular Matrix Density and Mesenchymal Stem Cells on Neovascularization In Vivo," Tissue Engineering Part A 17:905-14 (2011).
Kobus et al., "Cleft palate repair with the use of osmotic expanders: a preliminary report," J. Plast. Reconstr. Aesthet. Surg. 60:414-421 (2007).
Kopylov et al., "Combinatorial Chemistry of Nucleic Acids; SELEX," Molecular Biology 34(6): 940-954 (2000) translated from Molekulyarnaya Biologiya, vol. 34, No. 6, 2000, pp. 1097-1113.
Kosturko et al., "The Crystal and Molecular Structure of a 2:1 Complex of 1-Methylthymine-Mercury (II)," Biochemistry 13:3949-3952 (1974).
Kripfgans et al., "Acoustic droplet vaporization for therapeutic and diagnostic applications," Ultrasound in Medicine and Biology 26:1177-89 (2000).
Kripfgans et al., "In Vivo Droplet Vaporization for Occlusion Therapy and PHase Aberration Correction," IEEE Trans Ultrason Ferroelectr Freq Control, 49(2):726-738 (2002).
Kripfgans et al., "On the acoustic vaporization of micrometer-sized droplets," J Acoust Soc Am 116:272-81 (2004).
Kulkarni et al., "Electrically responsive smart hydrogels in drug delivery: a review," Journal of Applied Biomaterials and Biomechanics 5:125-39 (2007).
Lavigne et al., "Enhanced gene expression through temperature profile-induced variations in molecular architecture of thermoresponsive polymer vectors," The Journal of Gene Medicine 9:44-54 (2007).
Lima et al., "Microbubbles as biocompatible porogens for hydrogel scaffolds," Acta Biomaterialia 8(12):4334-4341 (2012).
Madanshetty et al., "Acoustic Microcavitation—Enhancement and Applications," Journal of the Acoustical Society of America 90:1508-14 (1991).
Marchioni et al., "Structural changes induced in proteins by therapeutic ultrasounds," Ultrasonics 49:569-76 (2009).
Martz et al., "Precision Manufacture of Phase-Change Perfluorocarbon Droplets Using Microfluidics," Ultrasound in Medicine and Biology 37:1952-7 (2011).

Matsusaki et al., "Novel functional biodegradable polymer IV: pH-Sensitive controlled release of fibroblast growth factor-2 from a poly(gamma-glutamic acid)-sulfonate matrix for tissue engineering," Biomacromolecules 6:3351-6 (2005).
Mayer et al., Nucleic Acid and Peptide Aptamers: Methods and Protocols (Edited by Mayer, Humana Press) Methods in Molecular Biology (2009).
Mazzoli et al., "Use of self-expanding, hydrophilic osmotic expanders (hydrogel) in the reconstruction of congenital clinical anophthalmos," Curr. Opin. Ophthalmol. 15:426-431 (2004).
Meijering et al., "Optimization of ultrasound and microbubbles targeted gene delivery to cultured primary endothelial cells," Journal of Drug Targeting 15:664-71 (2007).
Metallo et al., "Engineering the stem cell microenvironment," Biotechnology Progress 23:18-23 (2007).
Nair et al., "Novel Polymeric Scaffolds Using Protein Microbubbles as Porogen and Growth Factor Carriers," Tissue Engineering Part C—Methods 16:23-32 (2010).
Ohl et al., "Sonoporation from jetting cavitation bubbles," Biophysical Journal 91:4285-95 (2006).
Pishchalnikov et al., "Bubble proliferation in shock wave lithotripsy occurs during inertial collapse," Nonlinear Acoustics Fundamentals and Applications pp. 460-463 (2008).
Rahim et al., "Physical parameters affecting ultrasound/microbubble-mediated gene delivery efficiency in vitro," Ultrasound in Medicine and Biology 32:1269-79 (2006).
Rahim et al., "Spatial and acoustic pressure dependence of microbubble-mediated gene delivery targeted using focused ultrasound," Journal of Gene Medicine 8:1347-57 (2006).
Rapoport et al., "Controlled and targeted tumor chemotherapy by ultrasound-activated nanoemulsions/microbubbles," Journal of Controlled Release 138:268-76 (2009).
Rapoport et al., "Ultrasound-mediated tumor imaging and nanotherapy using drug loaded, block copolymer stabilized perfluorocarbon nanoemulsions," Journal of Controlled Release 153:4-15 (2011).
Remington's Pharmaceutical Sciences, 16th Edition (1980).
Riess et al., "Oxygen Carriers (?Blood Substitutes)—Raison d'Etre, Chemistry, and Some Physiology," Chemical Reviews 101:2797-919 (2001).
Sakiyama-Elbert et al., "Controlled release of nerve growth factor from a heparin-containing fibrin-based cell ingrowth matrix," Journal of Controlled Release 69:149-58 (2000).
Sakiyama-Elbert et al., "Development of fibrin derivatives for controlled release of heparin-binding growth factors," Journal of Controlled Release 65:389-402 (2000).
Sambrook et al., Molecular Cloning: A Laboratory Manual 2nd ed. (1989).
Sanghvi, Chapter 15, Heterocyclic Base Modification in Nucleic Acids and Their Applications in Antisense Oligonucleotides, Antisense Research and Applications, pp. 289-302, Crooke, S. T. and Lebleu, B., ed., CRC Press (1993).
Satyam et al., "Macromolecular Crowding Meets Tissue Engineering by Self-Assembly: A Paradigm Shift in Regenerative Medicine," Advanced Materials 26:3024-34 (2014).
Schad et al., "In vitro characterization of perfluorocarbon droplets for focused ultrasound therapy," Physics in Medicine and Biology 55:4933-47 (2010).
Seliktar, "Designing Cell-Compatible Hydrogels for Biomedical Applications," Science 336:1124-8 (2012).
Shaikh et al., "Fibrin: A natural biodegradable scaffold in vascular tissue engineering," Cells Tissues Organs 188:333-46 (2008).
Sheeran et al., "Decafluorobutane as a Phase-Change Contrast Agent for Low-Energy Extravascular Ultrasonic Imaging," Ultrasound in Medicine and Biology 37:1518-30 (2011).
Shpak et al., "Ultrafast dynamics of the acoustic vaporization of phase-change microdroplets," The Journal of the Acoustical Society of America 133:3586 (2013).
Sojo et al., "Immunohistochemical study of vascular endothelial growth factor (VEGF) and bone morphogenetic protein-2,-4 (BMP-2,-4) on lengthened rat femurs," Journal of Cranio-Maxillofacial Surgery 33:238-45 (2005).
Thomas, "The Interaction of HgCl2 with Sodium Thymonucleate," J. Am. Chem. Soc., 76:6032-6034 (1954).

(56) References Cited

OTHER PUBLICATIONS

Thornton et al., "Enzyme responsive polymer hydrogel beads," Chemical Communications 5913-5 (2005).
Tinkov et al., "Microbubbles as Ultrasound Triggered Drug Carriers," Journal of Pharmaceutical Sciences 98:1935-61 (2009).
Tse et al., "Increased Asymmetric and Multi-Daughter Cell Division in Mechanically Confined Microenvironments," Plos One 7(6):8 pages (2012).
Tuerk et al., "Systematic Evolution of Ligands by Exponential Enrichment: RNA Ligands to Bacteriophage T4 DNA Polymerase," Science 249:505-510 (1990).
Unger et al., "Therapeutic applications of lipid-coated microbubbles," Advanced Drug Delivery Reviews 56:1291-314 (2004).
Van Gelder et al., "Effects of Poloxamer-188 on Fibrin Network Structure, Whole-Blood Clot Permeability and Fibrinolysis," Thrombosis Research 71:361-76 (1993).
Wagh et al. "Tissue expansion: Concepts, techniques and unfavourable results," Indian J Plast Surg. 46(2):333-348 (2013).
Ward et al., "Ultrasound-induced cell lysis and sonoporation enhanced by contrast agents," Journal of the Acoustical Society of America 105:2951-7 (1999).
Whelan et al., "Fibrin as a delivery system in wound healing tissue engineering applications," Journal of Controlled Release 196:1-8 (2014).
Wong et al., "Bubble evolution in acoustic droplet vaporization at physiological temperature via ultra-high speed imaging," Soft Matter 7:4009-16 (2011).
Wu et al., "Molecule-scale controlled-release system based on light-responsive silica nanoparticles," Chemical Communications 23:2662-4 (2008).
Yamane et al., "On the Complexing of Desoxyribonucleic Acid (DNA) by Mercuric Ion," J. Am. Chem. Soc., 83(12):2599-2607 (1961).
Yan et al., "Aptamers and aptamer targeted delivery," RNA Biol. 6(3) 316-320 (2009).
Zhang "An Extremely Stable and Orthogonal DNA Base Pair with a Simplified Three-Carbon Backbone," J. Am. Chem. Soc., 127:74-75 (2005).
Zhao et al., "Active scaffolds for on-demand drug and cell delivery," PNAS 108:67-72 (2011).
Zimmermann, et al., "A Novel Silver(I)-Mediated DNA Base Pair," J. Am. Chem. Soc., 124:13684-13685 (2002).

\* cited by examiner

BIODEGRADABLE HYDROGEL FOR TISSUE EXPANSION

CROSS REFERENCE TO RELATED APPLICATIONS

This application is a U.S. National Phase of International Application No. PCT/US2016/053556 filed Sep. 23, 2016, which claims the benefit of U.S. Provisional Application Ser. No. 62/234,422, filed Sep. 29, 2015, the disclosures of which are incorporated herein by reference in their entirety.

STATEMENT OF GOVERNMENT INTEREST

This invention was made with government support under AR065010 awarded by the National Institutes of Health. The Government has certain rights in the invention.

FIELD OF THE INVENTION

The present invention is directed to compositions and methods for delivering a biodegradable hydrogel to an individual for tissue expansion.

BACKGROUND OF THE INVENTION

The background descriptions provided throughout are for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

The estimated revenues for the U.S. Tissue Engineering Market in 2000 are $230 million with a growth rate of 20 percent. Revenues will be led by bone regeneration products (48.5 percent of revenues), followed by skin engineering products (36.8 percent of revenues) and cartilage repair products (14.7 percent of revenues). Breast reconstruction typically is performed to re-create one or both breasts after a single or double mastectomy.

Fibrin scaffolds are highly porous, protein-based hydrogels frequently used in regenerative medicine as a substrate for cells and for encapsulation of proteins such as growth factors (GFs) (Shaikh et al. 2008; Dehghani and Annabi 2011; Seliktar 2012). Similar to other hydrogels, the release of a bioactive molecule (i.e., payload) from a conventional fibrin scaffold as well as degradation of the scaffold are dominated by processes such as molecular diffusion, material degradation, and cell migration. Thus the rate that biochemical (e.g., GFs) or mechanical (e.g., microporosity) cues are presented in a conventional fibrin scaffold cannot be externally controlled spatially or temporally, especially after the scaffold is implanted in vivo. It is well documented that spatial and temporal patterns of GF signaling are critically important in regenerative processes (Bos et al. 2001; Sojo et al. 2005); additionally, cellular processes are influenced by the mechanical properties of the local scaffold microenvironment (Metallo et al. 2007; Tse et al. 2012; Barthes et al. 2014; Fujie et al. 2014; Satyam et al. 2014). Alternatively, scaffolds have been designed to respond to environmental or externally applied stimuli—such as light, electricity, magnetic fields, temperature, enzymes, and pH—in order to obtain spatiotemporal control of payload release or to modify scaffold architecture after implantation (Sakiyama-Elbert and Hubbell 2000b; Sakiyama-Elbert and Hubbell 2000a; Matsusaki and Akashi 2005; Thornton et al. 2005; Frimpong et al. 2007; Kulkarni and Biswanath 2007; Lavigne et al. 2007; Wu et al. 2008; Zhao et al. 2011). Despite their promising potential in controlling both biochemical and mechanical cues, further development of responsive scaffolds is limited in part by the clinical translatability of the modulating stimulus, especially in terms of focusing the stimulus or targeting deeply located scaffolds.

Ultrasound (US) has been explored as a stimulus for achieving spatial and temporal control with responsive scaffolds due to its potential for translatability. Unlike other stimuli, US can be applied non-invasively, focused with submillimeter precision, and penetrate deep within the body. Broadly, US can be used to generate mechanical and/or thermal effects within a scaffold to achieve on-demand control. In many instances, US-responsive scaffolds contain sonosensitive particles such as emulsions or microbubbles, thus making the scaffold more responsive to US (Epstein-Barash et al. 2010; Fabiilli et al. 2013). However, it has been demonstrated using low frequency US that payload release can be modulated from scaffolds in the absence of sonosensitive particles (Huebsch et al. 2014). Sonosensitive particles are usually administered intravascularly for US-based imaging or therapy, with microbubbles used clinically as US contrast agents. These particles are typically micron-size in diameter, contain a perfluorocarbon (PFC) dispersed (i.e., core) phase, and are stabilized by a surfactant shell. Microbubbles, which contain a gaseous PFC core, have been used to indirectly facilitate payload delivery from an in situ cross-linking hydrogel containing liposomes co-encapsulated with the microbubbles (Epstein-Barash et al. 2010). In the absence of US, microbubbles have also been used to create on-demand, microporous agarose hydrogels (Lima et al. 2012) or to simultaneously act as a porogen and GF carrier within poly(lactic-co-glycolic-acid) scaffolds (Nair et al. 2010).

SUMMARY OF THE INVENTION

Tissue expansion is a technique used to grow extra skin via mechanical stretching. Tissue expansion is widely used within plastic and reconstructive surgeries and has advantages relative to other techniques such as split-thickness skin grafts.

Accordingly, in some aspects the disclosure provides a device comprising (a) a tissue scaffold and (b) an emulsion that comprises a perfluorocarbon (PFC) droplet.

In some aspects, a method of treating a patient in need of tissue expansion is provided, the method comprising administering to the patient a biodegradable hydrogel scaffold comprising a perfluorocarbon (PFC) emulsion. In some embodiments, density of the scaffold is between about 100 µg/mL to about 100 mg/mL fibrinogen. In various embodiments, the PFC emulsion contains perfluoropentane (PFP) as the dispersed phase. In some embodiments, the PFC emulsion contains perfluorohexane (PFH) as the dispersed phase. The PFC emulsion, in some embodiments, comprises a mixture of perfluorocarbons. In related embodiments, the mixture is 90% PFP:10% PFH, 95% PFP:5% PFH, 80% PFP:20% PFH, or 70% PFP:30% PFH.

In some embodiments, the patient in need of tissue expansion has undergone plastic surgery. In further embodiments, the patient in need of tissue expansion has undergone breast reconstruction, rhinoplasty, or trauma reconstruction. In some embodiments, the patient in need of tissue expansion has undergone burn surgery. In still further embodiments, the patient in need of tissue expansion has undergone reconstruction of congenital or acquired defects of the scalp, face, ear, neck, trunk, breast, upper limb/extremity, or lower limb/extremity. In some embodiments, the patient in need of tissue expansion has undergone skin reconstruction following removal of congenital nevus or hemangioma, breast reconstruction for defects resulting from mastectomy or lumpectomy, or tissue reconstruction following surgical resection. In additional embodiments, the patient in need of tissue expansion suffers from congenital anophthalmia or diabetes. In some embodiments, the patient in need of tissue expansion suffers from facial or breast asymmetry. In further embodiments, the patient in need of tissue expansion suffers from cleft lip, alveolus, or palate. In still further embodiments, the patient in need of tissue expansion has undergone reconstructive urology.

In some embodiments, methods of the disclosure further comprise exposing the scaffold to ultrasound.

In further aspects, a method of delivering an effective amount of a therapeutic agent to an individual in need thereof is provided, comprising administering to the individual a device comprising (a) a tissue scaffold; (b) an emulsion that comprises a perfluorocarbon (PFC) droplet comprising the therapeutic agent in the interior thereof, wherein the scaffold is exposed to ultrasound at a pulse repetition frequency of from about 1 Hertz (Hz) to about 50 Hz thereby causing vaporization of the PFC droplet and delivery of the therapeutic agent.

In some embodiments, the device further comprises a progenitor cell. In further embodiments, the progenitor cell is a fibroblast, a chondrocyte, an osteoblast, a skeletal myocyte, a cardiac myocyte, a mesenchymal progenitor cell, a hematopoietic progenitor cell, a satellite cell, a neural progenitor cell, a pancreatic progenitor cell, a blast cell or a combination thereof.

The disclosure also provides embodiments, in which the emulsion is a double emulsion comprising a primary emulsion and a secondary emulsion. In some embodiments, the primary emulsion comprises water-in-PFC, and the secondary emulsion comprises water-in-PFC-in-water.

In further embodiments, a device of the disclosure further comprises a surfactant. In related embodiments, a first surfactant stabilizing the primary emulsion is a triblock copolymer, and a second surfactant stabilizing the secondary emulsion is an aqueous soluble surfactant. In further embodiments, the triblock copolymer comprises a perfluoroether and polyethylene glycol. In still further embodiments, the aqueous soluble surfactant is selected from the group consisting of a protein, a lipid, an ionic copolymer and a non-ionic copolymer.

In various embodiments, initial pore size of the tissue scaffold is at least about 100 nanometers (nm). In some embodiments, vaporization of the PFC droplet results in a final pore size of the tissue scaffold of at least about 40 μm and up to about 5 millimeters (mm). In further embodiments, the density of the tissue scaffold is between about 100 μg/mL to about 100 mg/mL fibrinogen.

The disclosure also provides embodiments, in which the device is implantable. In some embodiments, the device is topical.

In various embodiments, the therapeutic agent is selected from the group consisting of a polypeptide, a peptide, a polynucleotide, a viral particle, a gas, a contrast agent and a small molecule. In some embodiments, the therapeutic agent is controlled spatially. In further embodiments, release of the therapeutic agent is controlled temporally.

DESCRIPTION

Figure 1:
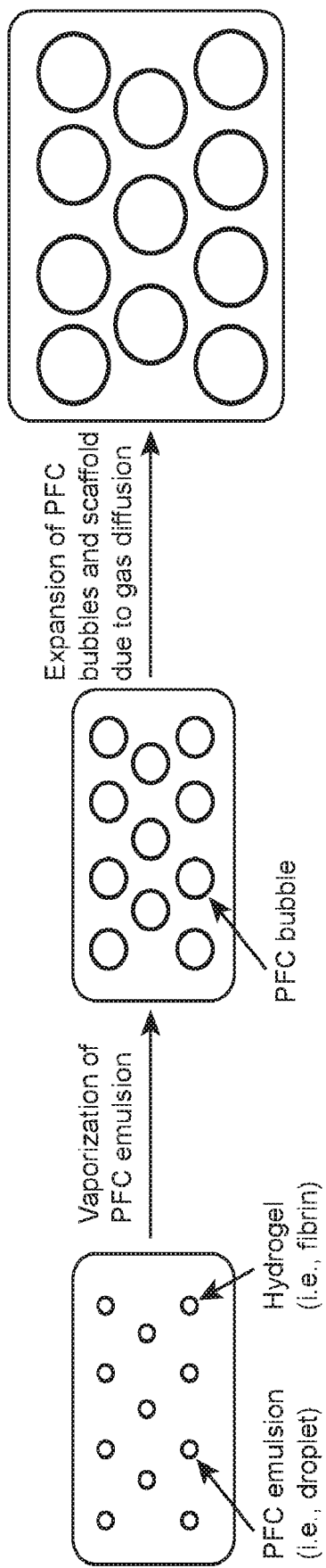
FIG. 1 depicts a schematic demonstrating how the scaffold causes tissue expansion and a mechanism of tissue expansion action of a device of the disclosure.

Sonosensitive emulsions and microbubbles have been studied extensively in the fields of diagnostic and therapeutic ultrasound, typically for contrast-enhanced imaging, intravascular delivery, and applications in cancer treatment [Diaz-Lopez et al., Pharmaceutical Research 27: 1-16 (2010); Tinkov et al., Journal of Pharmaceutical Sciences 98: 1935-61 (2009); Ibsen et al., Journal of Controlled Release: Official Journal of the Controlled Release Society 155: 358-66 (2011)]. The potential for these vehicles to be applied in tissue expansion, however, is largely unexplored. Thus, in some aspects the present disclosure provides composite materials that incorporate perfluorocarbon (PFC) droplets in a biodegradable hydrogel scaffold for use in tissue expansion.

Human tissues possess an innate ability to stretch and gradually expand over a period of time under the application of constant stress, both in physiological and pathological conditions [Milind et al., Indian J Plast Surg. 46(2): 333-348 (2013)]. For example, laxity of the skin and soft tissues all over the body following massive weight loss, or the stretching of the chest skin to form ptotic breast mound following puberty, are forms of physiological tissue expansion. In pathological situations, the skin and soft-tissues expand over benign tumors such as lipomas and malignant tumors such as soft-tissue sarcomas [Milind et al., Indian J Plast Surg. 46(2): 333-348 (2013)].

Over the last three decades, the basic principles underlying tissue expansion have been adapted to design tissue expanders that have improved and revolutionized the field of reconstructive surgery. Tissue expanders are temporary inflatable implants that are positioned under the skin to facilitate the increase of tissue dimensions for reconstruction [Kobus et al., J. Plast. Reconstr. Aesthet. Surg. 60, 414-421 (2007)]. The tissue expanders traditionally comprise silicon balloons, molded into pre-shaped prosthesis, which can be filled with saline through a valve system, which is either incorporated on the expander's surface or is remote and connected by a flexible silastic filling tube to the expander. The process of tissue expansion is a vital and valuable tool in the reconstructive armamentarium but requires a careful and correct patient selection, meticulous planning and precise step-wise execution. The use of a prosthesis, however, has drawbacks including the long duration of the process and several ambiguous intrinsic and extrinsic factors related to the same. Complications may be minor, which are related to the implant system itself and inadequacy of completion of the goals, or they may be major, which forces one to alter the original surgical plan or temporarily abandon it.

Minor complications include issues related to hematomas and seromas, valve placement or location, exposure of the valve alone and inadequacy of the expansion related to the defect/lesion. Major complications include (1) cellulitis and closed infections, (2) exposure of the expander balloon itself, (3) deflation of the balloon, (4) ischaemic necrosis of the overlying skin and (5) area-wise, expansion in the lower extremity resulting in reduced vascularity in the lower limbs and contours of the limbs on which the expander lies. To attempt to overcome the shortcomings of balloon-filled expanders, the use of hydrogels as tissue expanders in reconstructive surgery was developed [Mazzoli et al., Curr. Opin. Ophthalmol. 15: 426-431 (2004)] which exploited the osmotically driven expansion of a biocompatible poly(hydroxylethyl methacrylate) hydrogel. However, in the hydrogels expanders were found to swell rapidly resulting in high-pressure peaks that caused hypoxia in the tissue and thus also skin damage.

The presented studies build upon previous work where the utility of fibrin scaffolds doped with sonosensitive PFC emulsions, termed here acoustically responsive scaffolds (ARSs), was demonstrated. US was used to modulate GF release from the ARS as well as induce drastic changes in architecture and shear stiffness of the ARS (Fabiilli et al. 2013; U.S. Patent Application Publication No. 2013/0330389, incorporated by reference herein in its entirety). Fibrin was chosen as the hydrogel in the ARS due to its widespread use within the field of tissue engineering as a delivery system for GFs, cells, drugs, and genes (Whelan et al. 2014). Sonosensitive PFC emulsions, with single or double structures, have been used as on-demand contrast agents and delivery vehicles for bioactive payloads, respectively (Kripfgans et al. 2000; Unger et al. 2004; Diaz-Lopez et al. 2010; Fabiilli et al. 2013; Javadi et al. 2013). The PFC within these emulsions transitions from a liquid into a gas when the emulsion is exposed to US above a specific acoustic amplitude. This phase transition is termed acoustic droplet vaporization (ADV) (Kripfgans et al. 2004) and occurs in a microsecond time frame (Fabiilli et al. 2010; Wong et al. 2011). PFCs such as perfluoropentane (PFP, $C_5F_{12}$, 29° C. boiling point) and perfluorohexane (PFH, $C_6F_{14}$, 56° C. boiling point) are typically used in sonosensitive emulsions because of their biocompatibility and inertness. The emulsification process (i.e., formation of droplets) prevents low boiling point PFCs, like PFP, from vaporizing at homeostatic body temperature (37° C.) due to an increase in Laplace pressure, which causes an elevation of the PFC boiling point within the droplets (Rapoport et al. 2009; Sheeran et al. 2011). Sonosensitive emulsions can possess both single and double emulsion structures. With single emulsions of the form PFC-in-water (PFC/W), the PFC is dispersed within an aqueous continuous phase. For delivery of payloads such as GFs, a secondary dispersed phase is added since PFCs are extremely hydrophobic and lipophobic. Thus double emulsions of the form water-in-PFC-in-water ($W_1$/PFC/$W_2$) have been used for GF delivery in ARSs whereby the GF is contained within the $W_1$ phase (Fabiilli et al. 2013).

For responsive scaffolds, the physicochemical properties of the scaffold are related to the manner in which the scaffold will respond to a stimulus. Conversely, the properties of the stimulus (e.g., intensity, duration, or directionality) impact the response of the scaffold. Thus, elucidating the mechanisms that occur when an ARS is exposed to US is critical in not only achieving optimal payload release from the scaffold, but also relevant for facilitating regenerative processes that could occur within or adjacent to the ARS. In addition to ADV, inertial cavitation (IC) has been observed when sonosensitive emulsions undergo a phase shift (Fabiilli et al. 2009). IC can occur when a bubble, either generated by ADV or the nucleation of dissolved gas, rapidly expands and collapses due to US exposure. This violent behavior by the bubble can generate very high temperatures and velocities at the bubble site, which can ultimately cause bioeffects such as cellular damage and sonoporation (Ferrara et al. 2007).

Provided herein are devices that comprise a tissue scaffold and are designed for use in tissue expansion therapies. This tissue expansion technology comprises of a hydrogel scaffold that is injected at a desired site of skin growth. In some aspects, the scaffold polymerizes in situ and is ultimately biodegradable. The scaffold also contains a perfluorocarbon (PFC) emulsion that vaporizes from liquid droplets into gas bubbles when implanted. In some aspects, vaporization of the emulsion occurs in response to the body heat of the subject bearing the scaffold. Thus, in some aspects, vaporization of the emulsion occurs in the absence of ultrasound.

In further aspects, vaporization of the emulsion is facilitated through the application of ultrasound. In some embodiments, vaporization of the emulsion facilitated through the application of ultrasound enables anisotropic expansion of the scaffold. In further embodiments, vaporization of the emulsion facilitated through the application of ultrasound enables isotropic expansion of the scaffold. Regardless of the method of vaporization of the liquid droplets, the resulting gas bubbles, which remain stuck in the matrix, begin to in-gas. Thus, the matrix expands in size and causes the skin the stretch (FIG. 1). Compared to existing technologies, and in some aspects, the devices of the present disclosure reduce complications associated with, for example and without limitation, infection, tissue necrosis, and hematoma.

The devices disclosed herein are also highly tunable, meaning that many aspects of the design and use of the device may be adjusted to affect the functioning of the device. These aspects include, but are not limited to, the tissue scaffold (including the shape and/or size of the scaffold), the emulsion, the location of implantation, and the use of ultrasound. Each of these aspects is described in detail below.

It is noted here that, as used in this specification and the appended claims, the singular forms "a," "an," and "the" include plural reference unless the context clearly dictates otherwise.

Tissue Scaffold

The device disclosed herein may be formulated as an in situ-polymerizable, porous, biodegradable tissue scaffold that further comprises a PFC emulsion. The tissue scaffold provides a substrate for cell adhesion, and comprises several aspects that allow for direct control over the structure and properties of the device. These aspects include, but are not limited to, the density, pore size, shape, size, and/or composition of the scaffold.

It will be appreciated that the various features of the devices disclosed herein, in various embodiments, act in concert. For example and without limitation, vaporization of a population of PFC droplets in a specific subvolume of the tissue scaffold results in a structural modification of the tissue scaffold (i.e., a change in pore size/porosity) in that same subvolume, which in turn results in enhanced invasion of host cells in the subvolume of the scaffold.

As used herein "tissue scaffold," "scaffold" and "hydrogel scaffold" are used interchangeably.

The shape of the scaffold can be modulated, in various embodiments, by 1) controlling how the scaffold is injected into the subcutaneous space or 2) implanting a preformed scaffold of a specific shape/geometry.

In further embodiments, the size of the scaffold controls its properties. The disclosure generally contemplates implant volumes of from about 0.5 milliliters (mL) to about 1000 mL. The implant volume is generally related to its intended application. By way of example, tissue expansion for breast reconstruction or for burn surgery would require a larger implant volume, e.g., from about 100 mL to about 600 mL. Regardless, implant volumes of from about 1 mL to about 500 mL, or from about 5 mL to about 100 mL, or from about 10 mL to about 100 mL, or from about 5 mL to about 50 mL are contemplated. Specific implant volumes of at least about 0.5 mL, at least about 1 mL, at least about 2 mL, at least about 5 mL, at least about 10 mL, at least about 50 mL, at least about 100 mL, at least about 200 mL, at least about 300 mL, or at least about 500 mL are also contemplated, as are implant volumes less than 1000 mL, or less than about 800 mL, or less than about 500 mL, or less than about 300 mL, or less than about 100 mL, or less than about 50 mL, or less than about 20 mL, or less than about 10 mL, or less than about 5 mL, or less than about 1 mL.

Composition

Methods of making tissue scaffolds are described in Gazit et al., U.S. Patent Application Publication Number 20090214649 and Fabiilli et al., U.S. Patent Application Publication Number 20130330389, each which is incorporated by reference herein in their entireties.

Tissue scaffolds for use in the devices and methods disclosed herein are comprised, in some embodiments, of proteins. For example and without limitation, the tissue scaffold is produced using fibrinogen and thrombin. In additional embodiments, the disclosure contemplates use of self-assembling peptide-based hydrogels, gelatin hydrogels, elastin and elastin-like hydrogels, collagen hydrogels, polysaccharide-based hydrogels (including but not limited to methylcellulose, agarose, alginate, and hyaluronic acid), composite hydrogels (including but not limited to collagen+ fibrin blends, collagen+glycosaminoglycan blends, blends of the above and below), and synthetic hydrogels (including but not limited to polyethylene glycol, polyethylene glycol-fibrinogen conjugates, oligo(poly(ethylene glycol)-fumarate) derivatives, polyvinyl alcohol, and other hydrogels. Specific embodiments of the composition of tissue scaffolds contemplated by the disclosure are exemplified herein below.

In further embodiments, the tissue scaffold further comprises a progenitor cell. The progenitor cell, in various embodiments, is a fibroblast, chondrocyte, osteoblast, skeletal myocyte, cardiac myocyte, mesenchymal progenitor cell, an adipocyte progenitor cell, hematopoietic progenitor cell, satellite cell, neural progenitor cell, pancreatic progenitor cell, blast cell, a lymphoid progenitor cell, a myeloid progenitor cell, an endothelial progenitor cell, an epithelial progenitor cell, a renal progenitor cell, a retinal progenitor cell or a combination thereof. In further embodiments, the tissue scaffold comprises a population of progenitor cells.

In some embodiments, the relative amounts of protein (for example and without limitation, fibrinogen and thrombin) used for polymerizing the tissue scaffold control the rate of polymerization of the scaffold. For example and without limitation, a more rapid polymerization (less than about one minute) of the scaffold may be desired when the device is used subcutaneously when the amount of a therapeutic agent is to be concentrated in a specific tissue/region of the body. In this way, diffusion of the device is limited. For a more widespread distribution of the device, a slower polymerization (about one to several minutes or more) of the tissue scaffold may be desired. The relative rates of polymerization can be empirically determined by one of skill in the art.

Density

The density of the tissue scaffold refers to the concentration of protein dissolved in a solvent, wherein the protein is capable of polymerizing to form the scaffold. In general, a higher density scaffold leads to a longer term stability of the PFC droplets within the hydrogel scaffold. This is because a higher density scaffold provides viscous resistance to the vaporization of the PFC droplets within the scaffold. Therefore, in aspects in which the liquid droplets are vaporized via ultrasound, a higher acoustic pressure is required to vaporize droplets within a higher density scaffold than a lower density scaffold. Ultrasound-bubble interactions are more pronounced at lower scaffold densities than at higher scaffold densities due to the viscous resistance of the scaffold. Therefore, effects derived from ultrasound-bubble interactions such as mechanical stimulation of cells or sonoporation of cells are more pronounced at lower scaffold densities.

Scaffold density is related to the vaporizability of the emulsion as well as the rate at which the resulting gas bubbles will in-gas. The expansion of the scaffold relies on the vaporization of the droplets and the in-gassing of the bubbles. Additionally, scaffold degradation is related to scaffold density, which in some aspects impacts the expansion of the scaffold. Vaporization and in-gassing will occur at a slower rate in high density scaffolds versus low density scaffolds. Additionally, high density scaffolds will degrade more slowly than lower density scaffolds. Thus, as a high density scaffold degrades, its effective density changes, which means that the vaporizability/in-gassing properties of the scaffold changes.

The disclosure therefore contemplates the use of various densities of protein within the hydrogel scaffold. According to the disclosure, the density of protein within the tissue scaffold is at least about 100 µg/mL and up to about 100 mg/mL or more. In some embodiments, the density of the protein within the tissue scaffold is from about 100 µg/mL to about 90 mg/mL, or from about 100 µg/mL to about 80 mg/mL, or from about 100 µg/mL to about 70 mg/mL, or from about 100 µg/mL to about 60 mg/mL, or from about 100 µg/mL to about 50 mg/mL, or from about 100 µg/mL to about 40 mg/mL, or from about 100 µg/mL to about 30 mg/mL, or from about 100 µg/mL to about 20 mg/mL, or from about 100 µg/mL to about 10 mg/mL or from about 100 µg/mL to about 1 mg/mL. In various embodiments, the density of the protein within the tissue scaffold is from about 1 mg/mL to about 100 mg/mL, or from about 1 mg/mL to about 50 mg/mL, or from about 1 mg/mL to about 40 mg/mL, or from about 1 mg/mL to about 30 mg/mL, or from about 1 mg/mL to about 20 mg/mL, or from about 1 mg/mL to about 10 mg/mL. In further embodiments, the density of the protein within the tissue scaffold is from about 1 mg/mL and up to about 5 mg/mL, about 10 mg/mL, about 15 mg/mL or about 20 mg/mL or more. Further embodiments contemplated include those wherein the density of the protein within the tissue scaffold is from about 1 mg/mL, from about 5 mg/mL, from about 10 mg/mL, from about 15 mg/mL, from about 20 mg/mL, from about 25 mg/mL, from about 30 mg/mL, from about 35 mg/mL, from about 40 mg/mL or from about 45 mg/mL up to about 50 mg/mL. In specific embodiments, the density of the protein within the tissue scaffold is about 100 µg/mL, 150 µg/mL, 200 µg/mL, 250 µg/mL, 300 µg/mL, 350 µg/mL, 400 µg/mL, 450 µg/mL, 500 µg/mL, 550 µg/mL, 600 µg/mL, 650 µg/mL, 700 µg/mL, 750 µg/mL, 800 µg/mL, 850 µg/mL, 900 µg/mL, 950 µg/mL, 1 mg/mL, about 2 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL or about 50 mg/mL. Indeed, the disclosure contemplates the use any density between 1 mg/mL and 50 mg/mL, inclusive.

Porosity/Pore Size and Stiffness/Dissipation

The porosity and pore size of the tissue scaffold are additional aspects that afford the ability to control aspects of the properties of the device. Porosity refers to the volume fraction of open space within a tissue scaffold (typically reported as a percentage) and can be determined by microscopic methods or through permeation experiments. Porosity, along with pore size (a characteristic dimension of the open structure(s) within the scaffold) and pore interconnectivity contribute to the resistance to fluid flow, molecular diffusion, and cellular invasion of a tissue scaffold. Most hydrogels are highly porous with porosities of that can be in excess of 99% (i.e., 99% by volume open space, 1% by volume solid material) but the pore sizes are quite small, in the range of 500 nm to 15 µm diameter pores. These pores are small enough to limit migration of cells and diffusion of one or more therapeutic agents into (or out of) the scaffold. The porosity and pore size of hydrogel scaffolds are generally dependent on polymerization conditions including but not limited to the concentration of scaffold precursors (for example, and without limitation, synthetic or biological polymers, enzymes, cross linking agents, and buffer systems), temperature, and atmosphere used during preparation of the scaffold.

The porosity of the scaffold may be adjusted, however, through increasing the pore size of the scaffold, which is effected via vaporization of the PFC droplets within the scaffold. ADV increases gel porosity due to the phase-transitioning of the PFC liquid into a gas. PFC droplet vaporization (e.g., via boiling or ultrasound) results in an increase in scaffold pore size, which ultimately results in an increase in porosity.

Adjusting the porosity of the scaffold, and thus the amount of fluid and number of cells that are able to pass through the scaffold, allows for the ability to control the relative rate of degradation of the scaffold. As discussed above, a higher porosity results in more fluid penetrating into the scaffold and increased cellular in-growth, which in turn will lead to a faster degradation of the scaffold. A lower porosity, on the other hand, results in less fluid passing through the scaffold and less cellular in-growth, which leads to a slower degradation of the scaffold.

In addition, while in some embodiments the porosity of the scaffold is high prior to PFC droplet vaporization, the pore size in these embodiments is small. Therefore, while fluid is able to pass through the scaffold, cells cannot readily pass through. In these embodiments, the increase in pore size resulting from PFC droplet vaporization further allows cells to infiltrate the scaffold more easily. Thus, cells that are required for tissue regeneration are able to enter the scaffold and perform their functions.

The disclosure contemplates that in one embodiment the initial (i.e., prior to PFC droplet vaporization) pore size of the polymerized scaffold is, on average, about 100 nanometers (nm). In further embodiments, the initial pore size is at least about 100 nm to about 10 µm, or at least about 100 nm to about 5 µm, or at least about 100 nm to about 2 µm, or at least about 100 nm to about 900 nm, or at least about 100 nm to about 800 nm, or at least about 100 nm to about 700 nm, or at least about 100 nm to about 600 nm, or at least about 100 nm to about 500 nm, or at least about 100 nm to about 400 nm, or at least about 100 nm to about 300 nm, or at least about 100 nm to about 200 nm. In specific embodiments, the initial pore size of the polymerized scaffold is at least about 100 nm, 200 nm, 300 nm, 400 nm, 500 nm, 600 nm, 700 nm, 800 nm, 900 nm, 950 nm, 1000 nm, 2 µm, 5 µm, 7 µm, 10 µm or more.

As discussed above, scaffold pore size is increased by PFC droplet vaporization. Thus, the disclosure also contemplates that, in one embodiment, the final (i.e., after PFC droplet vaporization) pore size of the polymerized scaffold is about 40 µm. In further embodiments, the final pore size is at least about 1 µm and up to about 50 µm, or at least about 5 µm and up to about 40 µm, or at least about 40 µm and up to about 5 millimeters (mm), or at least about 40 µm and up to about 4 mm, or at least about 40 µm and up to about 3 mm, or at least about 40 µm and up to about 2 mm, or at least about 40 µm and up to about 1 mm, or at least about 100 µm and up to about 5 mm, or at least about 100 µm and up to about 4 mm, or at least about 100 µm and up to about 3 mm, or at least about 100 µm and up to about 2 mm, or at least about 100 µm and up to about 1 mm, or at least about 100 µm and up to about 900 µm, or at least about 100 µm and up to about 800 µm, or at least about 100 µm and up to about 500 µm m. In additional embodiments, the final pore size is at least about 200 µm and up to about 1 mm, or at least about 500 µm and up to about 1 mm, or at least about 200 µm and up to about 800 µm, or at least about 500 µm and up to about 2 mm. In specific embodiments, the final pore size of the polymerized scaffold is at least about 1 µm, 5 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm or more.

Another way of describing the initial versus the final pore size of the polymerized scaffold is by percent volume increase of the tissue scaffold. Accordingly, the disclosure provides devices in which, following vaporization, the tissue scaffold increase by about 1% up to about 30% or more, or by about 5% up to about 30%, or by about 10% up to about 30% or more in volume.

Mechanical properties such as scaffold stiffness and viscoelasticity can also be modulated via PFC droplet vaporization. Viscoelasticity is defined in terms of the dissipation factor, which is the tangent of the phase angle $\delta$. In general, droplet vaporization causes an increase in shear stiffness of a scaffold, which is also a general indicator of the viscoelasticity of the scaffold. Higher viscoelasticity is indicative of a more dissipative mechanical response. Modulation of properties such as pore size and stiffness/viscoelasticity are useful in tailoring the function of the scaffold. Accordingly, in some aspects, methods of controlling and/or modulating the porosity and/or pore size of a tissue scaffold are provided by the disclosure, and comprise the step of exposing all or a portion of the tissue scaffold to ultrasound. In this way, the porosity and/or pore size and/or stiffness/viscoelasticity of the tissue scaffold is modulated in a global or localized manner. Local increases (i.e., an increase in at least one region or subvolume of the scaffold versus the entirety of the scaffold) in pore size and/or stiffness, in various embodiments, will allow the infiltration of cells and/or fluid into the scaffold, where they proliferate and differentiate. The local or global shifts in pore structure and/or stiffness also provide, in some embodiments, specific topographical cues that promote differentiation of encapsulated or invading cells along various lineages (for example and without limitation, endothelial or osteogenic). For example, Engler et al. [Cell 126: 677-689 (2006)] described how mesenchymal stem cell (MSC) differentiation can be influenced by the stiffness of a scaffold. Specifically, Engler et al. [Cell 126: 677-689 (2006)] described how MSCs display neurogenic, myogenic, or osteogenic characteristics when grown on scaffolds with stiffnesses in the range of 0.1-1 kPa, 8-17 kPa, and 25-40 kPa, respectively. Thus, in some embodiments, the disclosure contemplates that vaporization of the PFC droplet results in a stiffness of the tissue scaffold that is from about 0.05 kilopascal (kPa) to about 40 kPa, or from about 0.1 kPa to about 1 kPa, or from about 1 kPa to about 17 kPa, or from about 20 kPa to about 40 kPa, or from about 0.05 kPa to about 5 kPa, or from about 0.05 kPa to about 2 kPa.

Emulsion

The devices disclosed herein comprise an emulsion, and the emulsion further comprises PFC droplets. Specifically, and in various embodiments, the present disclosure contemplates the use of double emulsions. Double emulsions comprising PFC droplets are known in the art, and are described in Fabiilli et al., Pharm Res. 27(12): 2753-2765 (2010), the disclosure of which is incorporated by reference herein in its entirety. In further embodiments, a single emulsion (PFC-in-water) is used. PFCs contemplated for use according to the disclosure include those with lower (i.e., below 37° C.) and higher (i.e., above 37° C.) boiling points. Specific PFCs contemplated by the disclosure include perfluorocarbons with the formula $C_nF_{2n+2}$ such as perfluoropropane, perfluorobutane, perfluoropentane, perfluorohexane, perfluoroheptane, and perfluorooctane.

In further embodiments, a tissue scaffold comprises a combination of PFCs. Ratios of PFCs in an emulsion are, in various embodiments, 95%:5%, 90%:10%, 85%:15%, 80%: 20%, 75%:25%, 70%:30%, 65%:35%, 60%:40%, 55%: 45%, or 50%:50%. By way of example, in some embodiments a tissue scaffold comprises 95% perfluoropentane and 5% perfluorohexane. PFCs are completely miscible with one another. So by mixing two or more PFCs, a fluid with a tunable boiling point is acquired. Emulsions with higher boiling points are more resistant to vaporization. Thus, for tissue expansion, it is contemplated that in various embodiments a PFC (or mixture of PFCs) with a lower boiling point is used which would facilitate vaporization (in the absence of ultrasound) and thus tissue expansion.

A double emulsion comprises a primary (water-in-PFC) and a secondary emulsion (water-in-PFC-in-water), and is one in which aqueous droplets are suspended within a PFC droplet and have the following structure: water-in-PFC-in-water (W1/PFC/W2). Double emulsions are utilized because hydrophilic or lipophilic therapeutic agents are not soluble within PFC. Thus, by creating a double emulsion, the droplets are able to carry and deliver both hydrophilic and lipophilic therapeutic agents. In the case of a lipophilic therapeutic agent, the double emulsion would have the following structure: oil-in-PFC-in-water. "Oil" denotes a phase that can solubilize the lipophilic therapeutic agent.

Emulsion Features

As discussed hereinabove, PFC emulsions can be vaporized into gas bubbles via ultrasound or boiling of the PFC droplets due to their relatively low boiling points. Since ultrasound can be focused non-invasively and at a precise depth with sub-millimeter precision, the location at which droplet vaporization occurs can be controlled externally. Thus, gel porosity in implanted tissue scaffolds are modulated using ultrasound-mediated PFC droplet vaporization. Additionally, due to the high oxygen-dissolving ability of liquid PFC [Riess, Chemical Reviews. 101(9):2797-919 (2001)], the droplets, in the absence of ultrasound-mediated PFC droplet vaporization, could be used to increase the survival of cells that are located deep within the gel [Chin et al., Biotechnology Progress. 24(2):358-66 (2008)].

In further embodiments, it is contemplated that a device comprises more than one population of PFC droplets. In these embodiments, a first population of PFC droplets would have the property of vaporizing at a first ultrasound frequency and/or acoustic pressure threshold, and a second population of PFC droplets would have the property of vaporizing at a second ultrasound frequency and/or acoustic pressure threshold. Additional embodiments of the disclosure contemplate further populations of PFC droplets, wherein each of the further populations has the property of vaporizing at a unique ultrasound frequency and/or acoustic pressure threshold. The disclosure contemplates that ultrasound frequencies between about 0.5 MHz and about 50 MHz are useful in the devices and methods disclosed herein to enable efficient vaporization of the droplets. The disclosure contemplates that ultrasound pulse repetition frequencies (i.e., the number of ultrasound pulses per unit time) between about 1 Hz and about 50 Hz are useful in the devices and methods disclosed herein. This range of pulse repetition frequencies will enable efficient droplet vaporization while minimizing the likelihood of unwanted mechanical or thermal bioeffects caused by the ultrasound exposure. Thus, in various embodiments, the disclosure contemplates a tissue scaffold that comprises at least 1, 2, 3, 4, 5, 6, 7, 8, 9, 10, 15, 20 or more populations of PFC droplets. In further embodiments, more than one device, each device comprising a tissue scaffold that comprises one or more populations of PFC droplets, is administered. In various embodiments, multiple populations of droplets are important in terms of varying the expansion rate of the scaffold. By way of example, start with a scaffold comprising Emulsion A and Emulsion B. Emulsion A, which contains a low boiling point PFC (or mixture) will vaporize quickly upon implantation (over the course of, e.g., hours or days). Emulsion B, which has a higher boiling point, will vaporize more slowly over the course of weeks (in some embodiments, in response to the degradation of the scaffold).

The disclosure also provides a device wherein a single population of PFC droplets comprises one or more subpopulations of PFC droplets, wherein each subpopulation has the property of vaporizing at a distinct ultrasound frequency and/or acoustic pressure threshold. Accordingly, in one aspect the disclosure provides a device comprising (a) a tissue scaffold; and (b) an emulsion comprising a population of perfluorocarbon (PFC) droplets comprising a therapeutic agent in the interior thereof, said population of PFC droplets comprising a first subpopulation of PFC droplets with a first mean droplet diameter and a second subpopulation of PFC droplets with a second mean droplet diameter; said first subpopulation of PFC droplets having the property of vaporizing at a first ultrasound frequency and/or acoustic pressure threshold, and said second subpopulation of PFC droplets having the property of vaporizing at a second ultrasound frequency and/or acoustic pressure threshold. In one embodiment, said first ultrasound frequency and/or acoustic pressure threshold and said second ultrasound frequency and/or acoustic pressure threshold are different. In another embodiment, said first ultrasound frequency and/or acoustic pressure threshold and said second ultrasound frequency and/or acoustic pressure threshold are the same.

Emulsions, in additional embodiments, further comprise a surfactant which stabilizes the emulsion. The surfactant stabilizing the primary emulsion (i.e. water-in-PFC) is a triblock copolymer, including but not limited to a perfluoroether and polyethylene glycol. The surfactant stabilizing the secondary emulsion (i.e. water-in-PFC-in-water) is an aqueous soluble surfactant, including but not limited to proteins, lipids, ionic copolymers, and non-ionic copolymers.

Ultrasound Parameters

The disclosure contemplates that various ultrasound parameters are utilized in the practice of the methods disclosed herein. Thus, parameters including but not limited to frequency, peak rarefactional pressure (e.g., from about 1 to about 10 Megapascals (MPa)), pulse repetition frequency (e.g., from about 1 to about 50 Hz), and the number of cycles (e.g., from about 1 to about 100) per pulse are contemplated for use according to the methods described herein.

As described above, the disclosure contemplates that ultrasound frequencies between about 0.5 MHz and about 50 MHz, or from about 1 MHz to about 10 MHz, are useful in the devices and methods disclosed herein to enable efficient vaporization of the droplets. The disclosure contemplates that ultrasound pulse repetition frequencies (i.e., the number of ultrasound pulses per unit time) between about 1 Hertz (Hz) and about 50 Hz are useful in the devices and methods disclosed herein. This range of pulse repetition frequencies will enable efficient droplet vaporization while minimizing the likelihood of unwanted mechanical or thermal bioeffects caused by the ultrasound exposure. Also contemplated are embodiments in which the ultrasound pulse repetition frequency is about 5 Hz, about 10 Hz, about 15 Hz, about 20 Hz, about 25 Hz, about 30 Hz, about 35 Hz, about 40 Hz, or about 45 Hz. Further contemplated by the disclosure are embodiments in which the ultrasound pulse repetition frequency is at least 5 Hz, at least 10 Hz, at least 15 Hz, at least 20 Hz, at least 25 Hz, at least 30 Hz, at least 35 Hz, at least 40 Hz, or at least 45 Hz.

PFC Droplet Size

PFC droplet size contributes to the properties of the tissue scaffold. For example, the vaporization threshold is generally dependent on droplet size, where large droplets vaporize more readily than small droplets. Four factors are important with respect to the diameter of the PFC droplets. First, a larger diameter droplet is desired if maximum loading of the therapeutic agent is desired. Second, the droplet must be able to retain the therapeutic agent in the absence of ADV. Third, following ADV, maximum droplet vaporization and release of the therapeutic agent is desired. Fourth, the droplet diameter must be such that relevant pore sizes are created in the scaffold, either before or after ADV, to allow for invasion of fluid and/or cells. Contrary to general knowledge in the art, and unexpectedly, it is disclosed and exemplified herein that larger diameter PFC droplets (about 100 μm and above) performed better with respect to the aforementioned four factors than did smaller (less than about 100 μm) droplets. Nonetheless, the disclosure contemplates that, in some embodiments, PFC droplets less than 100 μm are utilized. As described herein, the ease of vaporizability is directly related to droplet size.

The average diameter of a PFC droplet for use in the devices and methods of the disclosure are contemplated to be between from about 0.1 μm to about 600 μm. In further embodiments, the average diameter of a PFC droplet is from about 20 μm to about 600 μm. The average droplet diameter and droplet size distribution can be determined using various techniques known in the art, such as optical microscopy, Coulter counter, and light scattering. Different droplet diameters can be obtained by varying the surfactant concentration or the amount of shear force applied to generate the primary or secondary emulsions. In various embodiments, the diameter of a PFC droplet is from about 0.1 μm to about 500 μm, or from about 0.1 μm to about 400 μm, or from about 0.1 μm to about 300 μm, or from about 0.1 μm to about 200 μm, or from about 0.1 μm to about 100 μm, or from about 1 μm to about 500 μm, or from about 1 μm to about 400 μm, or from about 1 μm to about 300 μm, or from about 1 μm to about 200 μm, or from about 1 μm to about 100 μm, or from about 10 μm to about 500 μm, or from about 10 μm to about 400 μm, or from about 10 μm to about 300 μm, or from about 10 μm to about 200 μm, or from about 10 μm to about 100 μm, or from about 50 μm to about 500 μm, or from about 50 μm to about 400 μm, or from about 50 μm to about 300 μm, or from about 50 μm to about 200 μm, or from about 50 μm to about 100 μm. In further embodiments, the diameter of a PFC droplet is from about 0.1 μm to about 50 μm, or from about 0.1 μm to about 75 μm, or from 0.1 μm to about 100 μm, or from 0.1 μm to about 200 μm, or from about 0.1 μm to about 300 μm, or from about 20 μm to about 50 μm, or from about 20 μm to about 75 μm, or from 20 μm to about 100 μm, or from 20 μm to about 200 μm, or from about 20 μm to about 300 μm. In yet further embodiments, the diameter of a PFC droplet is from about 0.1 μm and up to about 10 μm, 20 μm, 25 μm, 30 μm, 35 μm, 40 μm, 45 μm, 50 μm, 55 μm or 60 μm. In additional embodiments, the diameter of a PFC droplet is from about 100 μm and up to about 150 μm, 200 μm, 250 μm, 300 μm, 350 μm, 400 μm, 450 μm, 500 μm, 550 μm or 600 μm. In specific embodiments, the diameter of a PFC droplet is about 0.1 μm, 0.2 μm, 0.3 μm, 0.4 μm, 0.5 μm, 0.6 μm, 0.7 μm, 0.8 μm, 0.9 μm, 1 μm, 1.5 μm, 2 μm, 5 μm, 10 μm, 15 μm, 20 μm, 50 μm, 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm or more.

In still further embodiments, the diameter of a PFC droplet is at least 0.1 μm, at least 0.2 μm, at least 0.3 μm, at least 0.4 μm, at least 0.5 μm, at least 0.6 μm, at least 0.7 μm, at least 0.8 μm, at least 0.9 μm, at least 1 μm, at least 1.5 μm, at least 2 μm, at least 5 μm, at least 10 μm, at least 15 μm, at least 20 μm, at least 50 μm, at least 100 μm, at least 110 μm, at least 120 μm, at least 130 μm, at least 140 μm, at least 150 μm, at least 160 μm, at least 170 μm, at least 180 μm, at least 190 μm, at least 200 μm, at least 210 μm, at least 220 μm, at least 230 μm, at least 240 μm, at least 250 μm, at least 260 μm, at least 270 μm, at least 280 μm, at least 290 μm, at least 300 μm, at least 310 μm, at least 320 μm, at least 330 μm, at least 340 μm, at least 350 μm, at least 360 μm, at least 370 μm, at least 380 μm, at least 390 μm, at least 400 μm, at least 410 μm, at least 420 μm, at least 430 μm, at least 440 μm, at least 450 μm, at least 460 μm, at least 470 μm, at least 480 μm, at least 490 μm, at least 500 μm, at least 510 μm, at least 520 μm, at least 530 μm, at least 540 μm, at least 550

μm, at least 560 μm, at least 570 μm, at least 580 μm, at least 590 μm, at least 600 μm or more.

Volume Fraction

Like PFC droplet size, volume fraction also contributes to the properties of the tissue scaffold. As used herein, "volume fraction" refers to the fraction of the tissue scaffold that is taken up by PFC emulsion. By way of example, a tissue scaffold that contains 1 volume PFC emulsion in 100 total volumes is equal to a 1% volume fraction. Volume fraction is quantitated as a volume: volume measure.

It is disclosed herein that as the volume fraction of the tissue scaffold decreases, certain properties of the gel improve. As exemplified herein, the release of therapeutic agent following ADV is increased approximately 5-fold when a 1% volume fraction is used versus a 10% volume fraction. Quantitation of the release of the therapeutic agent is dependent on the therapeutic agent and methods for such quantitation are well known in the art.

It is contemplated, however, that a volume fraction of between about 0.1% to about 20% is used in the devices and methods of the disclosure. In various embodiments, a volume fraction of between about 0.1% to about 10%, or about 0.1% to about 5%, or about 0.5% to about 10%, or about 1% to about 10%, or about 1% to about 5%, or about 1% to about 15%, or about 1% to about 3%, or about 0.5% to about 5%, or about 1% to about 20% is used in the devices and methods of the disclosure. In specific embodiments, a volume fraction of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more may be used in the devices and methods of the disclosure.

In further embodiments, a volume fraction of at least 0.1%, at least 0.2%, at least 0.3%, at least 0.4%, at least 0.5%, at least 0.6%, at least 0.7%, at least 0.8%, at least 0.9%, 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20% or more is used in the devices and methods of the disclosure.

Gases

The disclosure also provides embodiments wherein the device comprises a gas. In a specific embodiment, the device comprises oxygen. In another embodiment, the device comprises nitric oxide (NO).

Methods of increasing the viability of a cell are provided by the disclosure, comprising the step of administering a tissue scaffold to a patient in need thereof, wherein the scaffold comprises PFC droplets comprising oxygen in the interior thereof. In some embodiments, a host cell, which is able to migrate to the interior of the scaffold, finds itself in an environment of relative hypoxia. Release of oxygen by exposing the PFC droplets comprising oxygen to ultrasound relieves the hypoxic environment and increases the viability of the cell.

Therapeutic Agents

The present disclosure provides devices that comprise therapeutic agents. "Therapeutic agent," "drug" or "active agent" as used herein means any compound useful for therapeutic or diagnostic purposes. The terms as used herein are understood to mean any compound that is administered to a patient for the treatment or diagnosis of a condition.

Therapeutic agents contemplated for use in the devices and methods of the disclosure include hydrophilic and hydrophobic agents. In various embodiments, the therapeutic agent is selected from the group consisting of a polypeptide, a peptide, a polynucleotide, a viral particle, a gas, a contrast agent, a small molecule, a carbohydrate and an aminoglycoside. Therapeutic agents also include, without limitation, metallic salts, oxides and/or ions.

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety.

Polypeptides

As used herein a "polypeptide" refers to a polymer comprised of amino acid residues. In some aspects of the disclosure, a device comprises a polypeptide as described herein. Polypeptides are understood in the art and include without limitation an antibody, an enzyme and a hormone.

Polypeptides of the present disclosure may be either naturally occurring or non-naturally occurring.

Naturally occurring polypeptides include without limitation biologically active polypeptides (including antibodies) that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short polypeptides.

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physicochemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

As discussed hereinabove, polypeptides include antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor a1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor (3, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, WNT ligands, and chimeric proteins and biologically or immunologically active fragments thereof. Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

As described by the present disclosure, in some aspects therapeutic agents include small molecules. The term "small molecule," as used herein, refers to a chemical compound, for instance a peptidometic, that may optionally be derivatized, or any other low molecular weight organic compound, either natural or synthetic. Such small molecules may be a therapeutically deliverable substance or may be further derivatized to facilitate delivery. In some embodiments, a small molecule is a vitamin.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/ equivalents; antiandrogens such as flutamide, gonadotropin-releasing hormone analogs and leuprolide; and non-steroidal antiandrogens such as flutamide.

The term "antibiotic agent" as used herein means any of a group of chemical substances having the capacity to inhibit the growth of, or to kill bacteria, and other microorganisms, used chiefly in the treatment of infectious diseases or as a prophylactic to prevent infection. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Polynucleotides

Polynucleotides contemplated by the present disclosure include DNA, RNA, modified forms and combinations thereof as defined herein. Accordingly, in some aspects, the device comprises DNA. In some embodiments, the DNA is double stranded, and in further embodiments the DNA is single stranded. In further aspects, the device comprises RNA, and in still further aspects the device comprises double stranded RNA, and in a specific embodiment, the double stranded RNA is a small interfering RNA (siRNA) or a microRNA (miRNA). The term "RNA" includes duplexes of two separate strands, as well as single stranded structures. Single stranded RNA also includes RNA with secondary structure. In one aspect, RNA having a hairpin loop is contemplated.

When a device comprises a plurality of polynucleotides, the polynucleotide is, in some aspects, comprised of a sequence that is sufficiently complementary to a target sequence of a polynucleotide such that hybridization of the polynucleotide that is part of the device and the target polynucleotide takes place. The polynucleotide in various aspects is single stranded or double stranded, as long as the double stranded molecule also includes a single strand sequence that hybridizes to a single strand sequence of the target polynucleotide.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Modified nucleic acids also include peptide nucleic acids (PNAs) as well as locked nucleic acids (LNAs), each of which is known in the art.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

A polynucleotide of the disclosure, or a modified form thereof, is generally from about 5 nucleotides to about 100 nucleotides in length. More specifically, devices comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Plasmids and viral particles, which may comprise expressible coding regions for a protein of interest, are also contemplated by the disclosure. Thus, nucleic acids greater than 100 nucleotides are contemplated. In some embodiments, nucleic acids that are 200, 500, 1000, 2000, 3000, 4000, 5000, 10,000 or more nucleotides in length are contemplated. A protein of interest is any polypeptide that is useful as a therapeutic for a disease condition. A viral particle may comprise a polynucleotide and/or a polypeptide and/or a lipid. A toxin (e.g., a neurotoxin, hemotoxin, cytotoxin and/or necrotoxin), which may in some embodiments comprise a polypeptide, are contemplated for use as a therapeutic agent.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. No. 5,270,163, and 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

Carbohydrates and Aminoglycosides

Carbohydrates contemplated for use according to the disclosure include heparin (high molecular weight and low molecular weight), monosaccharides (e.g., glucose, glucosamine, sialic acid), disaccharides (e.g., maltose, trehalose), and polysaccharides (e.g., starch, glycogen, cellulose, chitin).

Aminoglycosides contemplated by the disclosure include, without limitation, antibiotics (e.g., amikacin, arbekacin, gentamicin, kanamycin, neomycin, netilmicin, paromomycin, rhodostreptomycin, streptomycin, tobramycin, and apramycin).

Contrast Agents/Detectable Markers

In some embodiments, the devices of the present disclosure comprise a contrast agent. The contrast agent, in various embodiments, is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

In further embodiments, a device of the disclosure comprises a detectable marker or label. It will be understood that a label contemplated by the disclosure includes any of the fluorophores described herein as well as other detectable labels known in the art. For example, labels also include, but are not limited to, chemiluminescent molecules, radioactive labels, dyes, fluorescent molecules, phosphorescent molecules, and contrast agents as described above.

Suitable fluorescent molecules are well known in the art and include without limitation 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

It will also be understood that the detectable markers and/or labels disclosed herein may be used alone, or they may be attached to a therapeutic agent of the disclosure. Methods of attaching a marker or label to a therapeutic agent as disclosed herein are known in the art.

It is also contemplated by the disclosure that, in some aspects, fluorescent polypeptides are used. Any detectable polypeptide known in the art is useful in the methods of the disclosure, and in some aspects is a fluorescent protein including, but not limited to, green fluorescent protein.

Methods

In some aspects, the disclosure provides a method of treating a patient in need of tissue expansion comprising administering a device as disclosed herein to the individual. In some aspects, the device is for use in plastic and reconstructive surgeries.

The methods of the disclosure generally comprise the steps of preparing a tissue scaffold, delivering the tissue scaffold to one or more sites of interest and exposing the tissue scaffold to ultrasound.

In general, the disclosure provides a device comprising a tissue scaffold and a PFC emulsion. The tissue scaffold, in some embodiments, comprises one or more proteins that, when mixed, polymerize to form the scaffold. As an alternative, a commercially available hydrogel scaffold may be used in the methods provided herein. In a specific embodiment, a tissue scaffold is produced using fibrinogen and thrombin, which are separately reconstituted from a powder. Thus, in some embodiments the tissue scaffold is produced by mixing fibrinogen and thrombin to achieve a given protein density within the scaffold. The reconstituted proteins are then mixed with PFC droplets, which are produced according to published protocols (see, e.g., [Fabiilli et al., Pharm Res. 27(12): 2753-2765 (2010) and Fabiilli et al., U.S. Patent Application Publication Number 20130330389], each of which is incorporated herein by reference in their entireties).

By way of example, a mixture comprising an in situ-polymerizable, biodegradable hydrogel scaffold, such as fibrin, and a PFC emulsion is injected at the site of damaged or diseased tissue. Additional routes of administration are contemplated, and are described herein below. Administration of a device is contemplated to occur 1, 2, 3, 4, 5, 6, 7, 8, 9, 10 or more times each, at one or more sites of an individual. Thus, repeat administration of the device is contemplated. Administration of more than one device is also contemplated.

The hydrogel scaffold polymerizes within minutes and serves to localize the acoustically- and/or temperature-sensitive emulsion at the implantation site. It is also contemplated that the scaffold is allowed to polymerize ex vivo and is subsequently implanted at a site of interest. As discussed hereinabove, the rate of polymerization of the scaffold can be controlled.

In some embodiments, ultrasound is then applied transcutaneously (i.e., non-invasively) to actively control vaporization of the emulsion within the implant to modulate the scaffold porosity and/or stiffness/viscoelasticity to achieve tissue expansion. In one embodiment, the ultrasound is applied to the device a single time, and at a single frequency. In further embodiments, the ultrasound is applied 2, 3, 4, 5, 6, 7, 8, 9, 10 or more times, at one or more frequencies.

In additional embodiments, diagnostic ultrasound is used to provide real-time feedback of changes in porosity. Ultrasound-induced changes in scaffold structure may also accelerate degradation and/or increase the mechanical properties (i.e., stiffness) of the hydrogel scaffold. Ultrasound-induced vaporization also facilitates scaffold degradation by promoting cellular in-growth into the scaffold, and can change the form factor (i.e., the shape and/or dimensions) of the scaffold post-implantation. A compelling feature of such embodiments is that ultrasound-induced vaporization results in structural modifications of the hydrogel scaffold can be restricted to subvolumes of the implant exposed to ultrasound.

Devices of the disclosure are contemplated for use in any patient in need of tissue expansion. For example and without limitation, tissue expansion has been used by surgeons to overcome clinical problems of surgical defects, such as replacing lost or surgically excised tissue with neighboring tissue of similar color, texture, sensation, and thickness; retaining the hair-bearing capability and avoiding remote donor site. Compression of underlying nerves, major blood vessels, and the trachea during the expansion process has not proven to be a problem. The treatment of alopecia has been revolutionized, and the ability to treat other cutaneous defects of the head and neck has been greatly improved using tissue expansion techniques. A device of the disclosure is also contemplated for use in plastic and reconstructive surgeries including breast reconstruction and burn surgery.

The success of bone augmentation, for example of the alveolar ridge, might be endangered by dehiscence of the soft tissue that covers the augmented bone. Soft-tissue coverage can be achieved without tension through pre-augmentation tissue expansion with hydrogel expanders.

Resorbable hydrogels can be used in cleft palate repair through the expansion of tissue implanted in the first stage of treatment. The hydrogels can also be used for scar reconstruction following trauma, burns or cancer surgery. The disclosure also contemplates the treatment of congenital craniofacial conditions and limb deformities. Further, the devices of the present disclosure also find application in restorative dentistry.

Further applications of a device provided by the instant disclosure include:
Post burn reconstruction
Post trauma reconstruction
Reconstruction of congenital or acquired defects of the scalp, face, ear, neck, trunk, breast, upper limb/extremity, and lower limb/extremity
Scalp reconstruction for alopecia
Skin reconstruction following removal of congenital nevus or hemangioma
Breast reconstruction for defects resulting from mastectomy or lumpectomy
Tissue reconstruction following surgical resection
Expansion of the eye socket and orbit for congenital anophthalmia
Wound repair in diabetic patients
Facial and breast asymmetry
Rhinoplasty
Nasoalveolar molding for treatment of conditions such as cleft lip, alveolus, or palate
Reconstructive urology for bladder augmentation, ureteral dilation for the generation of indigenous tissue and subsequent ureterocystoplasties, ureteral elongation, and dilation of the renal pelvis, producing native tissue for the reconstruction of defects or strictures of the upper ureter.

Dosing and Administration

The device can be administered by any route that permits treatment of, for example and without limitation, a disease, disorder or infection as described herein. For example, in some embodiments, the device is injected at a desired site of skin growth in a subject. Additionally, the device may be delivered to a patient using any standard route of administration, including parenterally, such as intra-articularly, intraperitoneally, intrapulmonary, subcutaneously or intramuscularly, intrathecally, topically, as an aerosol, rectally, nasally or by inhalation. Additionally, a device as disclosed herein may be implanted at a site of interest, which can in various embodiments be a site of tissue injury or disease.

Administration may take the form of single dose administration, or the device of the embodiments can be administered over a period of time in divided doses. Also contemplated is the administration of more than one device, either concurrently or separately over a period of time, wherein each device comprises one or more populations of PFC droplets. However the device of the embodiments are administered to the subject, the amounts of device administered and the route of administration chosen should be selected to permit efficacious treatment of the disease condition.

Kits

Also provided are kits comprising a device of the disclosure. In one embodiment, the kit comprises at least one container, the container holding at least one type of device as described herein. The container optionally includes one or more additional type of devices.

In another embodiment, the kit comprises at least two containers. The first container holds a protein used to formulate the tissue scaffold. The second container holds one or more proteins that interact with the protein in the first container to trigger polymerization of the tissue scaffold. In further embodiments, the kit comprises a third container comprising an emulsion as described herein.

In each embodiment, the kit optionally includes instructions, each container contains a label, the kit itself includes a label, and the kit optionally includes one or more devices for use as controls.

REFERENCES

Ammi A Y, Cleveland R O, Mamou J, Wang G I, Bridal S L, O'Brien W D. Ultrasonic contrast agent shell rupture detected by inertial cavitation and rebound signals. Ieee Transactions on Ultrasonics Ferroelectrics and Frequency Control 2006; 53:126-36.

Apfel R E. POSSIBILITY OF MICROCAVITATION FROM DIAGNOSTIC ULTRASOUND. Ieee Transactions on Ultrasonics Ferroelectrics and Frequency Control 1986; 33:139-42.

Apfel R E, Holland C K. Gauging the likelihood of cavitation from short-pulse, low-duty cycle diagnostic ultrasound. Ultrasound in Medicine and Biology 1991; 17:179-85.

Atchley A A, Frizzell L A, Apfel R E, Holland C K, Madanshetty S, Roy R A. Thresholds for Cavitation Produced in Water by Pulsed Ultrasound. Ultrasonics 1988; 26:280-5.

Barthes J, Ozcelik H, Hindie M, Ndreu-Halili A, Hasan A, Vrana N E. Cell Microenvironment Engineering and Monitoring for Tissue Engineering and Regenerative Medicine: The Recent Advances. Biomed Research International 2014;

Bos P K, van Osch G J V M, Frenz D A, Verhaar J A N, Verwoerd-Verhoef H L. Growth factor expression in cartilage wound healing: temporal and spatial immunolocalization in a rabbit auricular cartilage wound model. Osteoarthritis and Cartilage 2001; 9:382-9.

Brennen C E. Fission of collapsing cavitation bubbles. Journal of Fluid Mechanics 2002; 472:153-66.

Chen W S, Matula T J, Brayman A A, Crum L A. A comparison of the fragmentation thresholds and inertial cavitation doses of different ultrasound contrast agents. Journal of the Acoustical Society of America 2003; 113: 643-51.

Chen W S, Matula T J, Crum L A. The disappearance of ultrasound contrast bubbles: Observations of bubble dissolution and cavitation nucleation. Ultrasound Med Biol 2002; 28:793-803.

Dayton P A, Morgan K E, Klibanov A L, Brandenburger G H, Ferrara K W. Optical and acoustical observations of the effects of ultrasound on contrast agents. Ieee Transactions on Ultrasonics Ferroelectrics and Frequency Control 1999; 46:220-32.

Dehghani F, Annabi N. Engineering porous scaffolds using gas-based techniques. Current Opinion in Biotechnology 2011; 22:661-6.

Dias A M A, Freire M, Coutinho J A P, Marrucho I M. Solubility of oxygen in liquid perfluorocarbons. Fluid Phase Equilibria 2004; 222:325-30.

Diaz-Lopez R, Tsapis N, Fattal E. Liquid perfluorocarbons as contrast agents for ultrasonography and 19F-MRI. Pharmaceutical Research 2010; 27:1-16.

Epstein P S, Plesset M S. On the stability of gas bubbles in liquid-gas solutions. Journal of Chemical Physics 1950; 18:1505-9.

Epstein-Barash H, Orbey G, Polat B E, Ewoldt R H, Feshitan J, Langer R, Borden M A, Kohane D S. A microcomposite hydrogel for repeated on-demand ultrasound-triggered drug delivery. Biomaterials 2010; 31:5208-17.

Fabiilli M L, Haworth K J, Fakhri N H, Kripfgans O D, Carson P L, Fowlkes J B. The role of inertial cavitation in acoustic droplet vaporization. IEEE Trans Ultrason Ferroelectr Freq Control 2009; 56:1006-17.

Fabiilli M L, Lee J A, Kripfgans O D, Carson P L, Fowlkes J B. Delivery of water-soluble drugs using acoustically triggered perfluorocarbon double emulsions. Pharm Res 2010; 27:2753-65.

Fabiilli M L, Wilson C G, Padilla F, Martin-Saavedra F M, Fowlkes J B, Franceschi R T. Acoustic droplet-hydrogel composites for spatial and temporal control of growth factor delivery and scaffold stiffness. Acta Biomaterialia 2013.

Faithfull N S. Oxygen Delivery From Fluorocarbon Emulsions—Aspects Of Convective And Diffusive Transport. Biomaterials Artificial Cells and Immobilization Biotechnology 1992; 20:797-804.

Ferrara K W, Pollard R, Borden M A. Ultrasound microbubble contrast agents: fundamentals and application to gene and drug delivery. Annual Review of Biomedical Engineering 2007; 9:425-47.

Flynn H G, Church C C. A Mechanism For The Generation Of Cavitation Maxima By Pulsed Ultrasound. Journal of the Acoustical Society of America 1984; 76:505-12.

Fowlkes J B, Crum L A. Cavitation Threshold Measurements For Microsecond Length Pulses Of Ultrasound. Journal of the Acoustical Society of America 1988; 83:2190-201.

Frimpong R A, Fraser S, Hilt J Z. Synthesis and temperature response analysis of magnetic-hydrogel nanocomposites. Journal of Biomedical Materials Research Part A 2007; 80A:1-6.

Fujie T, Mori Y, Ito S, Nishizawa M, Bae H, Nagai N, Onami H, Abe T, Khademhosseini A, Kaji H. Micropatterned Polymeric Nanosheets for Local Delivery of an Engineered Epithelial Monolayer. Advanced Materials 2014; 26:1699-705.

Giesecke T, Hynynen K. Ultrasound-mediated cavitation thresholds of liquid perfluorocarbon Droplets\textitin vitro. Ultrasound in Medicine and Biology 2003; 29:1359-65.

Hallow D M, Mahajan A D, McCutchen T E, Prausnitz M R. Measurement and correlation of acoustic cavitation with cellular bioeffects. Ultrasound in Medicine and Biology 2006; 32:1111-22.

Holland C K, Apfel R E. An improved theory for the prediction of microcavitation thresholds. IEEE Transactions on Ultrasonics, Ferroelectrics, and Frequency Control 1989; 36:204-8.

Huebsch N, Kearney C J, Zhao X H, Kim J, Cezar C A, Suo Z G, Mooney D J. Ultrasound-triggered disruption and self-healing of reversibly cross-linked hydrogels for drug delivery and enhanced chemotherapy. Proceedings of the National Academy of Sciences of the United States of America 2014; 111:9762-7.

Hwang J H, Tu J, Brayman A A, Matula T J, Crum L A. Correlation between inertial cavitation dose and endothelial cell damage in vivo. Ultrasound in Medicine and Biology 2006; 32:1611-9.

Javadi M, Pitt W G, Tracy C M, Barrow J R, Willardson B M, Hartley J M, Tsosie N H. Ultrasonic gene and drug delivery using eLiposomes. Journal of Controlled Release 2013; 167:92-100.

Johnson J L H, Dolezal M C, Kerschen A, Matsunaga T O, Unger E C. In vitro comparison of dodecafluoropentane (DDFP), perfluorodecalin (PFD), and perfluoroctylbromide (PFOB) in the facilitation of oxygen exchange. Artificial cells, blood substitutes, and biotechnology 2009; 37:156-62.

Kandadai M A, Mohan P, Lin G, Butterfield A, Skliar M, Magda J J. Comparison of surfactants used to prepare aqueous perfluoropentane emulsions for pharmaceutical applications. Langmuir 2010; 26:4655-60.

Kawabata K-I, Sugita N, Yoshikawa H, Azuma T, Umemura S-I. Nanoparticles with Multiple Perfluorocarbons for Controllable Ultrasonically Induced Phase Shifting. Japanese Journal of Applied Physics 2005; 44:4548-52.

Kniazeva E, Kachgal S, Putnam A J. Effects of Extracellular Matrix Density and Mesenchymal Stem Cells on Neovascularization In Vivo. Tissue Engineering Part A 2011; 17:905-14.

Kripfgans O D, Fabiilli M L, Carson P L, Fowlkes J B. On the acoustic vaporization of micrometer-sized droplets. J Acoust Soc Am 2004; 116:272-81.

Kripfgans O D, Fowlkes J B, Miller D L, Eldevik O P, Carson P L. Acoustic droplet vaporization for therapeutic and diagnostic applications. Ultrasound in Medicine and Biology 2000; 26:1177-89.

Kulkarni R, Biswanath S. Electrically responsive smart hydrogels in drug delivery: a review. Journal of Applied Biomaterials and Biomechanics 2007; 5:125-39.

Lavigne M D, Pennadam S S, Ellis J, Yates L L, Alexander C, Gorecki D C. Enhanced gene expression through temperature profile-induced variations in molecular architecture of thermoresponsive polymer vectors. The Journal of Gene Medicine 2007; 9:44-54.

Lima E G, Durney K M, Sirsi S R, Nover A B, Ateshian G A, Borden M A, Hung C T. Microbubbles as biocompatible porogens for hydrogel scaffolds. Acta Biomaterialia 2012 (in press): Madanshetty S I, Apfel R E. Acoustic Microcavitation—Enhancement And Applications. Journal of the Acoustical Society of America 1991; 90:1508-14.

Marchioni C, Riccardi E, Spinelli S, dell'Unto F, Grimaldi P, Bedini A, Giliberti C, Giuliani L, Palomba R, Castellano A C. Structural changes induced in proteins by therapeutic ultrasounds. Ultrasonics 2009; 49:569-76.

Martz T D, Sheeran P S, Bardin D, Lee A P, Dayton P A. Precision Manufacture of Phase-Change Perfluorocarbon Droplets Using Microfluidics. Ultrasound in Medicine and Biology 2011; 37:1952-7.

Matsusaki M, Akashi M. Novel functional biodegradable polymer IV: pH-Sensitive controlled release of fibroblast growth factor-2 from a poly(gamma-glutamic acid)-sulfonate matrix for tissue engineering. Biomacromolecules 2005; 6:3351-6.

Meijering B D M, Henning R H, Van Gilst W H, Gavrilovic I, Van Wamel A, Deelman L E. Optimization of ultrasound and microbubbles targeted gene delivery to cultured primary endothelial cells. Journal of Drug Targeting 2007; 15:664-71.

Metallo C M, Mohr J C, Detzel C J, de Pablo J J, Van Wie B J, Palecek S P. Engineering the stem cell microenvironment. Biotechnology Progress 2007; 23:18-23.

Nair A, Thevenot P, Dey J, Shen J H, Sun M W, Yang J, Tang L P. Novel Polymeric Scaffolds Using Protein Microbubbles as Porogen and Growth Factor Carriers. Tissue Engineering Part C-Methods 2010; 16:23-32.

Ohl C-D, Arora M, Ikink R, de Jong N, Versluis M, Delius M, Lohse D. Sonoporation from jetting cavitation bubbles. Biophysical Journal 2006; 91:4285-95.

Pishchalnikov Y A, McAteer J A, Pishchalnikova I V, Williams J C, Bailey M R, Sapozhnikov O A. Bubble proliferation in shock wave lithotripsy occurs during inertial collapse. In: Enflo B O, Hedberg C M, Kari L, ed. Nonlinear Acoustics Fundamentals and Applications. 2008. pp. 460-3.

Rahim A, Taylor S L, Bush N L, Ter Haar G R, Bamber J C, Porter C D. Physical parameters affecting ultrasound/microbubble-mediated gene delivery efficiency in vitro. Ultrasound in Medicine and Biology 2006a; 32:1269-79.

Rahim A A, Taylor S L, Bush N L, ter Haar G R, Bamber J C, Porter C D. Spatial and acoustic pressure dependence of microbubble-mediated gene delivery targeted using focused ultrasound. Journal of Gene Medicine 2006b; 8:1347-57.

Rapoport N, Nam K H, Gupta R, Gao Z G, Mohan P, Payne A, Todd N, Liu X, Kim T, Shea J, Scaife C, Parker D L, Jeong E K, Kennedy A M. Ultrasound-mediated tumor imaging and nanotherapy using drug loaded, block copolymer stabilized perfluorocarbon nanoemulsions. Journal of Controlled Release 2011; 153:4-15.

Rapoport N Y, Kennedy A M, Shea J E, Scaife C L, Nam K-H. Controlled and targeted tumor chemotherapy by ultrasound-activated nanoemulsions/microbubbles. Journal of Controlled Release 2009; 138:268-76.

Riess J G. Oxygen Carriers ("Blood Substitutes")—Raison d'Etre, Chemistry, and Some Physiology. Chemical Reviews 2001; 101:2797-919.

Sakiyama-Elbert S E, Hubbell J A. Controlled release of nerve growth factor from a heparin-containing fibrin-based cell ingrowth matrix. Journal of Controlled Release 2000a; 69:149-58.

Sakiyama-Elbert S E, Hubbell J A. Development of fibrin derivatives for controlled release of heparin-binding growth factors. Journal of Controlled Release 2000b; 65:389-402.

Satyam A, Kumar P, Fan X L, Gorelov A, Rochev Y, Joshi L, Peinado H, Lyden D, Thomas B, Rodriguez B, Raghunath M, Pandit A, Zeugolis D. Macromolecular Crowding Meets Tissue Engineering by Self-Assembly: A Paradigm Shift in Regenerative Medicine. Advanced Materials 2014; 26:3024-34.

Schad K C, Hynynen K. In vitro characterization of perfluorocarbon droplets for focused ultrasound therapy. Physics in Medicine and Biology 2010; 55:4933-47.

Seliktar D. Designing Cell-Compatible Hydrogels for Biomedical Applications. Science 2012; 336:1124-8.

Shaikh F M, Callanan A, Kavanagh E G, Burke P E, Grace P A, McGloughlin T M. Fibrin: A natural biodegradable scaffold in vascular tissue engineering. Cells Tissues Organs 2008; 188:333-46.

Sheeran P S, Wong V P, Luois S, McFarland R J, Ross W D, Feingold S, Matsunaga T O, Dayton P A. Decafluorobutane as a Phase-Change Contrast Agent for Low-Energy Extravascular Ultrasonic Imaging. Ultrasound in Medicine and Biology 2011; 37:1518-30.

Shpak O, Stricker L, Kokhuis T, Luan Y, Fowlkes B, Fabiilli M, Lohse D, de Jong N, Versluis M. Ultrafast dynamics of the acoustic vaporization of phase-change microdroplets. The Journal of the Acoustical Society of America 2013; 133:3586.

Sojo K, Sawaki Y, Hattori H, Mizutani H, Ueda M. Immunohistochemical study of vascular endothelial growth factor (VEGF) and bone morphogenetic protein-2,-4 (BMP-2,-4) on lengthened rat femurs. Journal of Cranio-Maxillofacial Surgery 2005; 33:238-45.

Thornton P D, McConnell G, Ulijn R V. Enzyme responsive polymer hydrogel beads. Chemical Communications 2005; 5913-5.

Tse H T K, Weaver W M, Di Carlo D. Increased Asymmetric and Multi-Daughter Cell Division in Mechanically Confined Microenvironments. Plos One 2012; 7:

Unger E C, Porter T, Culp W, LaBell R, Matsunaga T, Zutshi R. Therapeutic applications of lipid-coated microbubbles. Advanced Drug Delivery Reviews 2004; 56:1291-314.

Vangelder J M, Nair C H, Dhall D P. Effects Of Poloxamer-188 On Fibrin Network Structure, Whole-Blood Clot Permeability And Fibrinolysis. Thrombosis Research 1993; 71:361-76.

Ward M, Wu J R, Chiu J F. Ultrasound-induced cell lysis and sonoporation enhanced by contrast agents. Journal of the Acoustical Society of America 1999; 105:2951-7.

Whelan D, Caplice N M, Clover A J P. Fibrin as a delivery system in wound healing tissue engineering applications. Journal of Controlled Release 2014; 196:1-8.

Wong Z Z, Kripfgans O D, Qamar A, Fowlkes J B, Bull J L. Bubble evolution in acoustic droplet vaporization at physiological temperature via ultra-high speed imaging. Soft Matter 2011; 7:4009-16.

Wu C, Chen C, Lai J, Mu X, Zheng J, Zhao Y. Molecule-scale controlled-release system based on light-responsive silica nanoparticles. Chemical Communications 2008; 23:2662-4.

Zhao X, Kim J, Cezar C A, Huebsch N, Lee K, Bouhadir K, Mooney D J. Active scaffolds for on-demand drug and cell delivery. Proceedings of the National Academy of Sciences of the United States of America 2011; 108:67-72.

EXAMPLES

Example 1

In this example, a mixture containing all of the components required for the hydrogel scaffold, including the perfluorocarbon (PFC) emulsion, is injected at the site of intended tissue/skin expansion. The mixture polymerizes within minutes, thus forming a solid structure at the implantation site. Body heat and scaffold degradation will cause the PFC emulsion to convert from liquid droplets into gas bubbles. The gas bubbles, which remained trapped within the scaffold, will begin to expand due to the diffusion of dissolved gas (e.g., oxygen) within the scaffold and gas present in the extravascular space. Thus, bubble growth leads to expansion of the hydrogel, which causes the overlying tissue/skin to expand (FIG. 1). The PFC emulsion can also be phase transitioned from liquid droplets into gas bubbles using focused ultrasound. This would enable anisotropic expansion of the scaffold by spatially patterning bubble formation within the scaffold as well as scaffold degradation.

In in vitro experiments, it was determined that scaffolds doped with emulsions containing lower boiling point PFCs displayed greater spontaneous (i.e., thermally-induced) vaporization compared to higher boiling point PFCs. In the presented example (FIG. 2), a scaffold doped with a perfluoropentane (PFP, $C_5F_{12}$, 29° C. boiling point) emulsion exhibited greater bubble formation than a scaffold containing a perfluorohexane (PFH, $C_6F_{14}$, 56° C. boiling point) emulsion.

Figure 2:
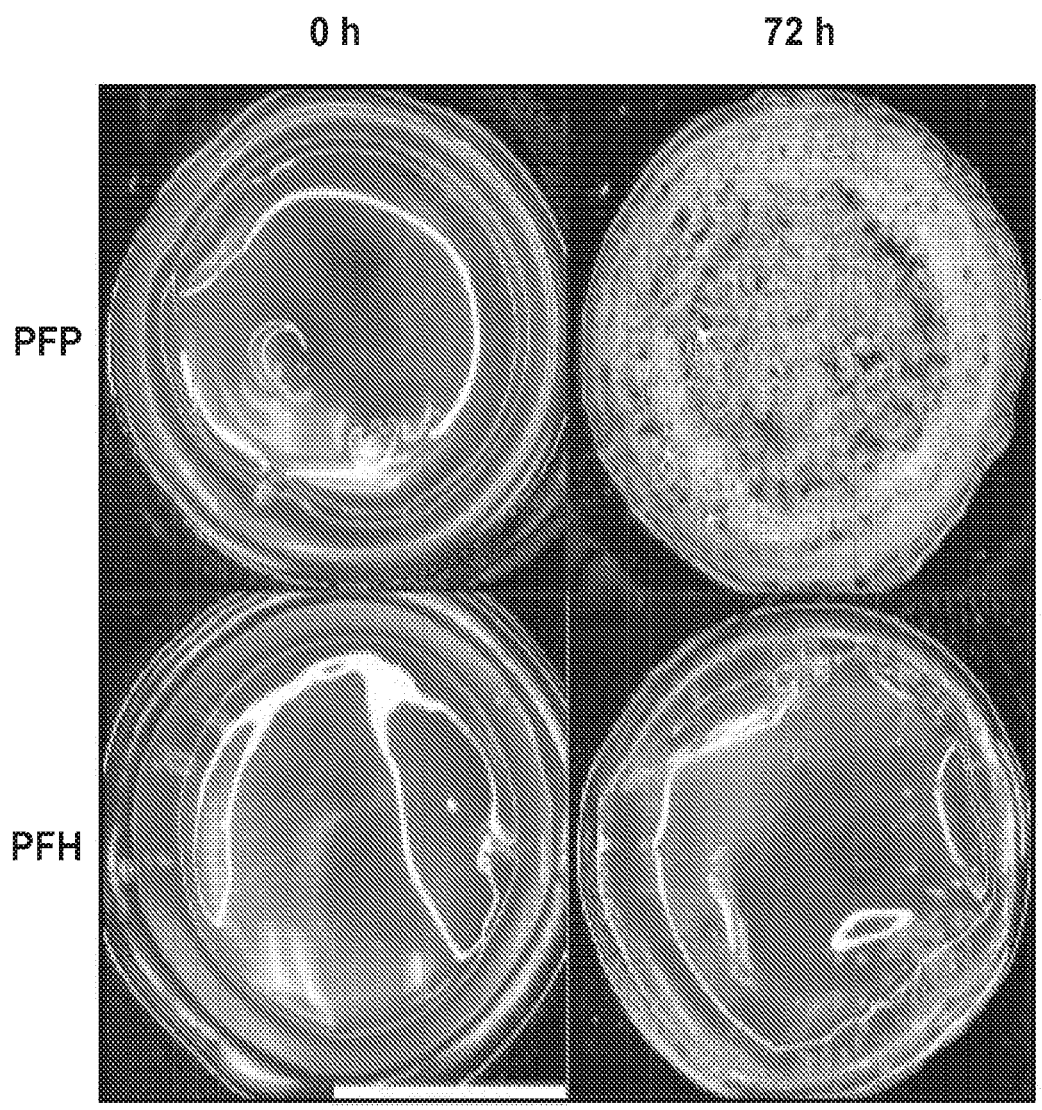
FIG. 2 shows light microscopy images of 5 mg/mL fibrin scaffolds doped with either 1% (v/v) perfluoropentane (PFP) or perfluorohexane (PFH) emulsions at 0 hours and 72 hours after polymerization. Scale bar: 7.8 mm.
Figure 3A:
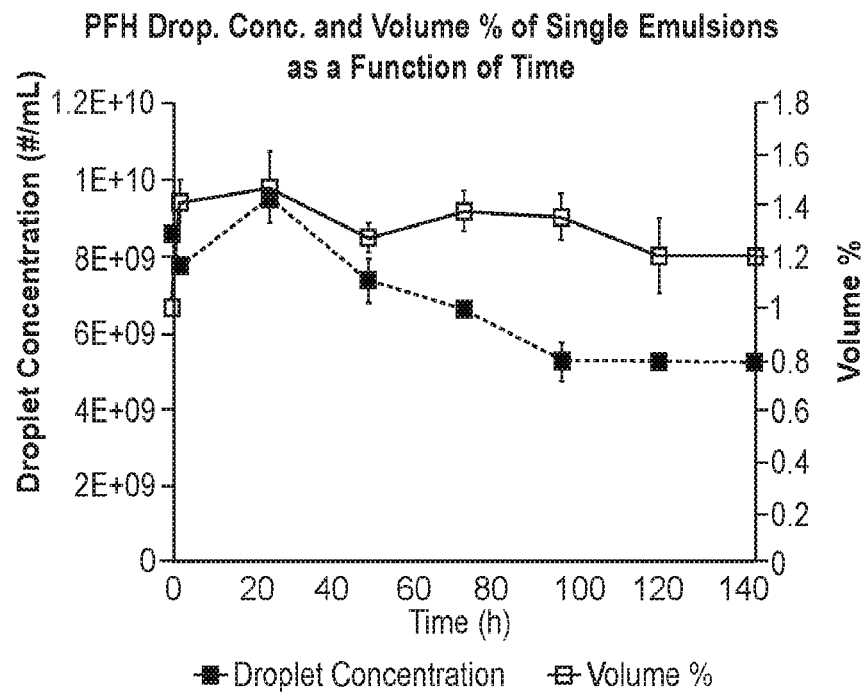
FIGS. 3A and 3B show the thermal conversion of perfluorohexane (PFH, A) or perfluoropentane (PFP, B) emulsions—doped at 1% (v/v)—in 5 mg/mL fibrin scaffolds at 37° C. At each time point, the scaffolds were degraded with trypsin and the remaining droplets were sized/counted with a Coulter Counter.
Figure 3B:
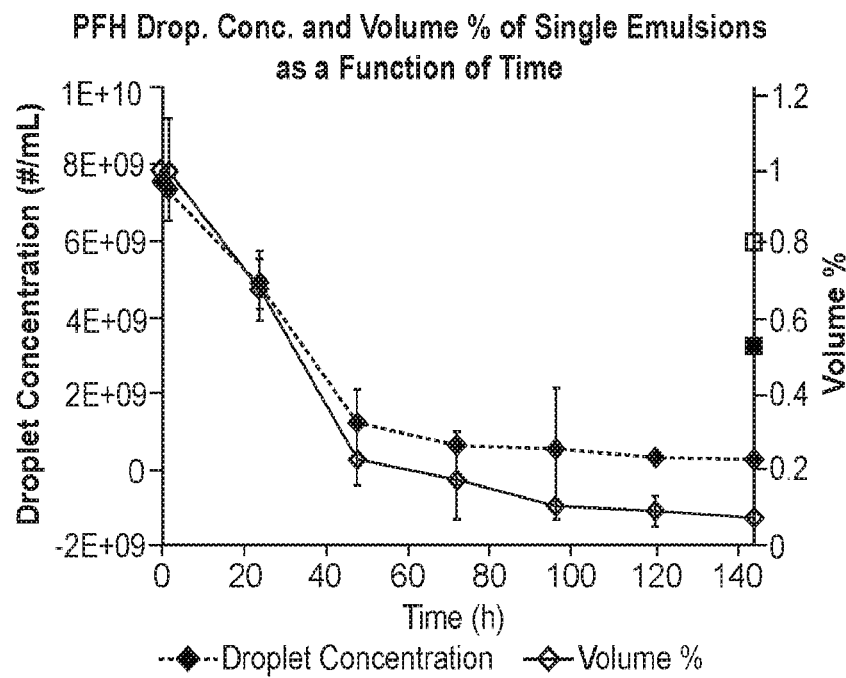

FIG. 2 shows light microscopy images of 5 mg/mL fibrin scaffolds doped with either 1% (v/v) perfluoropentane (PFP) or perfluorohexane (PFH) emulsions at 0 h and 72 h after polymerization. The conversion of PFC droplets to bubbles within a fibrin scaffold was quantified (FIGS. 3A and 3B). Consistent with FIG. 2, PFP droplets (FIG. 3B) are converted to bubbles more easily than PFH droplets (FIG. 3A).

Figure 4:
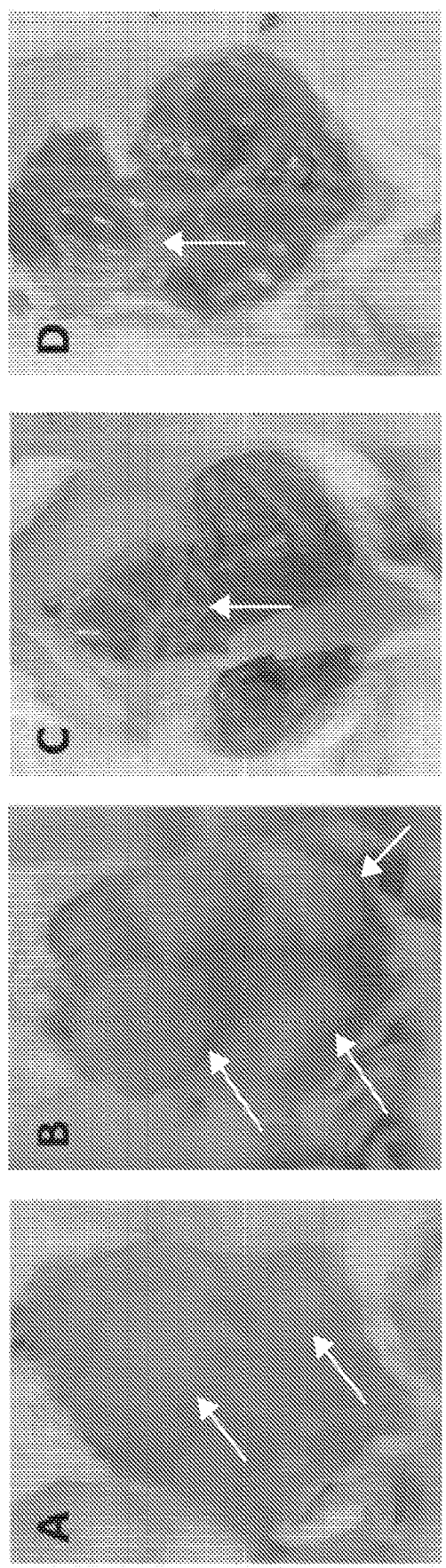
FIG. 4 shows images taken 8 days after implantation of 5 mg/mL fibrin scaffolds doped with 1% (v/v) emulsion in BALB/c mice. The dispersed perfluorocarbon phase within the emulsion consisted of 75% (v/v) perfluoropentane and 25% (v/v) perfluorohexane. Arrows denote the location of tissue expansion.
Figure 5:
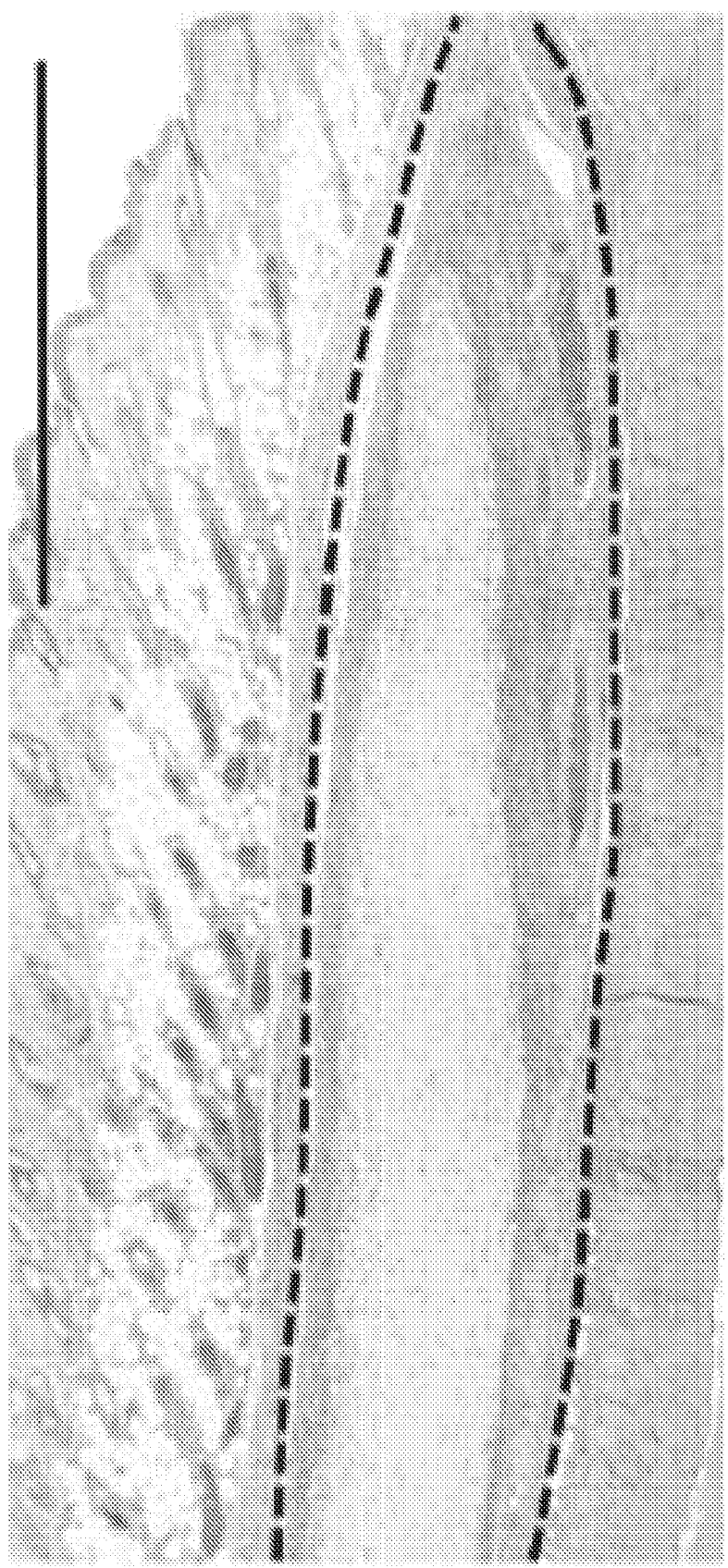
FIG. 5 shows hematoxylin and eosin staining of a histological section of a subcutaneous fibrin scaffold (5 mg/mL) 7 days after implantation beneath the dorsal skin of a BALB/c mouse. The dashed lines indicate the scaffold/tissue interface. Scale bar: 1 mm.

Next, in in vivo experiments, fibrin scaffolds doped with PFC emulsions were implanted subcutaneously in BALB/c mice (FIG. 4). Skin/tissue expansion is clearly evident in the images that were taken 8 days after scaffold implantation. Following in vivo implantation, the scaffold is degraded by cellular infiltration and enzymatic processes. As seen in FIG. 5, cellular infiltration is clearly evident within the scaffold 7 days after implantation. Since fibrin is a naturally-occurring protein, biocompatibility of fibrin scaffolds is very high.

Example 2

Hydrogel scaffolds are used in tissue engineering as a delivery vehicle for regenerative growth factors (GFs). Spatiotemporal patterns of GF signaling are critical for tissue regeneration, yet most scaffolds afford limited control of GF release, especially after implantation. Acoustic droplet vaporization (ADV) can control GF release from a fibrin scaffold doped with a perfluorocarbon emulsion (see, e.g., U.S. Patent Application Publication No. 2013/0330389, incorporated by reference herein in its entirety). This study investigates properties of the acoustically responsive scaffold (ARS) critical for further translation. At 2.5 MHz, ADV and inertial cavitation thresholds ranged from 1.5-3.0 MPa and 2.0-7.0 MPa peak rarefactional pressure, respectively, for ARSs of varying compositions. Viability of C3H10T1/2 cells, encapsulated in the ARS, did not decrease significantly for pressures below 4 MPa. ARSs with perfluorohexane emulsions displayed higher stability versus perfluoropentane emulsions, while surrogate payload release was minimal without ultrasound. These results enable the selection of ARS compositions and acoustic parameters needed for optimized spatiotemporal control.

The in vitro work presented herein on a fibrin-based ARS is divided into three main parts. First, the ADV and IC thresholds were measured for ARSs of varying composition. Parameters such as fibrin density, emulsion formulation (including stabilizing shell, PFC core, and emulsion structure), and acoustic cycles were explored. Second, the viability of cells encapsulated in the ARS was evaluated across the different regimes of ADV and IC. Third, the physical stabilities of the ARSs, including non-selective (i.e., without US exposure) release profiles, were measured over the course of 7 days.

Materials and Methods

Single Emulsion Preparation and Characterization

Four different formulations of single emulsions (PFC/W) were made by combining 25% (v/v) PFP (CAS #: 678-26-2, Strem Chemicals, Newburyport, Mass. USA) or PFH (CAS #: 355-42-0, Strem Chemicals) and 75% (v/v) of an aqueous emulsifying agent. The aqueous phase consisted of either a lipid blend of 6.67 mg/mL 1,2-dipalmitoyl-sn-glycero-3-phosphocholine (DPPC, CAS #: 63-89-8 Avanti Polar Lipids, Inc., Alabaster, A L USA) and 0.27 mg/mL 1,2-dipalmitoyl-sn-glycero-3-phosphate monosodium salt (DPPA, CAS #: 169051-60-9, Avanti Polar Lipids, Inc) dissolved in a solution of propylene glycol (CAS #: 57-55-6, Sigma-Aldrich, St. Louis, Mo. USA), normal saline (Baxter Healthcare, Deerfield, Ill. USA), and glycerol (CAS #: 56-81-5, Sigma-Aldrich); 4 mg/mL bovine serum albumin (BSA) (CAS #: 9048-46-8, Sigma-Aldrich) dissolved in Dulbecco's phosphate buffered saline (DPBS, Life Technologies, Grand Island, N.Y. USA); or 4 mg/mL Pluronic F68 (CAS #: 9003-11-6, Sigma-Aldrich) dissolved in DPBS. The fluids were shaken with an amalgamator (Wig-L-Bug, Sigma-Aldrich) at 4800 rpm for 90 seconds (Fabiilli et al. 2009). The resulting emulsions were stored at 5° C. for 30 minutes and then subsequently washed with normal saline to remove excess emulsifier. The emulsions were characterized with a Coulter Counter (Multisizer 4, Beckman Coulter, Inc., Indianapolis, Ind. USA) in the range of 1-30 μm. All single emulsion formulations are listed in Table 1.

TABLE 1

Structure and composition of emulsions used to dope the ARSs. Sizing parameters of the emulsions were determined with a Coulter Counter. Data are shown as mean ± standard deviation for n = 3.

| Structure | PFC | Shell | Mean Diameter | Mean Diameter St. Dev. | Drop Concentration | Drop Concentration St. Dev. | % >6 microns | % >6 microns St. Dev. |
| --- | --- | --- | --- | --- | --- | --- | --- | --- |
| Single | PFP | Lipid | 2.34 | 0.08 | 6.27E+09 | 1.84E+09 | 5.99 | 1.93 |
| Single | PFH | Lipid | 2.27 | 0.04 | 6.54E+09 | 1.56E+09 | 4.78 | 1.23 |
| Single | PFH | BSA | 1.80 | 0.01 | 1.98E+10 | 2.41E+09 | 1.02 | 0.05 |
| Single | PFH | Pluronic F68 | 2.12 | 0.14 | 1.03E+10 | 2.99E+09 | 1.25 | 0.18 |
| Double | PFP | Fluoro Surfactant/ Pluronic F68 | 4.95 | 0.59 | 5.15E+08 | 9.67E+07 | 27.99 | 2.98 |
| Double | PFH | Fluoro Surfactant/ Pluronic F68 | 4.00 | 0.22 | 9.90E+08 | 3.17E+08 | 13.03 | 3.72 |

Double Emulsion Preparation and Characterization

Double emulsions ($W_1$/PFC/$W_2$) were prepared with PFP or PFH as the PFC phase by modifying a previous method (Fabiilli et al. 2010). A triblock fluorosurfactant, consisting of Krytox 157FSH (CAS #51798-33-5, DuPont, Wilmington, Del., USA) and polyoxyethylene glycol (MW: 1000 g/mol, CAS #: 24991-53-5, Alfa Aeser, Ward Hill, Mass. USA), was dissolved in 1 g of PFC at 2% (w/w). The PFC solution was then combined with an aqueous solution of fluorescein sodium salt (FSS, CAS #: 518-47-8, Sigma-Aldrich), reconstituted at 1 mg/mL in DPBS, in a volumetric ratio of 2.1:1. The phases were sonicated (CL-188, QSonica, LLC, Newton, Conn. USA) for 30 seconds while on ice. The resulting primary emulsion ($W_1$/PFC) was added drop wise to a solution of 50 mg/mL Pluronic F68 in DPBS and stirred with a magnetic stir bar at 700 rpm for 2 minutes while on ice. The particle size of the resulting coarse double emulsion ($W_1$/PFC/$W_2$) was reduced using a homogenizer (T10, IKA Works Inc., Wilmington, N.C. USA). The resulting emulsion had a FSS encapsulation efficiency of 89.7% and 92.3% for the PFP and PFH formulations, respectively. Emulsions were stored at 5° C. for 30 minutes and characterized with a Coulter Counter in the range of 1-30 μm. All double emulsion formulations are listed in Table 1.

ARS Fabrication

ARSs were prepared using 3, 5, or 10 mg/mL clottable protein by first combining bovine fibrinogen (Sigma-Aldrich), dissolved in degassed (40% $O_2$ saturation) Dulbecco's modified Eagle's medium (DMEM, Life Technologies), with bovine thrombin (2 U/mL, Thrombin-JMI, King Pharmaceuticals, Bristol, Tenn., USA), and 1% (v/v) emulsion. The mixture was injected into an OptiCell (Thermo Fisher Scientific Inc., Waltham, Mass. USA) and allowed to polymerize for 30 min at room temperature. Hydrogels without emulsions were prepared as a sham condition.

Ultrasound Exposure

Figure 6A:
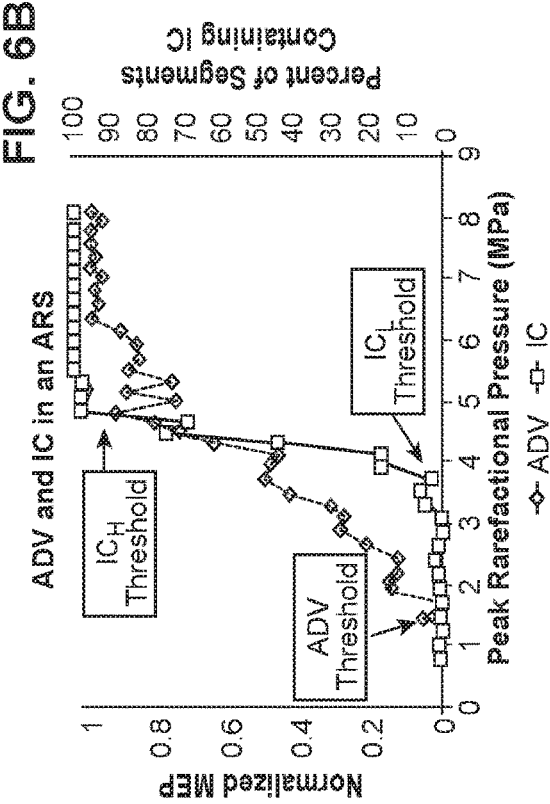
FIGS. 6A-6D show (A) Experimental setup used to expose ARSs to US. Representative plots showcasing the behavior of ADV, measured via enhanced brightness in the B-mode US images (i.e., MEP), and IC, measured via enhanced broadband noise, for an ARS (B) and a sham scaffold (C, without droplets). The ADV and $IC_L$ thresholds were defined as the first acoustic pressure data point that met the criteria in Equations 1 and 2, respectively. The threshold for persistent cavitation, $IC_H$, was defined as the first acoustic pressure data point where all 100 segments contained at least one IC event. For the sham scaffold (C), there was no detectable ADV due to the absence of droplets and also no enhanced brightness due to persistent bubbles generated by IC. Additionally, $IC_L$ occurred at a higher acoustic pressure relative to the ARS with the same fibrin concentration. ICH was not measured in the sham scaffold across the range of acoustic pressures interrogated in this work (i.e., 0-8.07 MPa). B-mode US images of the cross-section of an Opti-Cell containing an ARS (D). Images were taken before (DI) and after (DII) the ARS was exposed to high amplitude acoustic pulses generated by the single element US transducer. The subtracted image of DII-DI (DIII) clearly shows the bubbles generated by ADV in the ARS, which was used for ADV threshold analysis (i.e., MEP). Scale bar=2 mm.

OptiCells containing the ARSs were fixed vertically in a tank of degassed water (30-36% $O_2$ saturation) at 37° C., as shown in FIG. 6A. A calibrated, single element US transducer (2.5 MHz, H108, Sonic Concepts, Inc., Bothell, Wash. USA) was positioned such that the focus of the transducer was located equidistant from the OptiCell windows, which are 75 μm thick and spaced 2 mm apart. This single element transducer (f-number=0.83, focal length=50 mm) was used to generate ADV and IC within the ARS. Previous studies (Rahim et al. 2006a; Rahim et al. 2006b; Meijering et al. 2007) have demonstrated that OptiCell windows attenuate US in the range of 1-3 MHz by less than 1%. The ARS was exposed to 100 pulses of US that were 3, 6, or 13 acoustic cycles in length with a pulse repetition frequency (PRF) of 10 Hz and amplitudes ranging from 0.8-8 MPa peak rarefactional pressure. Waveforms were generated using a dual channel function generator (33500B, Agilent Technologies, Santa Clara, Calif. USA) and amplified by a gated radio frequency (RF) amplifier (GA-2500A Ritec Inc, Warwick, R.I. USA). Gating was realized using the second channel of the function generator. During exposure, broadband noise—indicative of IC (Madanshetty and Apfel 1991; Hwang et al. 2006)—was detected by a calibrated hydrophone (1-50 MHz, Onda Corporation, Sunnyvale, Calif. USA) that was coupled to the single element transducer and positioned 6 cm from the OptiCell. Hydrophone waveforms were digitized by an oscilloscope (HD04034, Teledyne Lecroy, Chestnut Ridge, N.Y. USA) at a sampling rate of 100 MHz. In order to detect bubble formation, B-mode US images were acquired before and after exposures from the single element transducer using a clinical US scanner (10 MHz US linear imaging array, 10L, GE Vivid 7, GE Healthcare, Waukesha, Wis. USA). To prevent the linear US array from generating ADV and/or IC within the ARS, a mechanical index (MI) of 0.03 was used, which is significantly lower than the MI required to cause cavitation (Apfel and Holland 1991). It was confirmed that this low MI caused no increase in echogenicity, and hence no ADV, in the ARS. For a given experimental run, which consisted of interrogating acoustic amplitudes in the range of 0.8-8.0 MPa peak rarefactional pressure, the spacing between each acoustic exposure in the OptiCell was 3 mm. This spacing minimized the interaction between exposure sites since the −6 dB lateral beam width of the single element transducer was measured as 0.61 mm. The minimum distance between an exposure and the edge of the OptiCell window was 10 mm. A total of 78 exposures was done per OptiCell with a separation of 10 mm between runs. All acoustic data (i.e., B-mode images and hydrophone data) were analyzed in MATLAB (The Mathworks Inc., Natick, Mass. USA). The B-mode images, before and after US exposure from the single element transducer, were subtracted and the mean echo power (MEP) was calculated for the subtracted image as done previously (Fabiilli et al. 2009). The ADV threshold was defined as $P_n$, where $P_n$ was the first acoustic pressure that satisfied Eqn. 1:

$$MEP_n > (\Sigma_{i=1}^{n-1} MEP_i)/(n-1) + 3\sigma \qquad (1)$$

where $MEP_n$ was the MEP of the $n^{th}$ pressure exposure, $MEP_i$ was the MEP of the $i^{th}$ pressure exposure, and σ was the standard deviation of $MEP_1, MEP_2, MEP_3, \ldots MEP_{n-1}$.

At each acoustic exposure condition, the RF signals collected using the hydrophone consisted of 100 segments, one for each of the 100 pulses fired by the single element transducer. A Hanning window was applied to each segment to time gate physical window reflections from the OptiCell and the direct path transmit signal from the single element transducer. Then the fast Fourier transform (FFT) of each segment was computed. Fundamental as well as second and third harmonics of the transmit US frequency were filtered out by excluding spectral amplitudes that were within 3 dB with respect to the maximum amplitude at each harmonic. The integrated power spectrum was then calculated across the entire detected frequency range (1-50 MHz)—although the majority of the signal was in the 1-10 MHz range—and then compared to the mean (across all segments) of the integrated FFT of the sham condition (i.e., an ARS without emulsion). Two thresholds related to IC were then calculated. First, the initiation of inertial cavitation ($IC_L$) was defined as the first pressure for which at least one of the 100 segments contained an IC event, which is defined in Eqn. 2:

$$S_n(P_{iARS}) > \Sigma_n^N s_n(P_{i,sham})/N + 3\sigma \qquad (2)$$

where $S_n(P_{iARS})$ is the $n^{th}$ segment in the sequence ($P_{iARS}$) for an ARS exposed to pressure $P_i$, $S_n(P_{i,sham})$ is the $n^{th}$ segment in the sequence $P_{i,sham}$ for a sham exposed to pressure $P_i$, N is the total number of segments, and σ is the standard deviation of the mean of the sham. Second, persistent cavitation ($IC_H$) was defined as the first pressure at which an IC event was detected in all 100 segments, and thus each segment passed the criterion in Eqn. 2.

Viability of Encapsulated Cells

ARSs were prepared as previously described except that $5.0 \times 10^4$ cells/mL of the mouse multipotent line C3H10T1/2, clone 8 (CCL-226, ATCC, Manassas, Va., USA) were encapsulated along with 1% (v/v) PFP double emulsion in 5 mg/mL fibrin. Prior to casting the ARS, OptiCell windows were blocked with a 10 mg/mL solution of BSA. The acoustic exposures (13 cycles and 10 Hz PRF) were completed as previously described except that the single element transducer was rastered across the OptiCell in a paintbrush format to create large regions exposed to the same acoustic condition (rather than a single point as section 2.4). To achieve this, each OptiCell was divided into six equally-sized regions of 500 $mm^2$, with each region spaced 2 mm from each neighboring region and 5 mm from the edge of the OptiCell window. Each region was exposed to US at a fixed acoustic amplitude. The single element transducer, which was attached to a micropositioning system, was rastered across each region at 0.64 mm/s (i.e., 15 pulses/mm) with a 1 mm spacing between exposure lines. These raster parameters yielded relatively uniform bubble production within the ARS. Immediately after US exposure, the ARS was biopsied with an 8 mm biopsy punch (Miltex, Plainsboro, N.J. USA) and each biopsied sample was placed in 0.05% trypsin-EDTA (Gibco, Grand Island, N.Y. USA) for 20 min to degrade the hydrogel. The sham condition (i.e., 0 MPa) was also exposed to the same handling conditions and trypsin degradation as the experimental condition. There was no statistically significant difference in viability when comparing the sham before and after incubation in trypsin for 20 min. Following complete degradation of the ARS sample, the remaining cells were isolated via centrifugation, resuspended in DMEM, and then stained with 16.2 µM Hoechst 33342 (Invitrogen, Grand Island, N.Y. USA), 5 µM calcein AM ("Live" stain, Invitrogen), and 15 µM propidium iodide (PI, "Dead" stain, Invitrogen). The labeled cells were imaged with a Leica DM IL microscope (Leica Microsystems Inc., Buffalo Groove, Ill. USA) using a 10× objective.

Physical Stability of ARSs

For stability studies, 0.5 mL ARSs were cast in 24 well plates (Corning Life Sciences, Tewksbury, Mass. USA) with 1% (v/v) emulsion—either single or double—and 5 mg/mL fibrin. Double emulsions contained 1 mg/mL FSS in the $W_1$ phase. After polymerization at room temperature, each ARS was covered with DMEM and placed in a standard tissue culture incubator at 37° C. At each time point, the overlying media was removed and the ARS was degraded with 0.05% trypsin-EDTA. Following complete degradation of the ARS, the resulting sample was centrifuged and the remaining emulsion was sized using a Coulter Counter as previously described. It was experimentally confirmed that incubation of the emulsion in trypsin did not alter the size distribution or number density of the emulsion. For studies with double emulsions, the concentration of FSS in the overlying media was determined using a plate reader (Molecular Devices Spectramax M2e, Sunnyvale, Calif., USA, 494 nm EX/521 nm EM). Measurements were taken twice on the first day at t=0 h and t=2 h, then every 24 h from t=24 h for 144 h. The stability of the emulsions, not contained within ARSs, was also measured using the aforementioned methods. Light microscopy (10× objective, Leica DM IL) images of ARSs containing single PFP and PFH emulsions were taken at t=0 and t=72 h to depict differences in physical stability.

Statistics

The data are expressed as the mean±standard deviation of measured quantities. All n-values are listed below each corresponding figure. The Tukey-Kramer method, evaluated in MATLAB, was used to determine statistically significant differences between multiple groups for acoustic data (i.e., ADV and IC thresholds), with differences deemed significant for p<0.05. The 95% confidence interval of slopes is listed in the following format: S [$S_L$, $S_H$], where S is the average slope, $S_L$ is the lower bound slope and SH is the upper bound slope). Statistically significant differences of all other data sets were determined with a Student's t-test with differences deemed significant for p<0.05.

Results

Characterization of Emulsions

Table 1 displays the sizing characteristics of the single and double emulsions used in the ARSs. For lipid shell single emulsions, no statistical differences in the mean diameter, droplet concentration, and number percent greater than 6 µm were observed between PFP and PFH emulsions. However, a smaller mean diameter, larger droplet concentration, and a smaller number percent greater than 6 µm were measured when the single PFH emulsions were stabilized with BSA or Pluronic F68 versus lipid. Double emulsion droplets were larger than single emulsions. Additionally, no differences in mean diameter were observed between double emulsions made with PFP and PFH, however PFP double emulsions had a smaller droplet concentration and larger percentage of droplets greater than 6 µm than PFH double emulsions.

ADV and IC Thresholds

Figure 6B:
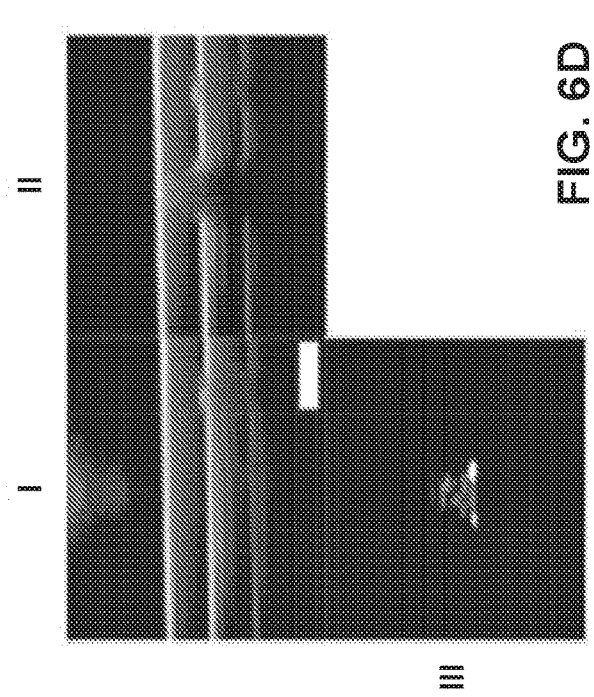
Figure 6C:
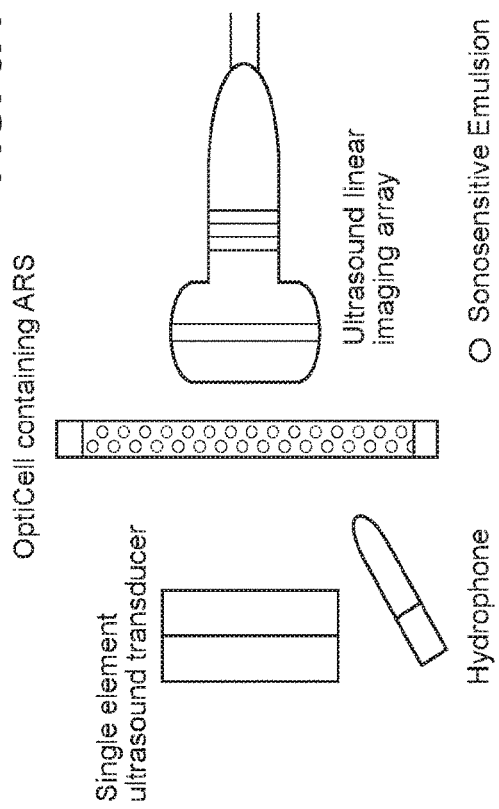
Figure 6D:
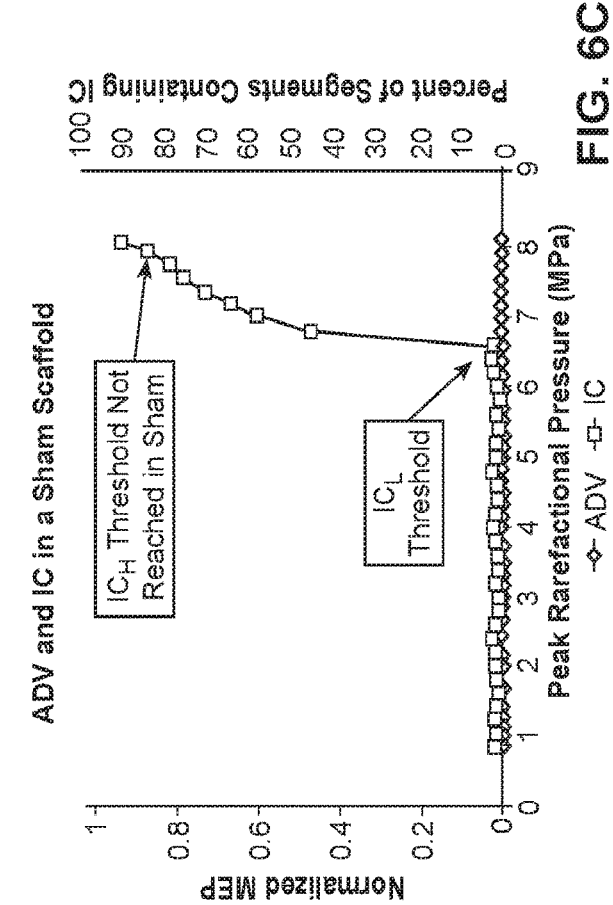

FIGS. 6B-C display the characteristic trends in ADV and IC of ARSs and sham fibrin scaffolds. At low acoustic pressures, neither bubbles (i.e., ADV) nor IC was detected in the ARS or the sham. As the acoustic pressure was increased, the ADV threshold was reached and the droplets in the ARS started to vaporize, generating echogenic bubbles that increased the MEP in the recorded B-mode images FIG. 6D. Thus, any acoustic pressure greater than the ADV threshold triggered ADV. A further increase in the acoustic pressure caused the first detectable IC event (i.e., the $IC_L$ threshold), where both IC and ADV occurred. Eventually, at an acoustic pressure higher than the $IC_L$ threshold, persistent IC was detected (i.e., all recorded segments contained at least one IC event). This pressure was the $IC_H$ threshold for an ARS. The acoustic pressure range where $IC_H$ occurred also contained ADV due to detectable bubble formation with B-mode imaging. Sham scaffolds (i.e., fibrin scaffolds without emulsion) did not display an ADV threshold and $IC_L$ occurred at a higher acoustic pressure than the $IC_L$ threshold of an ARS with the same fibrin concentration and exposed to the same number of acoustic cycles. Furthermore $IC_H$ was not detected in any of the sham scaffolds—containing 3, 5, or 10 mg/mL fibrin. FIG. 6D shows a B-mode image of an OptiCell containing an ARS. FIG. 6D-I and FIG. 6D-II shows the ARS before and after US exposure from the single element transducer, respectively. The change in echogenicity (i.e., brightness) post US exposure can be observed, and FIG. 6D-III shows an image subtraction of FIGS. 6D-I and 6D-II displaying clear persistent bubble formation and the appearance of the back OptiCell window produced by its shadowing in FIG. 6D-II due to bubble production.

The ADV, $IC_L$, and $IC_H$ ($IC_{L/H}$) thresholds for an ARS with 5 mg/mL fibrin and doped with varying single emulsion cores (PFP vs. PFH) stabilized by a lipid shell were quantified (FIG. 2A). Qualitatively, all thresholds tended to decrease as the number of acoustic cycles increased, with a statistically significant difference between 3 and 13 cycles for PFH droplets. All thresholds were higher for PFH than PFP at 3 cycles. There were no differences between ADV and $IC_L$ for any acoustic condition in FIG. 7A. However, ICH was larger than ADV and ICL for both PFP and PFH at 3 and 6 cycles; at 13 cycles, no differences were observed with the ADV and $IC_{L/H}$ thresholds.

Figure 7A:
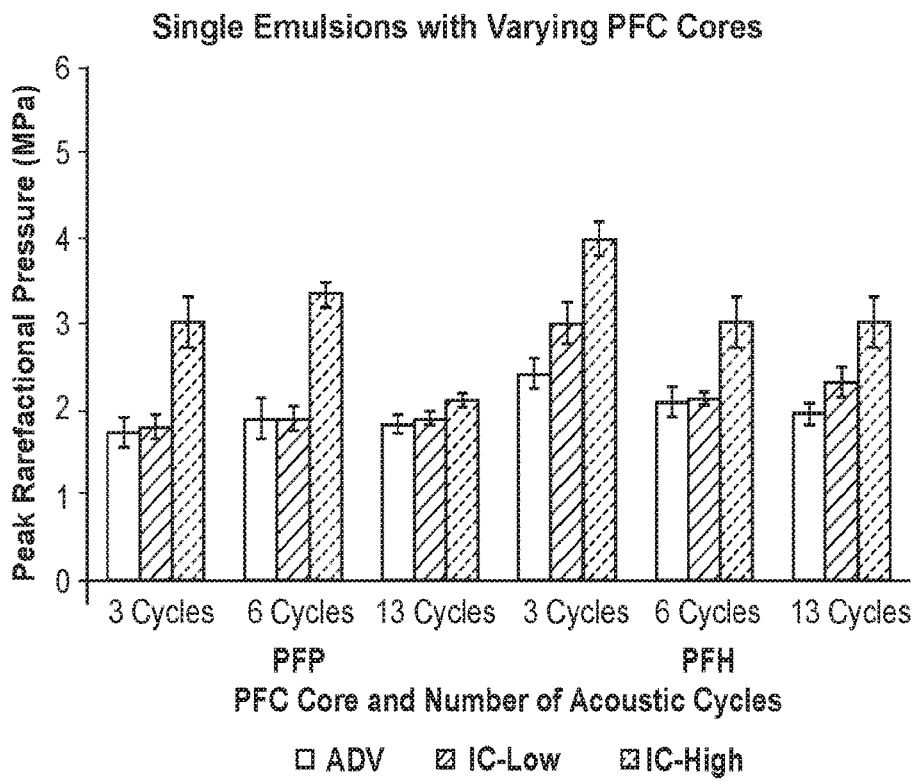
FIGS. 7A-7D show ADV and IC thresholds of ARSs containing varying (A) droplet formulations (i.e., different PFC cores), (B) fibrin concentration, (C) droplet shell material, and (D) emulsion structures. For each parameter set, the number of acoustic cycles was varied. In (B) and (C), the ARSs were doped with a PFH single emulsion. A fibrin concentration of 5 mg/mL fibrin was used in ARSs in (A), (C), and (D). A lipid shell was used in (A) and (B). For certain conditions in (D), $IC_H$ was not detected in the range of acoustic pressures interrogated in this work (i.e., 0-8.07 MPa); these conditions are denoted by an 'x'. Data are shown as mean±standard deviation for n=5 and all ARSs were prepared the day of acoustic measurement.
Figure 7B:
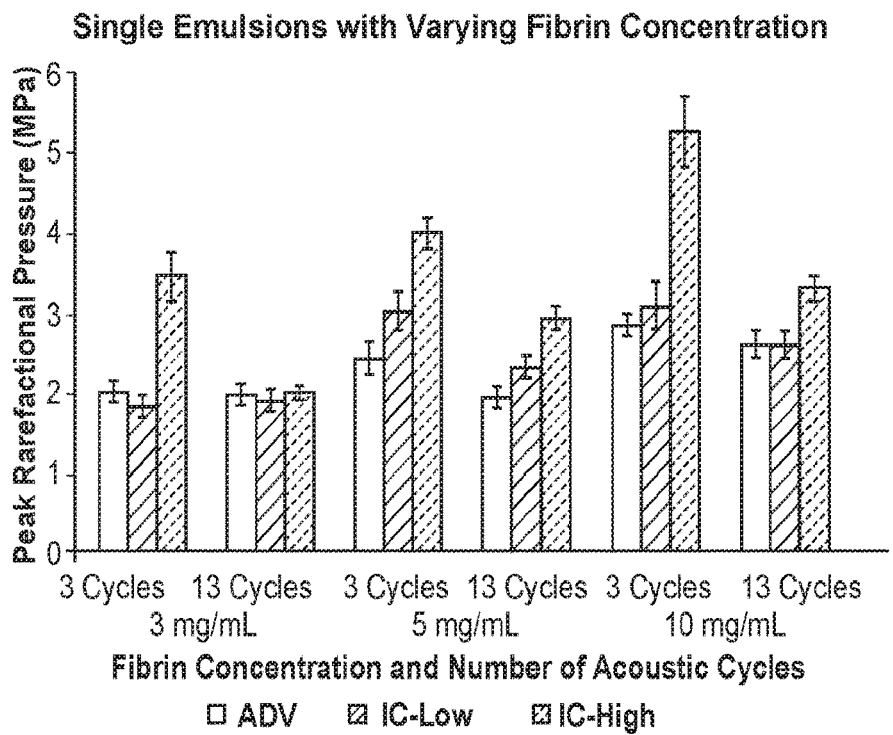

FIG. 7B shows the ADV and $IC_{L/H}$ thresholds for ARSs containing either 3, 5, or 10 mg/mL fibrin and doped with a lipid stabilized, PFH single emulsion. Qualitatively, the ADV and $IC_{L/H}$ thresholds directly correlated with fibrin concentration, with statistically larger ADV and $IC_L$ thresholds at 10 mg/mL versus 3 mg/mL for all acoustic cycles. Similar to the data in FIG. 7A, the ADV and $IC_{L/H}$ thresholds decreased as the number of acoustic cycles increased for 5 and 10 mg/mL fibrin. The $IC_H$ threshold was higher than the ADV and $IC_L$ thresholds for all acoustic conditions and fibrin concentrations except 13 cycles at 3 mg/mL.

Figure 7C:
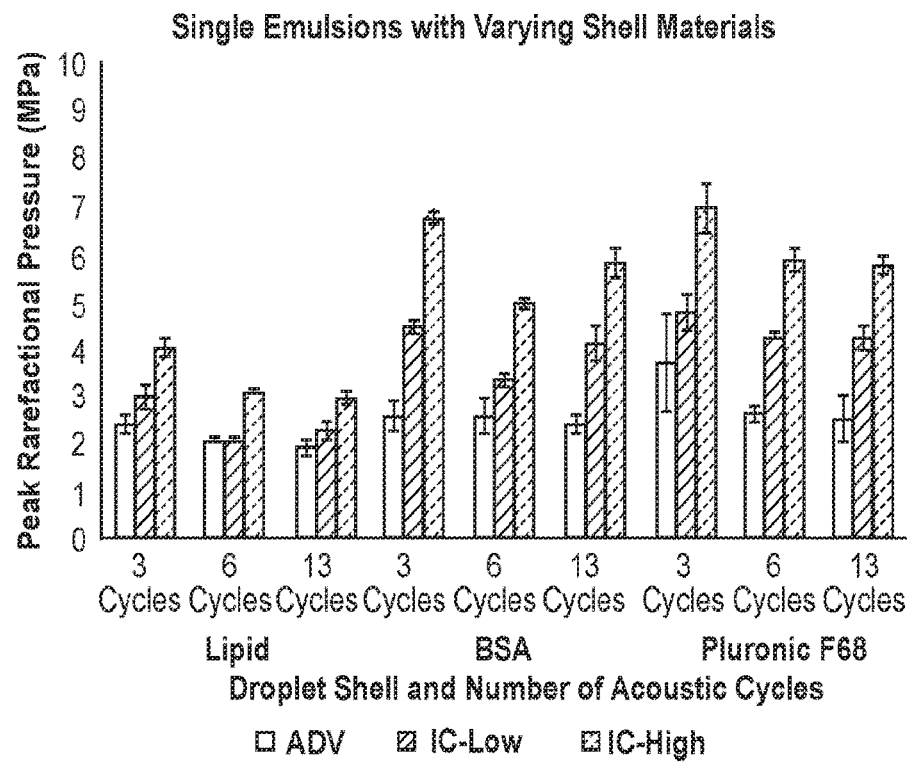

The ADV and $IC_{L/H}$ thresholds for ARSs containing 5 mg/mL fibrin and doped with single PFH emulsions of varying droplet shell composition are displayed in FIG. 7C. ARSs doped with lipid shelled emulsions had a lower $IC_L$ threshold compared to the protein based BSA shell and the polymer based Pluronic F68 shell emulsions at all acoustic cycles, with the largest difference occurring between lipid and Pluronic F68 emulsions. A higher ADV threshold was observed with Pluronic F68 shell emulsions versus lipid shell emulsions at 6 acoustic cycles. For all cases, the $IC_H$ threshold occurred at a higher acoustic pressure than the ADV and $IC_L$ thresholds. Increasing the number of acoustic cycles yielded lower $IC_H$ thresholds for all three shell materials when comparing 3 versus 13 acoustic cycles.

Figure 7D:
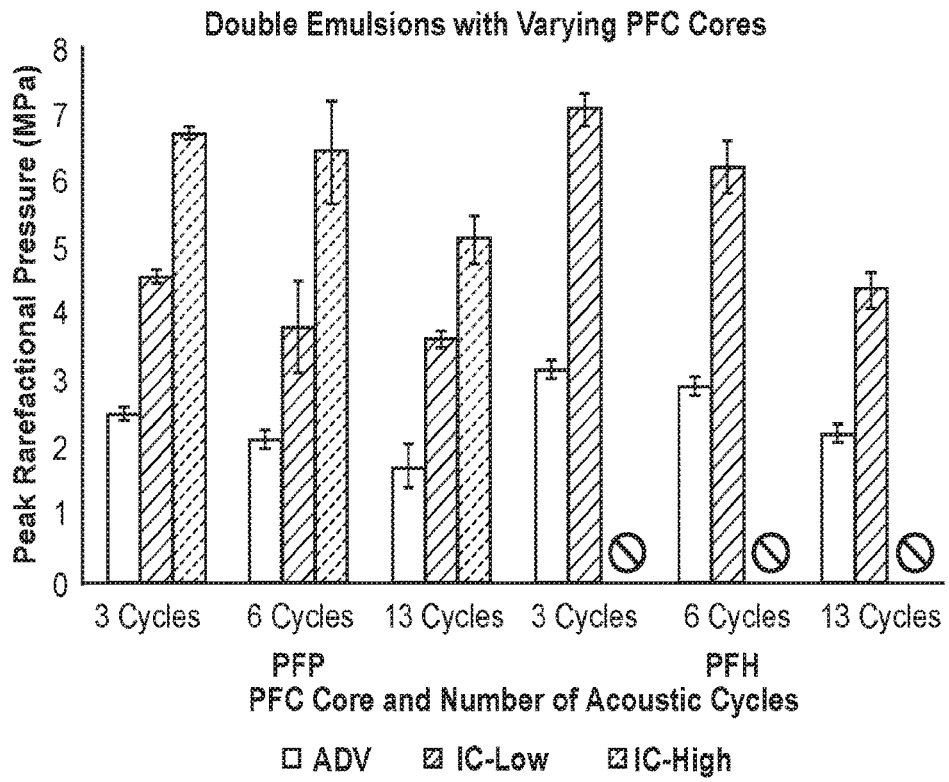

In FIG. 7D, the ADV and $IC_{L/H}$ thresholds for ARSs containing 5 mg/mL fibrin and doped with either PFP or PFH double emulsions are shown. Similar to the trend observed in FIG. 7A, PFH emulsions had higher ADV and $IC_L$ thresholds than PFP emulsions when comparing 3 and 6 acoustic cycles. The $IC_H$ threshold was higher than the ADV and $IC_L$ thresholds within all acoustic conditions for PFP emulsions. The $IC_L$ threshold for ARSs doped with PFH double emulsion was equivalent to that observed in the sham. $IC_H$ was not detected with PFH emulsions in the range of acoustic pressures tested.

Cell Viability

Figure 8:
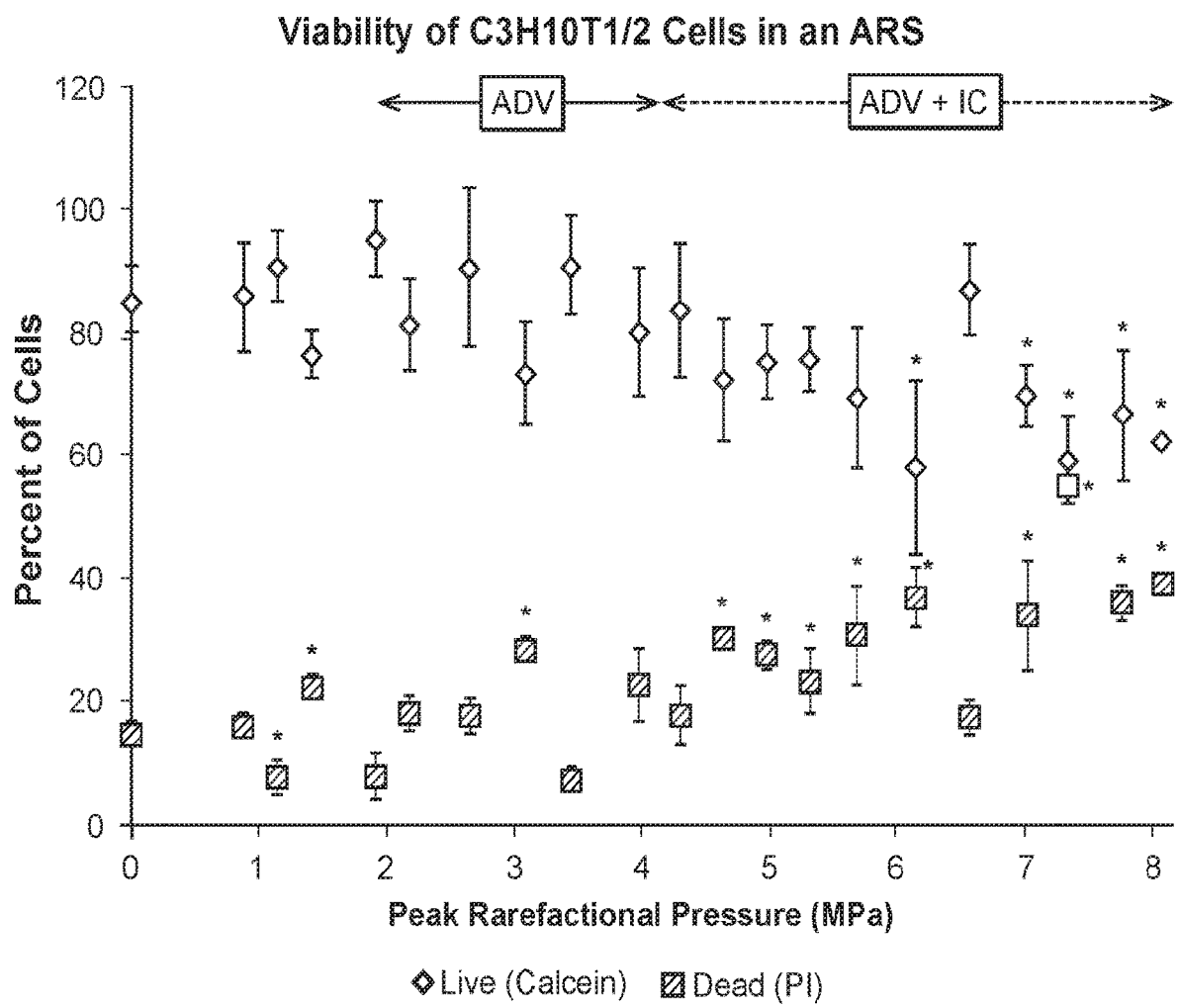
FIG. 8 shows viability of C3H10T1/2 cells in an ARS containing 5 mg/mL fibrin, 1% (v/v) PFP double emulsion, and 50,000 cells/mL after exposure to US at 13 cycles and 10 Hz PRF. Viability was determined with calcein for live staining, propidium iodide for dead staining, and Hoechst for total number of cells. The sham condition (i.e., 0 MPa) underwent the same experimental steps and exposure to environmental conditions as the non-sham conditions. Data are shown as mean±standard deviation for n=9. *p<0.05 vs. no US condition.

The viability of C3H10T1/2 cells encapsulated in an ARS containing 5 mg/mL fibrin and doped with PFP double emulsion was quantified FIG. 8. This ARS was identical in composition to the ARS in FIG. 7D, with the addition of cells. In FIG. 7D, the ADV, $IC_L$, and $IC_H$ thresholds occurred approximately at 2, 3.8, and 5 MPa, respectively. The percentage of live cells (i.e., calcein$^+$) correlated inversely with acoustic pressure, with a linear regression of the entire data yielding a slope of −3.2 [−4.7, −1.7]. Conversely, the percentage of dead cells (i.e., PI$^+$) was directly correlated with acoustic pressure, with a linear regression of the entire data yielding a slope of 3.7 [2.2, 5.3]. In the region before ADV and IC (i.e., 0-2 MPa), regressions of the live and dead data yield slopes whose 95% confidence intervals are nearly centered at zero (live: −0.1 [−25.8, 25.6], dead: 0.6 [−21.6, 22.8]), thus indicating no change in cell viability. In the region from 0 to 4 MPa, regressions of the live and dead data yield a slope of −0.9 [−5.5, 3.7] for live and 1.6 [−2.9, 6.1] for dead. In the region between 4 and 8 MPa, regressions of the live and dead data yield a slope of −5.7 [−9.5, −1.9] for live and 5.2 [0.3, 10.0] for dead.

Physical Stability of ARSs

Figure 9:
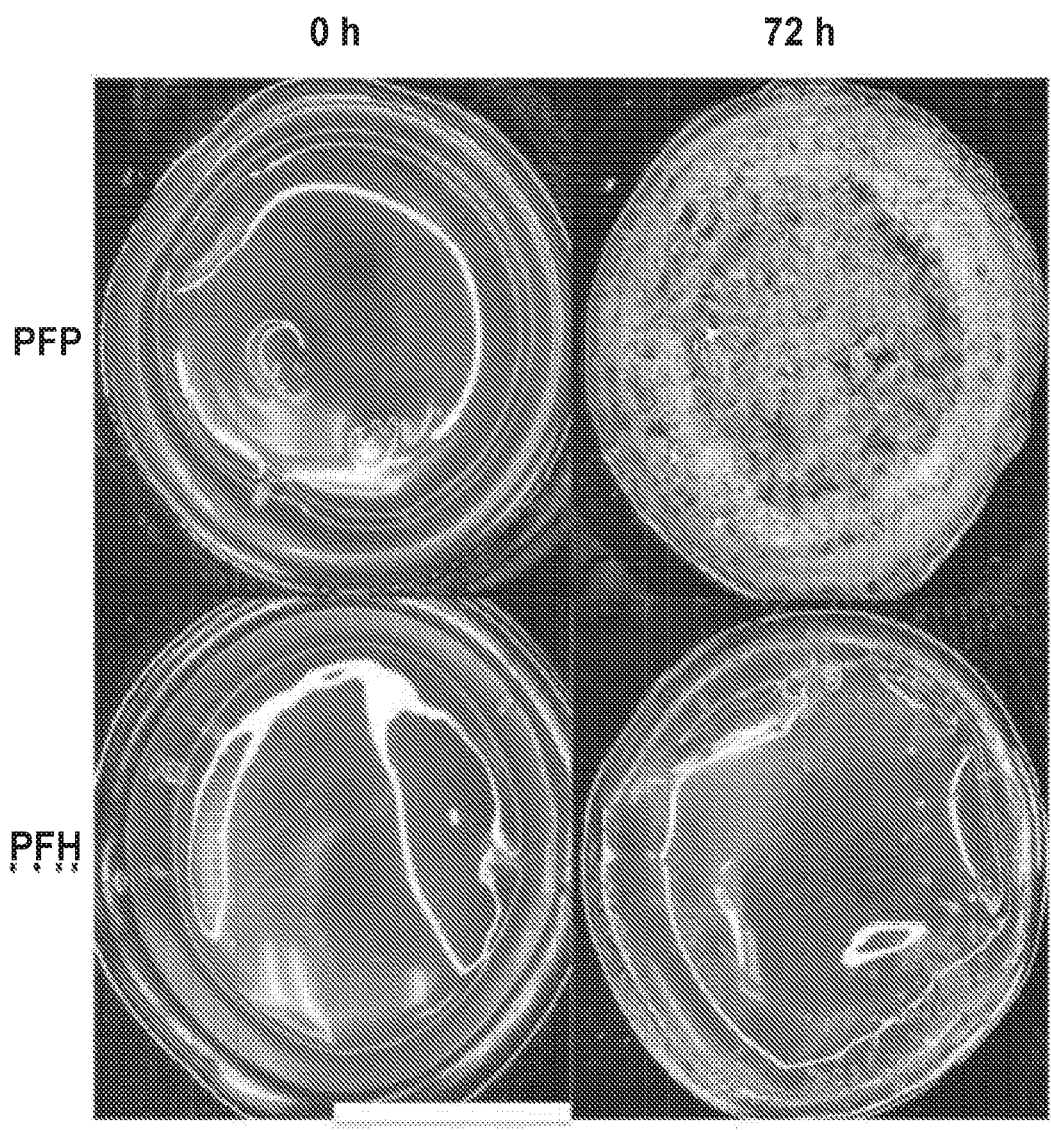
FIG. 9 shows light microscopy images of ARSs doped with 1% (v/v) PFP or PFH emulsions at 0 h and 72 h after polymerization. Between imaging, the ARSs were placed in a standard tissue culture incubator at 37° C. and were not exposed to US. Scale bar=7.8 mm.

Light microscopy images of ARSs containing 5 mg/mL fibrin and doped with PFP or PFH double emulsions immediately after and 72 h after polymerization are shown in FIG. 9. These ARSs were not exposed to US and were placed in a standard tissue culture incubator at 37° C. between imaging sessions. At 0 h both ARSs contained no bubbles. However after 72 h of incubation, the ARS doped with PFP emulsion contained significantly more bubbles than the ARS doped with PFH emulsion.

Figure 10A:
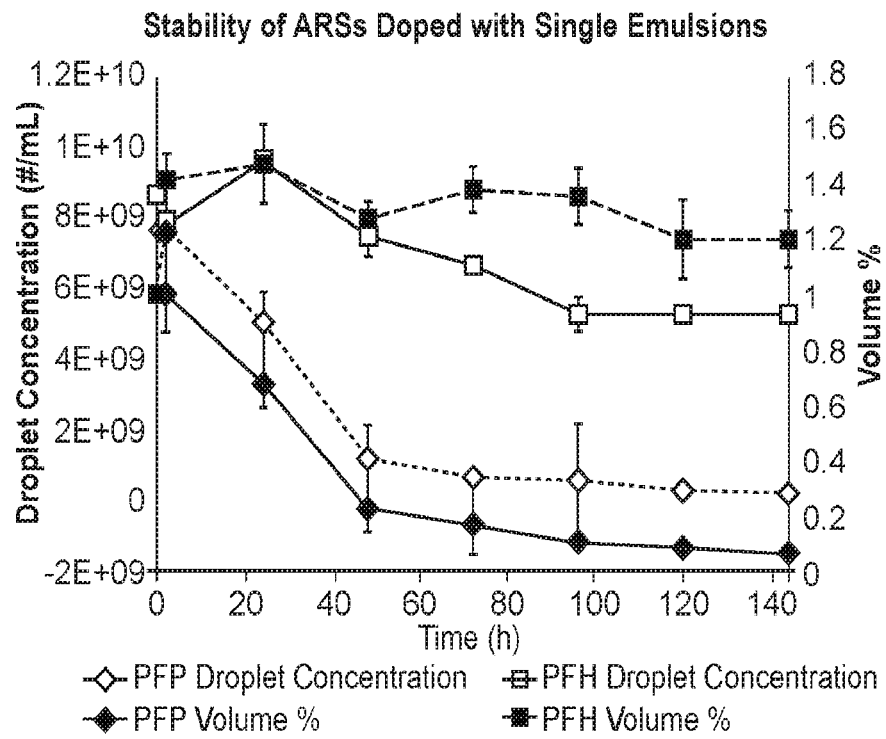
FIGS. 10A and 10B show physical stability of ARSs doped with single (A) and double (B) emulsions. The ARSs were degraded with 0.05% trypsin and the remaining emulsion was sized with a Coulter Counter. Data are shown as mean±standard deviation for n=5.
Figure 10B:
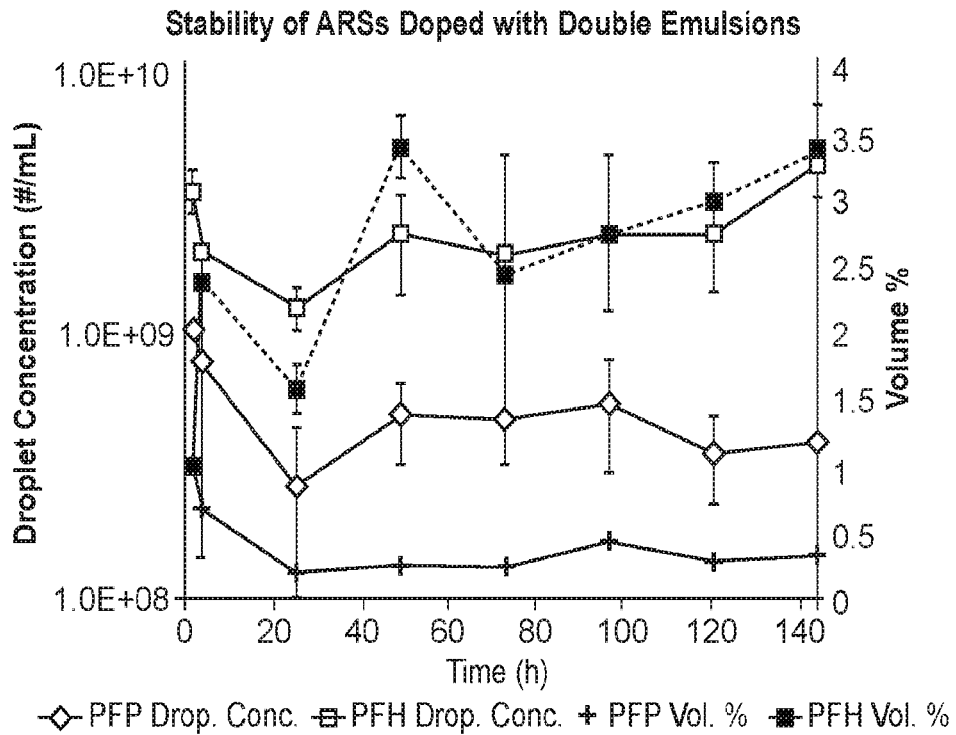
Figure 11:
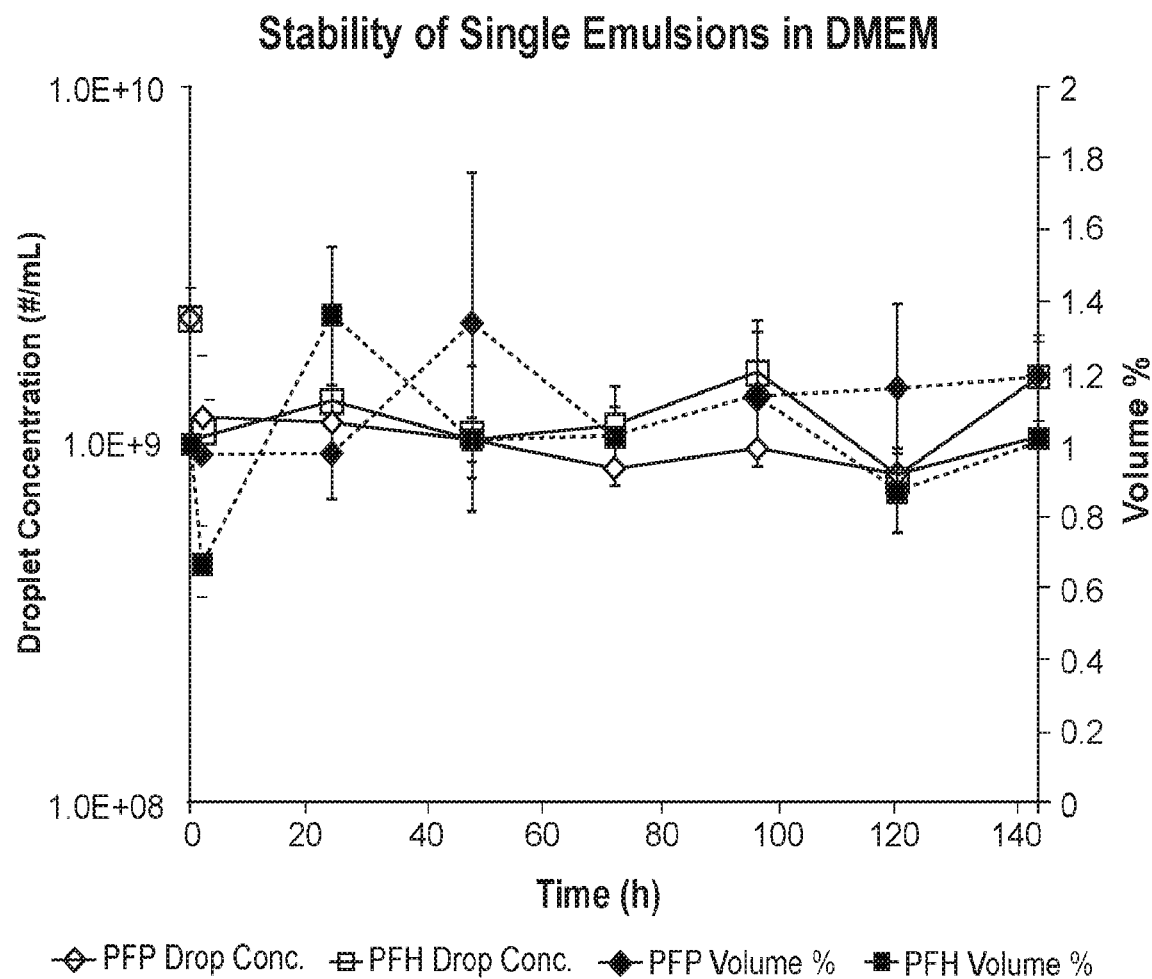
FIG. 11 shows physical stability of single (A) and double (B) emulsions in DMEM. The emulsions were fabricated, and incubated, in the exact same manner as the emulsions contained in ARSs. Sizing was done with a Coulter Counter. Data are shown as mean±standard deviation for n=5.

Quantification of the physical stability of ARSs containing 5 mg/mL fibrin and doped with single or double emulsions is presented in FIGS. 10A-B. The stability is displayed in terms of droplet concentration (i.e., number density per volume of ARS) and volume percentage of droplets remaining. Note that the ARSs initially contained 1% (v/v) emulsion. FIG. 10A shows the physical stability of ARSs doped with PFP or PFH single emulsions. After 2 h, ARSs doped with PFH single emulsion exhibited a 10% decrease in droplet concentration. After 144 h, a 40% decrease in droplet concentration, relative to 0 h, was observed for the ARS with PFH emulsion. The volume percentage increased to 1.4% after 2 h of incubation and decreased to 1.2% after 144 h of incubation. For ARSs with PFP single emulsions there was a statistically significant decrease in both droplet concentration and volume percentage beginning 24 h after incubation, relative to 0 h, with further decreases in both metrics over time. At 144 h, the droplet concentration and volume percentage decreased by 97% and 94%, respectively, compared to 0 h. No statistically significant differences in mean diameter or number percent greater than 6 µm was observed for ARSs with single PFP or PFH emulsions (data not shown). As a comparison, FIG. 11 shows the stability of the same single emulsion formulations in DMEM, at the same concentration used in the ARSs (i.e., 1% (v/)). Overall, droplet concentration and volume percentage of emulsions did not change at 144 h relative to 0 h for PFP and PFH emulsions.

FIG. 10B show that ARSs containing PFP double emulsion exhibited a 50% decrease in droplet concentration 24 hours after polymerization. The concentration then remained relatively unchanged through the remainder of the experiment, with a linear regression of the PFP droplet concentration data yielding a slope roughly centered at zero [−2.8× $10^6$, 3.5×$10^6$]. A 61% decrease in droplet concentration was observed when comparing 0 h versus 144 h. The volume percentage also decreased after 24 hours and remained relatively constant at 0.5%, with a linear regression through the data yielding a slope of 0.001 [−0.001, 0.003]. A 68% decrease in volume percentage was observed when comparing 0 h versus 144 h. This is similar to the results observed in FIG. 10A where the ARSs doped with PFP single emulsion exhibited a statistically significant decrease in both volume percentage and droplet concentration at 144 h relative to 0 h. For ARS with PFH double emulsion, both the droplet concentration and volume percentage of droplets increased with time. A 27% increase in droplet concentration and a 238% increase in volume percentage was seen when comparing data at 0 h and 144 h. No statistically significant differences in mean diameter or number percent greater than 6 µm was observed for ARSs with double PFP or PFH emulsions.

The stability of double emulsions in DMEM was also determined. Similar to single emulsions in DMEM, the droplet concentration and volume percent of emulsions did not decrease at t=144 h relative to t=0 h for PFP or PFH emulsions. For PFH double emulsions, the volume percentage increased to 2% (v/v).

Non-Selective Payload Release

Figure 12:
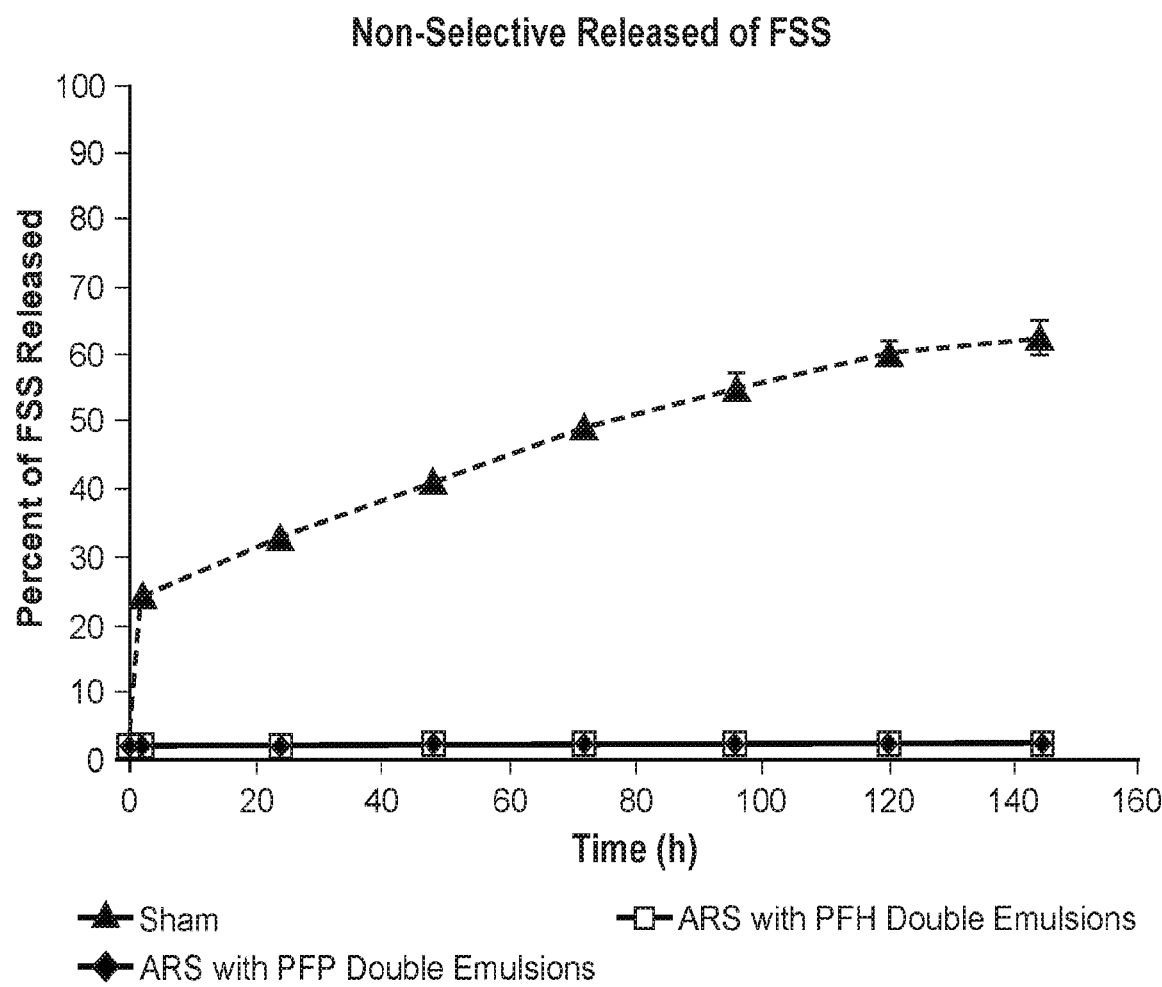
FIG. 12 shows non-selective (i.e., without US exposure) release of a small molecular weight surrogate payload, FSS, from ARSs containing PFP or PFH double emulsions. The FSS was encapsulated within the $W_1$ phases of the respective emulsions. The ARSs were placed in a standard tissue culture incubator at 37° C. The release profile of non-emulsified FSS, doped within a sham fibrin scaffold (i.e., without emulsion) is also shown. Data are shown as mean±standard deviation for n=5.

The release of FSS from ARSs containing 5 mg/mL fibrin and doped with PFP or PFH double emulsions is shown in FIG. 12. The FSS was initially encapsulated within the $W_1$ phase of each emulsion. The data in FIG. 12 was acquired in the same experiment as the stability data in FIGS. 10A-10B. As a control, the release profile of FSS, not encapsulated in a double emulsion but incorporated directly into the fibrin scaffold, is also shown. After 144 hours, less than 3% of the initially loaded FSS is released from the ARSs with either the PFP or PFH emulsions. Comparatively, 62% of the initially loaded FSS was released from the control scaffold after 144 hours.

Discussion

Recently, we demonstrated that US can be used to actively control GF release, architecture, and stiffness in a fibrin scaffold doped with sonosensitive emulsion (Fabiilli et al. 2013, incorporated by reference herein in its entirety). Here the acoustic response of fibrin-based ARSs was characterized with a surrogate payload and related to cell viability within the scaffold, while also focusing on the stability of the ARSs. By design, an ARS is more responsive to US than a conventional fibrin scaffold. The results demonstrated that stable bubbles were created via ADV in all tested compositions of ARSs. For acoustic measurements, all ARSs and sham hydrogels were formulated with degassed DMEM and placed in a degassed water tank, which decreased the amount of dissolved gas present and thus likelihood for bubble generation and persistence within the scaffolds. Bubble formation was not detected in the sham scaffolds (i.e., no droplets) using B-mode US. Additionally, $IC_L$, and $IC_H$ thresholds were lower in the ARSs, compared to the sham scaffold, except in the case of ARS doped with PFH double emulsions at 3 and 6 cycle pulses FIG. 7D. This is consistent with previous studies, where the IC threshold of a solution containing microbubbles or high concentrations of dissolved gas was lower than the IC threshold in the same solution without microbubbles or a low concentration of dissolved gas (Fabiilli et al. 2009). During IC, the rapid collapse of cavitation nuclei typically results in various remnant fragments (Flynn and Church 1984; Brennen 2002; Pishchalnikov et al. 2008). These daughter nuclei last from milliseconds to full seconds (Epstein and Plesset 1950; Chen et al. 2002; Pishchalnikov et al. 2008), and may serve as cavitation nuclei for following US pulses. However in degassed media, more aggressive acoustic conditions are required to form cavitation nuclei and any subsequent daughter nuclei. In vitro and in vivo bioeffects related to IC have been found to correlate with the IC dose, which is the magnitude of IC activity over time (Hallow et al. 2006; Hwang et al. 2006). Thus, for delivery of large molecules such as GFs that have higher order structure, avoidance of acoustic pressures that generate persistent IC may be beneficial in retaining GF bioactivity (Marchioni et al. 2009).

A trend observed in prior work was that the ADV threshold occurred at a lower acoustic pressure than the $IC_L$ threshold, where the bubbles generated by ADV were hypothesized to undergo IC (Fabiilli et al. 2009; Schad and Hynynen 2010). These previous studies measured the acoustic thresholds of sonosensitive emulsions in flowing saline, thus emulating the presence of intravascularly administered emulsion in blood flow. Depending on the flow velocity and acoustic parameters, bubbles generated by ADV may not be insonified by multiple pulses of US. However, bubbles formed in the ARSs are relatively stationary and thus are exposed to multiple acoustic pulses. Therefore, given that 100 pulses were fired at one location within the ARS FIGS. 7A-7D, a bubble formed by ADV within the first 99 pulses fired by the single element transducer has the potential to undergo IC during the remaining pulse, at a given acoustic pressure.

ARSs doped with PFH double emulsions displayed higher ADV and $IC_{L/H}$ thresholds than ARSs doped with PFP double emulsions FIG. 7A versus FIG. 7D. Interestingly, ARSs doped with PFP or PFH single emulsions displayed similar thresholds. Previous studies have demonstrated that the acoustic pressure required to vaporize a PFC emulsion was related to the boiling point of the PFC (Kawabata et al. 2005; Fabiilli et al. 2009; Sheeran et al. 2011). However another study showed that the IC thresholds of PFC emulsions was independent of the boiling point of the dispersed PFC phase (Giesecke and Hynynen 2003). Gases are very soluble in PFCs, especially oxygen, with the solubility inversely correlated to PFC molecular weight (Riess 2001; Dias et al. 2004; Johnson et al. 2009). It is hypothesized that the interaction of US with the dissolved gases within a PFC droplet causes the vaporization of high boiling point PFCs, such as perfluoro-15-crown-5-ether (boiling point: 146° C.) (Rapoport et al. 2011) or yields similar IC threshold for PFCs with different molecular weights (Giesecke and Hynynen 2003). Thus, the similar ADV thresholds in ARSs with single PFP and PFH emulsions may potentially be attributed in part to high gas solubility within both PFCs.

For the same number of acoustic cycles, ARSs doped with double emulsions generally displayed higher ADV and $IC_{L/H}$ thresholds than ARSs doped with single emulsions FIG. 7A versus FIG. 7D. These acoustic differences could be due to variations in the outer shell stabilizing the emulsion droplets, droplet diameter, or emulsion morphology. The outer shells of the single and double emulsions were lipid and Pluronic F68, respectively. It can be seen in FIG. 7C that ARSs containing single emulsions with Pluronic F68 shells had higher acoustic thresholds than ARSs with single emulsions with lipid shells. Since the ADV threshold is inversely related to droplet size (Fabiilli et al. 2009; Schad and Hynynen 2010; Sheeran et al. 2011), it was expected that the ADV threshold of ARSs with double emulsions would have been lower than single emulsions since the double emulsions were larger in size (Table 1). Thus, it is hypothesized that the mechanism governing the initiation of ADV for double emulsions is different than that of single emulsions. In addition, the fraction of PFC within a double emulsion droplet is smaller than in a single emulsion droplet, which may diminish the probability for an appropriate nucleation site and therefore increase the pressure needed to trigger ADV in a double emulsion. Prior work has also shown that the expansion rate of double emulsions is slower than that of single emulsions during ADV (Shpak et al. 2013). Thus more acoustic energy may be required to displace the viscous hydrogel media surrounding the double emulsion droplet while also preventing recondensation of the PFC during the relatively slow expansion.

For ARSs with single emulsions, the effects of shell material and droplet size on ADV and $IC_{L/H}$ thresholds cannot be completely decoupled since different shells yielded differently sized emulsions. As stated previously, higher thresholds were observed with Pluronic F68 emulsions versus lipid shell emulsions FIG. 7C. Microbubbles with a soft-shell surfactant, such as lipid, can undergo net radial fluctuations of at least 15%, while stiffer albumin-shelled microbubbles demonstrate constrained expansion and contraction when exposed to US (Dayton et al. 1999). In addition, microbubbles with stiffer polymer based shells have higher fragmentation thresholds than lipid-based microbubbles (Chen et al. 2003). Lipid shell emulsions also displayed the largest mean diameter and highest percentage of droplets greater than 6 μm, which could also lead to a lower ADV and $IC_{L/H}$ thresholds. Within an ARS, the interaction between a droplet and the surrounding fibrin could be affected by the physiochemical properties of the shell stabilizing the droplet. For example, Pluronic F68 can alter the arrangement of fibrin fibers, which could ultimately impact the acoustic response of the ARS (Vangelder et al. 1993). Such interactions would also explain the apparent instability of the PFP droplets in the ARSs in comparison to that found in aqueous solutions. In addition, the ADV thresholds of single emulsions within the ARS could be modified by altering surfactant composition, which has been shown to influence the interfacial tension of PFC and aqueous solutions (Kandadai et al. 2010).

With conventional fibrin scaffolds, the rate of cellular infiltration and the extent of neovascularization are inversely related to fibrin density (Kniazeva et al. 2011). In this study, higher ADV and IC thresholds were observed as the fibrin concentration of the ARS increased. The inertia of the surrounding media, large Laplace pressure, and viscosity may delay the startup of bubble nucleation during ADV or growth during ADV/IC. If the time delay caused by these factors comprise a significant portion of the acoustic period, then a much higher acoustic pressure could be required to initiate the growth of the bubble from the emulsion or to cause the generated bubble to undergo IC (Apfel 1986; Holland and Apfel 1989; Fabiilli et al. 2009; Fabiilli et al. 2013). Overall, ADV and IC thresholds generally decreased as the number of acoustic cycles increased. Previous research has demonstrated an inverse correlation between the IC threshold and the number of acoustic cycles, especially in the range of 1 to 10 cycles (Atchley et al. 1988; Fowlkes and Crum 1988; Ammi et al. 2006).

Since the ADV and IC thresholds can be modulated by altering the composition of the ARS, this opens the possibility of expanding the therapeutic capabilities of an ARS beyond what has been previously demonstrated (Fabiilli et al. 2013). US could be used to modulate the porosity or mechanical properties of ARSs containing single emulsions to influence cell invasion into the ARS. Alternatively, single emulsions could be used to deliver therapeutic gases within the ARS (Faithfull 1992). Release of two distinct payloads could be achieved by formulating an ARS with two different double emulsion formulations. For example, as seen in FIG. 7D, the ADV thresholds in an ARS containing PFP or PFH double emulsion is 2.5 MPa and 3 MPa, respectively, at 3 cycles. Therefore one payload could be released first at the lower acoustic threshold while a second payload could be released at a higher acoustic threshold—thus enabling temporal control of multiple payload release. Though not investigated in this work, the use of different US frequencies could also be used to tune different release thresholds (Kripfgans 2002; Schad and Hynynen 2010; Martz et al. 2011). Other modifications to the droplet formulations including differential size distributions could further increase the separation in threshold for temporal control. Spatial control of ADV/IC and payload release is also an inherent feature of an ARS due to the use of focused US as the means to interact with the sonosensitive emulsion, compared to studies where unfocused US has been used to facilitate drug release (Huebsch et al. 2014). The use of megahertz frequency US to trigger ADV enables patterning at submillimeter resolution within an ARS. Additionally, ADV thresholds of the ARSs ranged from approximately 1.5 to 3 MPa peak rarefactional pressure, which is within the output range of clinical diagnostic US scanners (i.e., at 2.5 MHz, 3 MPa is equivalent to a mechanical index of 1.9 which is the current upper limit set by the United States Food and Drug Administration). Clinically-approved, therapeutic US systems, typically operating in the 1-3 MHz range, could be used to generate ADV at higher acoustic pressures within an ARS.

Cell adherence and viability can be impacted by US capable of generating ADV and IC. ADV adjacent to adherent cells can cause detachment (Ohl et al. 2006) while an 80% decrease in cell number was observed for cells in the presence of bubbles undergoing IC (Ward et al. 1999). It was previously demonstrated that the viability of cells encapsulated in an ARS was not impacted by high amplitude US used to generate ADV within an ARS, when measured 2 days after ADV exposure (Fabiilli et al. 2013). However, this prior study investigated only one acoustic condition (i.e., 6 MPa peak rarefactional pressure at 3.5 MHz, MI=3.2) and the presence of IC was not measured. In this work, the viability of cells contained in the ARS was not affected by acoustic pressures up to 2 MPa but decreased to 60% when exposed to an acoustic pressure of 8 MPa, which generated sustained IC. As seen in FIG. 7, some of the ADV thresholds occurred at pressures less than 2 MPa. Additionally, the use of higher frequency US could reduce the acoustic bioeffects stemming from IC, though at the expense of depth penetration. Beyond viability, the impact of ADV and IC on cellular proliferation, differentiation, apoptosis, as well as cytokine production in an ARS are also critically important, but were outside of the scope of this work. Statistically significant differences within each subfigure of FIG. 7 are detailed in Tables 2-5, below.

TABLE 2

Results of multiple comparison post-hoc testing, using the Tukey Kramer method, for the data in FIG. 7. Results of Tukey-Kramer Test for FIG. 7A

| Group | Single Emulsion PFC | Cycles | Parameter | Pressure (Mpa) | Groups that are Statistically Different |
|---|---|---|---|---|---|
| 1 | PFP | 3 | ADV | 1.71 ± 0.18 | 3 |
| 2 | PFP | 3 | IC - Low | 1.75 ± 0.18 | 3, 11 |
| 3 | PFP | 3 | IC - High | 3.02 ± 0.31 | 1, 2 |
| 4 | PFP | 6 | ADV | 1.89 ± 0.24 | 6 |
| 5 | PFP | 6 | IC - Low | 1.88 ± 0.14 | 6 |
| 6 | PFP | 6 | IC - High | 3.34 ± 0.12 | 4, 5 |
| 7 | PFP | 13 | ADV | 1.82 ± 0.13 | |
| 8 | PFP | 13 | IC - Low | 1.86 ± 0.09 | |
| 9 | PFP | 13 | IC - High | 2.10 ± 0.10 | |
| 10 | PFH | 3 | ADV | 2.41 ± 0.20 | 12, 16 |
| 11 | PFH | 3 | IC - Low | 2.98 ± 0.24 | 2, 12 |
| 12 | PFH | 3 | IC - High | 3.98 ± 0.20 | 10, 11 |
| 13 | PFH | 6 | ADV | 2.08 ± 0.06 | 15 |
| 14 | PFH | 6 | IC - Low | 2.11 ± 0.07 | 15 |
| 15 | PFH | 6 | IC - High | 3.03 ± 0.24 | 13, 14 |
| 16 | PFH | 13 | ADV | 1.92 ± 0.16 | 10, 18 |
| 17 | PFH | 13 | IC - Low | 2.30 ± 0.21 | 18 |
| 18 | PFH | 13 | IC - High | 2.89 ± 0.09 | 16, 17 |

TABLE 3

Results of multiple comparison post-hoc testing, using the Tukey Kramer method, for the data in FIG. 7. Results of Tukey-Kramer Test for FIG. 7B

| Group | Fibrin Concentration (mg/mL) | Cycles | Parameter | Pressure (Mpa) | Groups that are Statistically Different Result of T-Test |
|---|---|---|---|---|---|
| 1 | 3 | 3 | ADV | 2.00 ± 0.14 | 3 |
| 2 | 3 | 3 | IC - Low | 1.81 ± 0.15 | 3 |
| 3 | 3 | 3 | IC - High | 3.47 ± 0.30 | 1, 2 |
| 4 | 3 | 13 | ADV | 1.97 ± 0.10 | 16 |
| 5 | 3 | 13 | IC - Low | 1.89 ± 0.07 | 11, 17 |
| 6 | 3 | 13 | IC - High | 1.97 ± 0.10 | |
| 7 | 5 | 3 | ADV | 2.41 ± 0.20 | 9 |
| 8 | 5 | 3 | IC - Low | 2.98 ± 0.24 | 9 |
| 9 | 5 | 3 | IC - High | 3.98 ± 0.20 | 7, 8 |
| 10 | 5 | 13 | ADV | 1.92 ± 0.17 | 12 |
| 11 | 5 | 13 | IC - Low | 2.30 ± 0.15 | 5 |
| 12 | 5 | 13 | IC - High | 2.90 ± 0.15 | 10 |
| 13 | 10 | 3 | ADV | 2.83 ± 0.16 | 15 |
| 14 | 10 | 3 | IC - Low | 3.08 ± 0.28 | 15 |
| 15 | 10 | 3 | IC - High | 5.24 ± 0.47 | 13, 14 |
| 16 | 10 | 13 | ADV | 2.60 ± 0.18 | 4, 18 |
| 17 | 10 | 13 | IC - Low | 2.55 ± 0.22 | 5, 18 |
| 18 | 10 | 13 | IC - High | 3.28 ± 0.16 | 16, 17 |

TABLE 4

Results of multiple comparison post-hoc testing, using the Tukey Kramer method, for the data in FIG. 7.
Results of Tukey-Kramer Test for FIG. 7C

| Group | Shell Material | Cycles | Parameter | Pressure (Mpa) | Groups that are Statistically Different Result of T-Test |
|---|---|---|---|---|---|
| 1 | Lipid | 3 | ADV | 2.41 ± 0.20 | 3 |
| 2 | Lipid | 3 | IC - Low | 2.98 ± 0.24 | 3, 11, 20 |
| 3 | Lipid | 3 | IC - High | 3.98 ± 0.20 | 1, 2 |
| 4 | Lipid | 6 | ADV | 2.08 ± 0.06 | 6, 22 |
| 5 | Lipid | 6 | IC - Low | 2.11 ± 0.07 | 6, 14, 23 |
| 6 | Lipid | 6 | IC - High | 3.10 ± 0.09 | 4, 5 |
| 7 | Lipid | 13 | ADV | 1.92 ± 0.16 | 9 |
| 8 | Lipid | 13 | IC - Low | 2.30 ± 0.21 | 17, 26 |
| 9 | Lipid | 13 | IC - High | 2.90 ± 0.15 | 7 |
| 10 | BSA | 3 | ADV | 2.55 ± 0.32 | 11, 12 |
| 11 | BSA | 3 | IC - Low | 4.44 ± 0.13 | 2, 10, 12, 14 |
| 12 | BSA | 3 | IC - High | 6.68 ± 0.14 | 10, 11 |
| 13 | BSA | 6 | ADV | 2.52 ± 0.37 | 15 |
| 14 | BSA | 6 | IC - Low | 3.36 ± 0.09 | 5, 11, 15, 23 |
| 15 | BSA | 6 | IC - High | 4.92 ± 0.11 | 13, 14 |
| 16 | BSA | 13 | ADV | 2.38 ± 0.41 | 17, 18 |
| 17 | BSA | 13 | IC - Low | 4.13 ± 0.33 | 8, 16 |
| 18 | BSA | 13 | IC - High | 5.71 ± 0.35 | 16, 17 |
| 19 | Pluronic F68 | 3 | ADV | 3.70 ± 1.01 | 21 |
| 20 | Pluronic F68 | 3 | IC - Low | 4.73 ± 0.37 | 2, 21 |
| 21 | Pluronic F68 | 3 | IC - High | 6.95 ± 0.51 | 19, 20 |
| 22 | Pluronic F68 | 6 | ADV | 2.58 ± 0.25 | 4, 23, 24 |
| 23 | Pluronic F68 | 6 | IC - Low | 4.27 ± 0.07 | 5, 14, 22, 24 |
| 24 | Pluronic F68 | 6 | IC - High | 5.83 ± 0.23 | 22, 23 |
| 25 | Pluronic F68 | 13 | ADV | 2.51 ± 0.50 | 26, 27 |
| 26 | Pluronic F68 | 13 | IC - Low | 4.24 ± 0.22 | 8, 25, 27 |
| 27 | Pluronic F68 | 13 | IC - High | 5.67 ± 0.23 | 25, 26 |

TABLE 5

Results of multiple comparison post-hoc testing, using the Tukey Kramer method, for the data in FIG. 7.
Results of Tukey-Kramer Test for FIG. 7D

| Group | Double Emulsion PFC | Cycles | Parameter | Pressure (Mpa) | Groups that are Statistically Different Result of T-Test |
|---|---|---|---|---|---|
| 1 | PFP | 3 | ADV | 2.48 ± 0.10 | 2, 3, 10 |
| 2 | PFP | 3 | IC - Low | 4.55 ± 0.09 | 1, 3, 11 |
| 3 | PFP | 3 | IC - High | 6.66 ± 0.15 | 1, 2 |
| 4 | PFP | 6 | ADV | 2.11 ± 0.15 | 5, 6, 13 |
| 5 | PFP | 6 | IC - Low | 3.78 ± 0.71 | 4, 6, 14 |
| 6 | PFP | 6 | IC - High | 6.42 ± 0.78 | 4, 5 |
| 7 | PFP | 13 | ADV | 1.68 ± 0.36 | 8, 9 |
| 8 | PFP | 13 | IC - Low | 3.63 ± 0.14 | 7, 9, 17 |
| 9 | PFP | 13 | IC - High | 5.11 ± 0.32 | 7, 8 |
| 10 | PFH | 3 | ADV | 3.18 ± 0.12 | 1, 11, 16 |
| 11 | PFH | 3 | IC - Low | 7.05 ± 0.26 | 2, 10 |
| 12 | PFH | 3 | IC - High | | |
| 13 | PFH | 6 | ADV | 2.90 ± 0.11 | 4, 14 |
| 14 | PFH | 6 | IC - Low | 6.20 ± 0.37 | 5, 13 |
| 15 | PFH | 6 | IC - High | | |
| 16 | PFH | 13 | ADV | 2.17 ± 0.10 | 10, 17 |
| 17 | PFH | 13 | IC - Low | 4.38 ± 0.27 | 8, 16 |
| 18 | PFH | 13 | IC - High | | |

The physical stability of the emulsion used to dope an ARS is relevant to the stability of the ARS as a whole and can impact the ability of US to interact with the ARS. ARSs doped with PFH emulsions displayed less spontaneous (i.e., in the absence of US) bubble formation than ARSs doped with PFP emulsions. The millimeter size bubbles formed in the ARS doped with PFP likely formed via coalescence of multiple smaller bubbles. Also, subsequent in-gassing may have occurred as the ARS, which was prepared with degassed fluids, was placed into a cell culture incubator at atmospheric gas saturation with 5% carbon dioxide. Additional nucleation of dissolved gas within the PFC could also have occurred as the ARS warmed from room temperature to 37° C. It is hypothesized that the higher boiling point of PFH versus PFP imparts greater stability. Previous studies with PFP emulsions indicate that these droplets are stable at 37° C. (Fabiilli et al. 2013), though few if any studies explored the stability at 37° C. for one week or in a matrix like a fibrin scaffold. Additionally, PFP emulsions displayed greater stability in DMEM versus in an ARS. Within an ARS, the fibrin surrounding each droplet may be exerting tension on the droplet, or effectively lowering the interfacial tension, which would destabilize the PFC droplet.

Encapsulation of FSS within the $W_1$ phase of the emulsion hindered its release from the ARS when compared to non-emulsified FSS FIG. 12. However, despite exhibiting greater stability, the retention of FSS was similar for ARSs doped with PFP and PFH double emulsions. The higher bubble density within ARSs doped with PFP double emulsion could impact the diffusivity of FSS through the ARS. Overall, the greater stability of the ARS with PFH double emulsion makes this composition better suited for controlled release or in vivo implantation since any spontaneously formed bubbles would prevent US from penetrating the ARS. In additional to spontaneous vaporization, the population of PFC droplets may be shifting toward larger sizes, due to droplet coalescence or Ostwald ripening. This would cause sub-micron size droplets that are initially below the sizing range of the Coulter Counter to enter the detectable range (i.e., 1-30 μm), thus causing an increase in the droplet concentration and volume percentage. The osmotic imbalance between the $W_1$ phase, which contained FSS at 1 mg/mL, and the surrounding environment (i.e., the fibrin scaffold and overlying DMEM), could have contributed to the increase in volume percentage of the emulsion within the ARS doped with PFH double emulsion.

CONCLUSIONS

In this study, the interactions of US with droplets and associated bubbles occurring in sonosensitive hydrogels was demonstrated. ADV and IC thresholds were modulated by modifying ARS parameters such as fibrin concentration, emulsion shell material, PFC core, emulsion structure, and the number of acoustic cycles. ADV occurred within an ARS with minimal effects on cell viability while IC caused decreases in viability. ARSs doped with PFH emulsions displayed better physical stability and less spontaneous bubble formation than ARSs doped with PFP emulsions. Non-selective payload release was minimal for both ARS compositions tested. Based on this study, the recommended ARS composition for GF delivery consists of 5 or 10 mg/mL fibrin with a double emulsion containing PFH or an admixture of PFP/PFH.

For the US exposure, a higher number of acoustic cycles is also recommended. Thus, a pulse repetition frequency of from about 1 Hz to about 50 Hz is contemplated.

Example 3

The goals of this study were to 1) evaluate the biocompatibility of the ARS when implanted subcutaneously; 2) determine the extent to which the fibrin component of the ARS degrades when implanted subcutaneously; and 3)

assess morphological changes of the ARS. Blood vessel formation in the ARSs was also characterized since effective tissue expansion is dependent on generating new vasculature to provide oxygen and nutrients to the growing skin.

Materials and Methods

Double Emulsion Preparation and Characterization

Double emulsions with a water-in-perfluorocarbon-in-water ($W_1/PFC/W_2$) structure were prepared by modifying a previous method [1]. Briefly, a triblock fluorosurfactant, consisting of Krytox 157FSH (CAS #51798-33-5, DuPont, Wilmington, Del., USA) and polyethylene glycol (MW: 1000, CAS #: 24991-53-5, Alfa Aeser, Ward Hill, Mass. USA), was dissolved in 1 g of perfluorocarbon (PFC) at 2% (w/w). The PFC phase consisted of perfluoropentane (subsequently referred to as "$C_5$", CAS #: 678-26-2, Strem Chemicals, Newburyport, Mass. USA), perfluorohexane (subsequently referred to as "$C_6$", CAS #: 355-42-0, Strem Chemicals), or a 1:1 (w/w) $C_5:C_6$ admixture. The PFC solution was then combined, in a 2:1 volumetric ratio, with an aqueous solution of Alexa Fluor 680-labeled dextran (MW: 10,000 Da, Life Technologies, Grand Island, N.Y. USA) reconstituted at 0.625 mg/mL in Dulbecco's Phosphate-Buffered Saline (DPBS, Life Technologies). This concentration of dextran was chosen to prevent self-quenching of the fluorophore. The phases were sonicated (CL-188, QSonica, LLC, Newton, Conn. USA) for 30 seconds while on ice. The resulting primary emulsion, with a water-in-PFC ($W_1/PFC$) structure, was added drop wise to a solution of 50 mg/mL Pluronic F68 (CAS #9003-11-6, Sigma-Aldrich, St. Louis, Mo. USA) in DPBS and stirred with a magnetic stir bar at 700 RPM for 2 minutes while on ice. The particle size of the resulting coarse double emulsion ($W_1/PFC/W_2$) was reduced using a homogenizer (T10, IKA Works Inc., Wilmington, N.C. USA). Emulsions with "large" and "small" droplet distributions were processed at approximately 7.9 kRPM and approximately 29.9 kRPM, respectively. Blank emulsions were prepared as described above with only DPBS as the $W_1$ phase.

Acoustically-Responsive Scaffold (ARS) Fabrication

ARSs were prepared using 10 mg/mL clottable protein by first combining bovine fibrinogen (Sigma-Aldrich, 75% total protein, 96% clottable protein)—dissolved in degassed (36% $O_2$ saturation) Dulbecco's modified Eagle's medium (DMEM, Life Technologies)—with bovine thrombin (20 U/mL, Thrombin-JMI, King Pharmaceuticals, Bristol, Tenn., USA), 0.025 U/mL aprotinin (Sigma-Aldrich), and 1% (v/v) emulsion.

Ultrasound (US) Exposure

All acoustic exposures were conducted using the following setup. A calibrated transducer (2.5 MHz, H108, f-number=0.83, focal length=50 mm, Sonic Concepts, Inc., Bothell, Wash. USA) was driven by pulsed waveforms generated using a dual channel function generator (33500B, Agilent Technologies, Santa Clara, Calif. USA), amplified by a gated radio frequency amplifier (GA-2500A Ritec Inc, Warwick, R.I. USA), and passed through a matching circuit (H108_3MN, Sonic Concepts) to reduce impedance between the transducer and amplifier. Waveform gating was realized using the second channel of the function generator. All generated and amplified signals were monitored with an oscilloscope (HD04034, Teledyne LeCroy, Chestnut Ridge, N.Y. USA). All acoustic exposures were done with the following parameters unless otherwise stated in the figure caption: 8 MPa peak rarefactional pressure, 13 acoustic cycles, and 100 Hz pulse repetition frequency (PRF). This corresponds to a spatial peak time average intensity of 86.4 $mW/cm^2$.

In Vivo Controlled Release of Dextran

This in vivo research was conducted with approval of the Institutional Animal Care & Use Committee at the University of Michigan. Female BALB/c mice (n=22, 18-21 g, Charles River Laboratories, Wilmington, Mass., USA) were anesthetized with isoflurane (5% for induction and 1.5% for maintenance). The lower dorsal hair was removed by shaving and depilatory cream (Nair, Church & Dwight Co, Ewing, N.J. USA); the skin was sterilized with betadine surgical scrub (Purdue Products L.P., Stamford, Conn. USA). The ARS mixture (0.25 mL per implant) was then injected subcutaneously using a 20 gauge needle (Becton Dickinson, Franklin Lakes, N.J., USA) at two locations with the dorsal region and allowed to polymerize for 2 minutes prior to removal of the needle. The ARS mixture contained 1% (v/v) dextran-loaded emulsion with either 1:1 $C_5:C_6$ or $C_6$ as the PFC phase. The mice were allowed to recover following implantation. Fibrin scaffolds without emulsion, but containing dextran, were injected as control implants. Blank scaffolds (i.e., without emulsion and dextran) were injected as sham controls.

Each mouse was anesthetized with isoflurane and placed in a prone position. US coupling gel (MediChoice, Owens & Minor, Mechanicsville, Va. USA) was applied to the implant region. A coupling cone (C106, Sonic Concepts) was placed on the US transducer, filled with degassed water (30-36% $O_2$ saturation), and the water was sealed in by Tegaderm film (3M Health Care, St. Paul, Minn. USA). The transducer was rastered across the implant for 2 min. For each mouse, US was applied daily to only one scaffold beginning one day after implantation for a period of 10 days. The scaffolds receiving US treatment (i.e., left or right implant) were randomized for all mice.

In Vivo Fibrin Degradation

ARSs containing 1% (v/v) blank emulsion, with $C_6$ as the PFC phase, and Alexa Fluor 647-labeled labeled fibrinogen (0.125 mg/mL) were prepared, injected into female BALB/c mice (n=10), and exposed to US as described previously. Fibrin scaffolds without emulsion, but containing Alexa Fluor 647-labeled fibrinogen, were injected as control implants. Blank scaffolds (i.e., without emulsion and labeled fibrinogen) were injected as sham controls.

IVIS Imaging

The mice were anesthetized with isoflurane and imaged with an IVIS Spectrum Preclinical In Vivo Imaging System (f/4, field of view=19.4 cm, Perkin Elmer, Houston, Tex. USA) at the University of Michigan Center for Molecular Imaging to quantify the fraction of dextran or fibrinogen released from the implants [2]. The mice were imaged on day 0 (i.e., the day of implantation), 1 (i.e., the first day of US exposure), 2, 3, 4, 7, and 10. On days 1-10, the mice were imaged after US exposure. For the dextran release study, the fluorophore signal was collected using an excitation filter of 675 nm and emission filters ranging from 720 to 780 nm. To account for autofluorescence, a sequence of background signals was collected using an excitation filter of 605 nm and emission filters ranging from 660 to 780 nm. For the fibrin degradation study, the fluorophore signal was collected using an excitation filter of 640 nm and emission filters ranging from 680 to 740 nm. To account for autofluorescence, a sequence of background signals was collected using an excitation filter of 570 nm and emission filters ranging from 620 to 740 nm. Spectral unmixing was performed on the dextran and fibrinogen data sets in Living Image software (Perkin Elmer), according to the manufacturer's instructions, using the fluorophore and autofluorescence (background) images. Following unmixing, equally sized regions of interest (ROIs, 1.25 cm diameter) corresponding to each implant, were drawn and the average radiant efficiency ([photons/s/cm$^2$/sr]/[μW/cm$^2$]) was calculated. The size of the ROI, f/stop, and field of view were sufficiently large to encompass any lateral and axial diffusion of the dextran after release. For each implant, the average radiant efficiency on days 1-10 was normalized by the day 0 measurement, thus accounting for any differences in the amount of fluorophore initially loaded.

Histology

For the in vivo fibrin degradation study, mice were euthanized on day 3 and day 10 post implantation. ARSs were retrieved and fixed overnight in aqueous buffered zinc formalin (CAS #50-00-0, Formalde-Fresh, Fisher Scientific). Implants were then transferred to 70% ethanol until they were processed and embedded in paraffin at the University of Michigan Microscopy & Image Analysis Laboratory. The paraffin-embedded tissues were cut into 5 μm thick serial sections and placed on pre-cleaned glass slides (Fisherbrand Superfrost Plus, Fisher Scientific) for histological analysis. Tissue sections were stained with Modified Harris Formulation hematoxylin (Ricca Chemical Company, Arlington, Tex. USA) and aqueous eosin Y solution (0.25% (w/v) in 57% (v/v) alcohol, Sigma-Aldrich) (H&E) to visualize the overall tissue morphology. Immunostaining of mice-derived blood vessels was performed using a rabbit anti-mouse CD31 primary antibody (ab28364, Abcam, Cambridge, Mass. USA) combined with a goat anti-rabbit secondary labeled polymer-horseradish peroxidase conjugate (Envision+System-HRP (DAB), Dako North America, Inc., Carpinteria, Calif. USA), as described previously [3, 4]. Negative controls, involving staining with a rabbit IgG polyclonal isotype control (ab27478, Abcam) as the primary antibody or staining with the secondary antibody only, confirmed the specificity of the CD31 staining. Tissue sections were visualized and photographed with a Leica DMRB light microscope (Leica Microsystems, Inc., Buffalo Grove, Ill. USA). Three tissue sections from each implant—with five images per tissue section—were analyzed manually for blood vessel formation per unit area as well as thickness of the granulation layer. Blood vessel counting was done, in a blinded manner, by three separate individuals. Blood vessels were identified in CD31-stained tissues at 20× magnification by defined lumens and complete enclosure of the lumen.

Results

Figure 13:
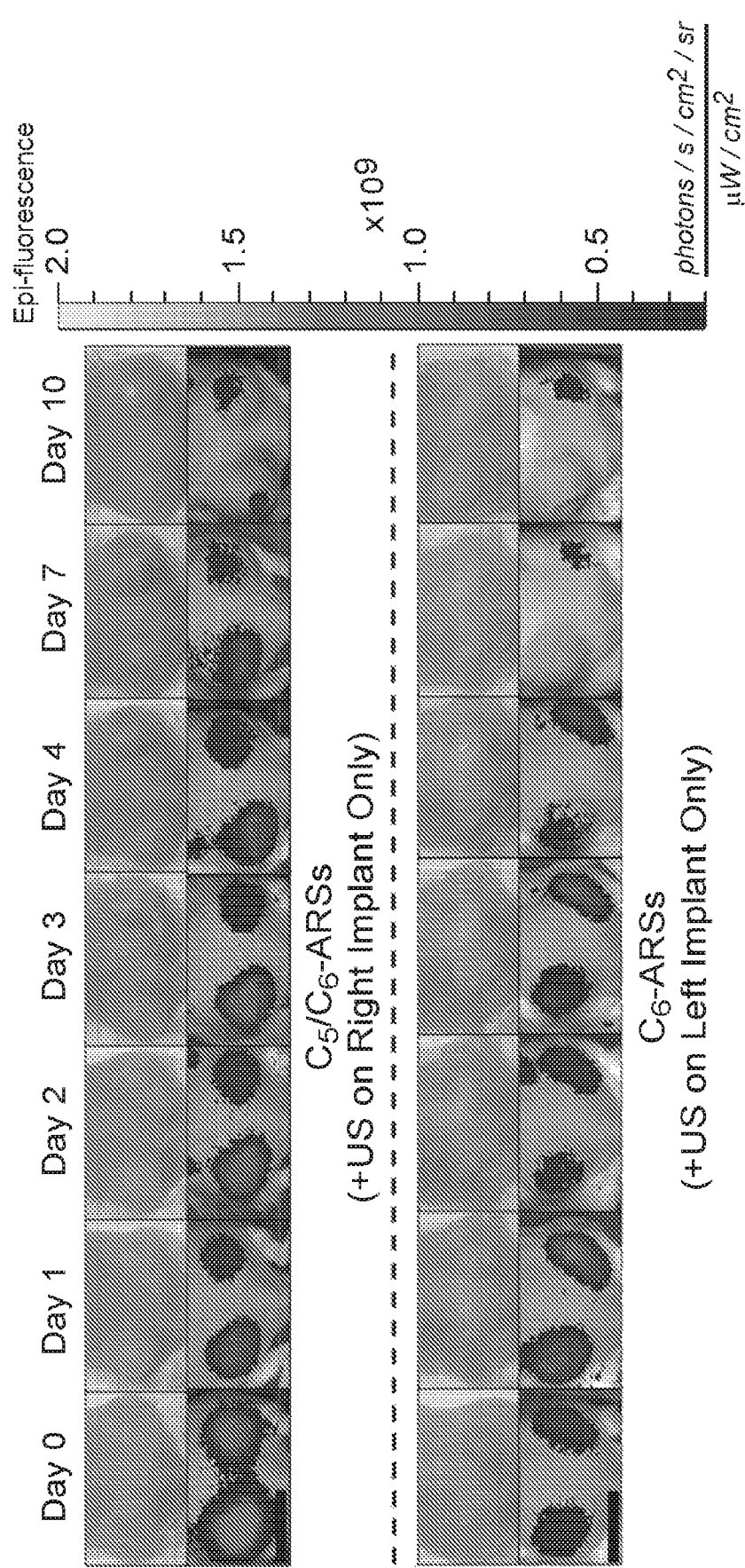
FIG. 13 shows longitudinal images, visible and fluorescence, of two mice—each with two subcutaneously implanted ARSs (top: $C_5/C_6$-ARSs, bottom: $C_6$-ARSs). The ARSs were implanted on day 0 and US applied daily starting on day 1 to the right ($C_5/C_6$-ARSs) or left ($C_6$-ARSs) implant. The colormap is quantitatively indicative of the dextran concentration remaining in the ARS. Scale bar=1 cm.

FIG. 13 shows longitudinal photographs and fluorescence images of mice with implanted $C_5/C_6$- and $C_6$-ARSs. Over the 10 day study, the ARSs exhibited a slight volumetric expansion, which was more clearly evident for the $C_5/C_6$-ARSs.

Figure 14:
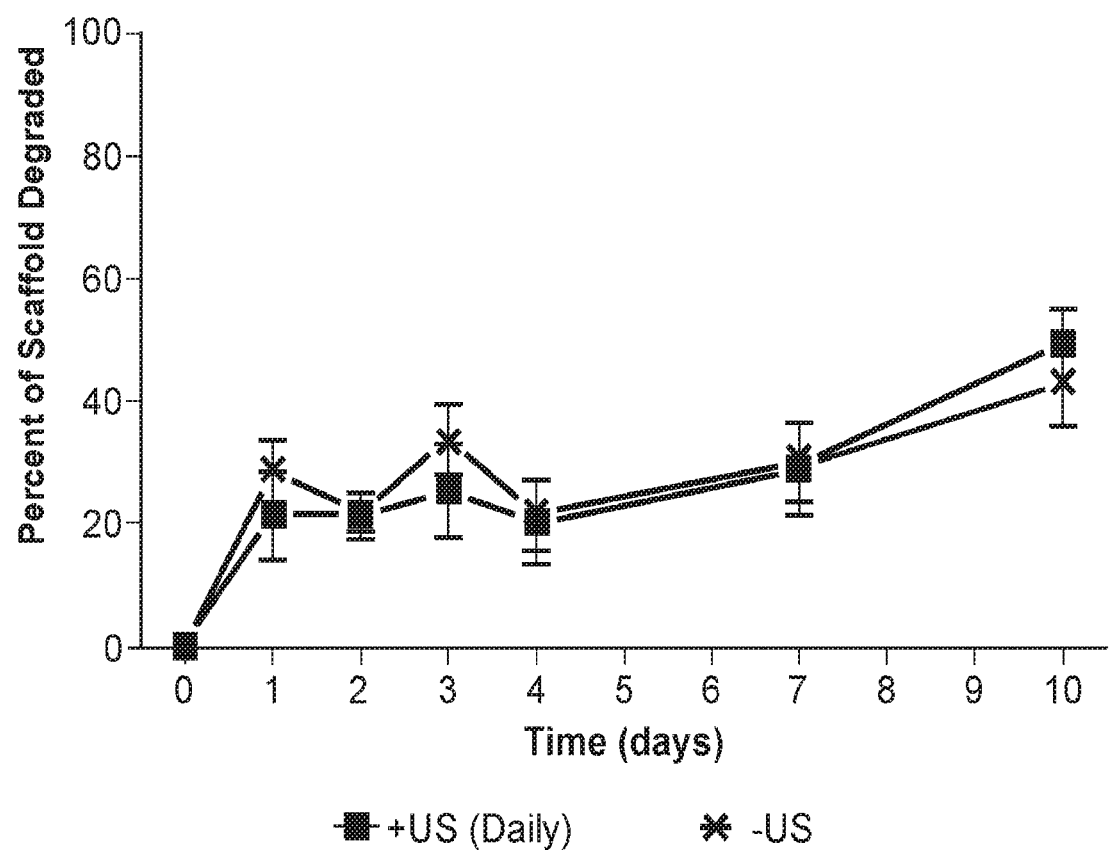
FIG. 14 shows in vivo fibrin degradation of ARSs with blank $C_6$ emulsion. ARSs were exposed to +US (daily beginning on day 1) or −US using the same setup/parameters described previously. All ARSs had a fibrin concentration of 10 mg/mL, were implanted one day prior to the first acoustic exposure, and had a volume of 0.25 mL. All data is represented as mean±standard error of the mean for n=10 implants/condition.

The degradation rate for the implanted ARSs, evaluated using fluorescence imaging, is also shown in FIG. 14. No differences were observed between −US and +US in terms of degradation rate (p=0.4, slope of −US: 2.8 [−0.1, 5.7], slope of +US: 3.6 [1.5, 5.8]) or the amount of ARS degraded at any time point. By day 10, the fraction of degradation was 42.8±6.9% and 49.3±5.4% for −US and +US, respectively.

Figure 15:
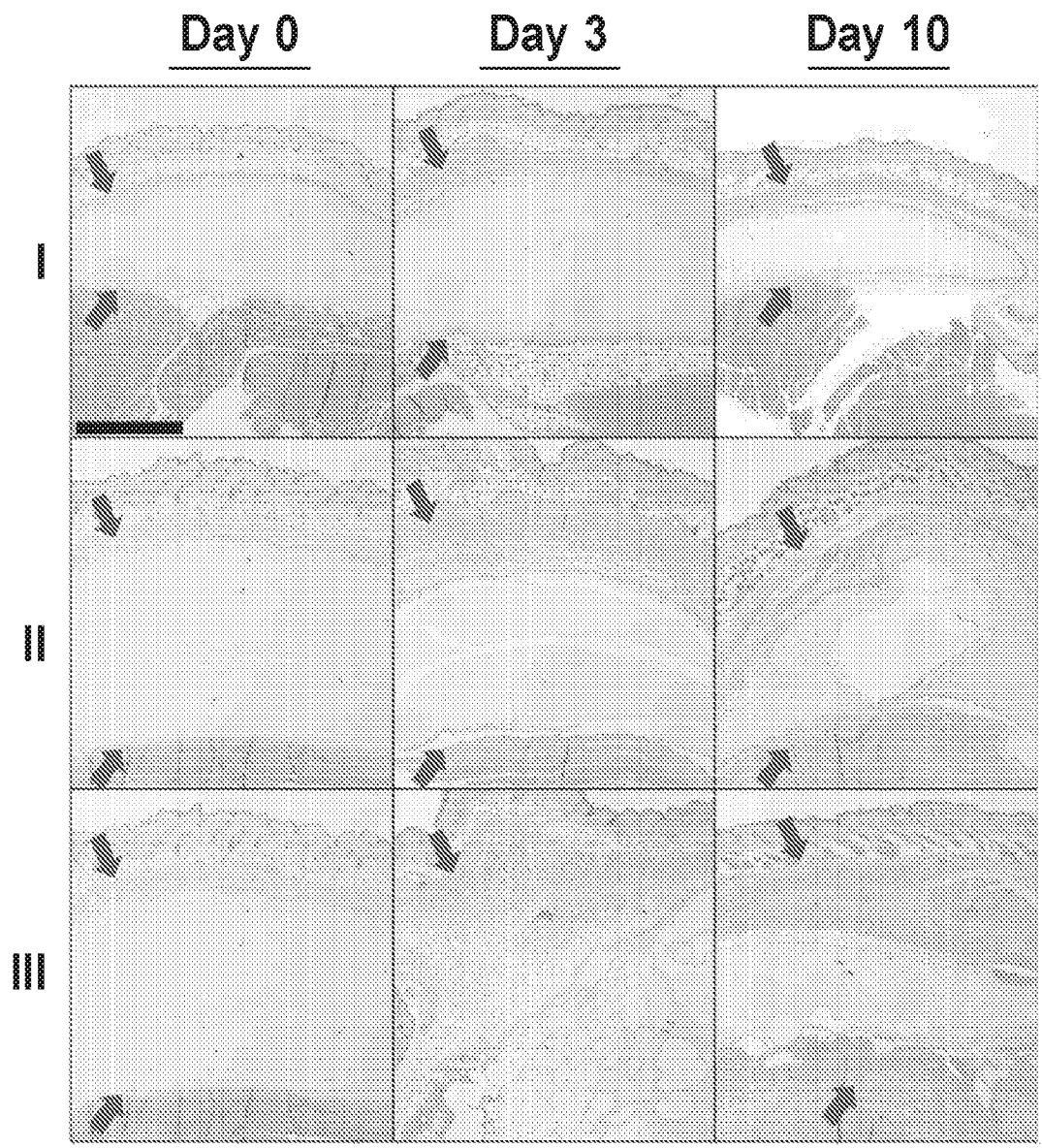
FIG. 15 shows H&E images of implanted (I) fibrin scaffolds, (II) ARS not exposed to US (i.e., −US), and (III) ARS exposed to daily US beginning on day 1 (i.e., +US) on days 0, 3, and 10 at 5× magnification. The +/−US images of the ARSs are from contralateral implants within the same mouse. The green and red arrows denote the skin/implant interface and implant/(adipose or muscle) interface, respectively. Scale bar=1 mm.

H&E images of fibrin and $C_6$-ARS implants are displayed in FIG. 15. All implants appeared similar on day 0, with no cell invasion and implant degradation. Cellular infiltration was observed on days 3 and 10 for both fibrin and ARSs. For ARSs, there was a difference in morphology between the +/−US conditions 3 days after implantation. The +US ARS had large ruptures within the scaffold, presumably caused by droplet vaporization induced by the US exposures beginning on day 1. The morphology of the −US ARS condition began to approach that of the +US ARS condition 10 days after implantation, as is seen with the gas pocket observed in the H&E section (FIGS. 3A and 3B, Day 10-II).

Figure 16:
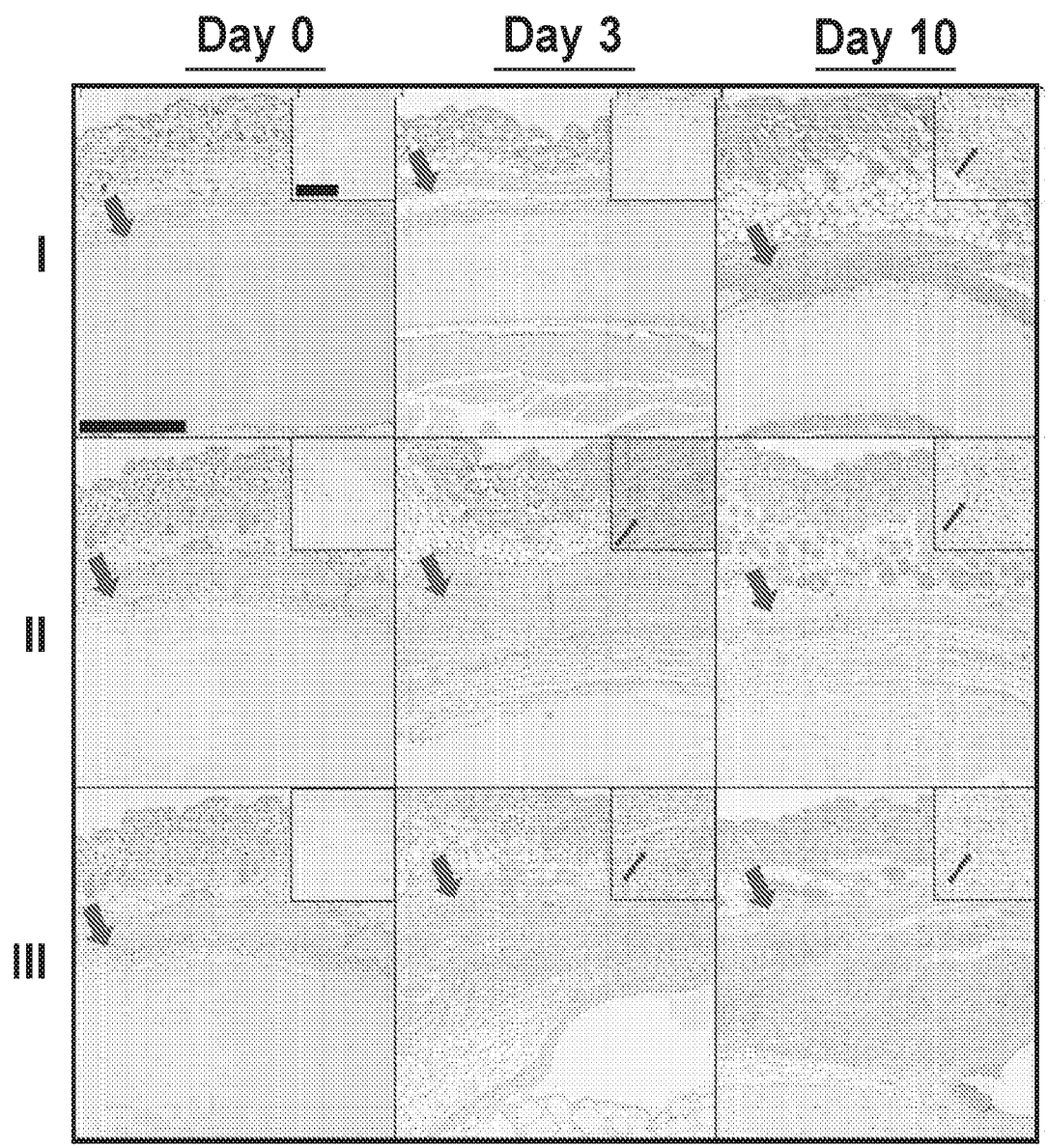
FIG. 16 shows CD31, with hematoxylin counterstain, images of implanted (I) fibrin scaffolds, (II) $C_6$-ARSs not exposed to US (i.e., −US), and (III) C6-ARSs exposed to daily US (beginning on day 1 (i.e., +US)) on days 0, 3, and 10 at 10× magnification. The +/−US images of the ARSs are from contralateral implants within the same mouse. Inset images (63× magnification) are zoomed in within the implant to highlight blood vessel invasion, or lack thereof. The green arrows denote the skin/implant interface while the blue arrows denote blood vessels. Large scale bar=0.5 mm and the small scale bar=0.1 mm.
Figure 17A:
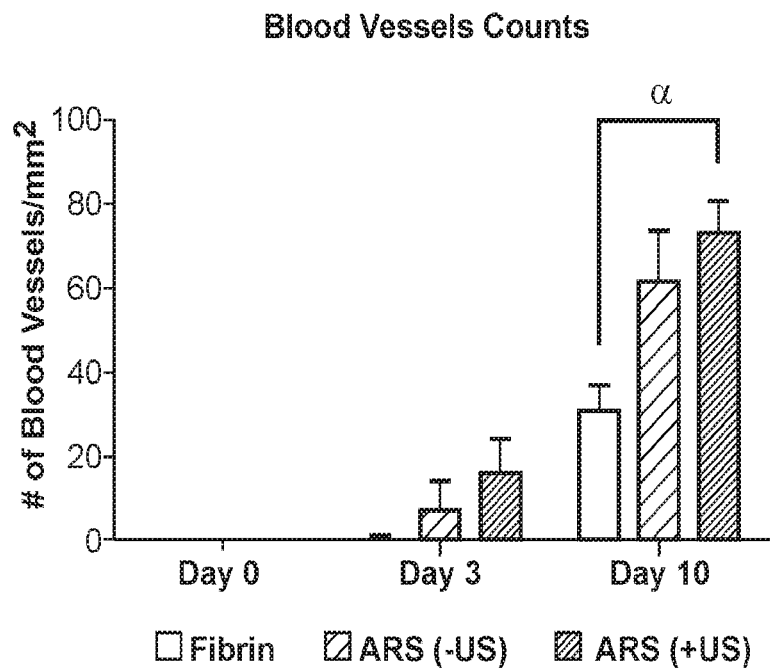
FIGS. 17A-17B shows quantification of (a) blood vessel density from CD31-stained images and (b) granulation layer thickness from H&E stained images of fibrin scaffolds, $C_6$-ARSs not exposed to US (i.e., −US), and $C_6$-ARSs exposed to daily US beginning on day 1 (i.e., +US). All data is represented as mean±standard error of the mean for n=9. α denotes statistically significant differences (p<0.05).

As seen in FIG. 16, blood vessel in-growth into the fibrin and ARS implants was evaluated immunohistochemically. As expected, no blood vessels were observed in any scaffold on day 0. Blood vessels were observed in the scaffolds beginning on day 3, with a higher density and larger vessels evident by day 10. Blood vessel density (i.e., number of blood vessels per area) within each scaffold is quantified in FIG. 17A. Blood vessel density increased from day 3 (1.3±0.5, 8.4±7.1, and 16.9±8.8 vessels/mm$^2$) to day 10 (25.5±4.5, 62.1±12.3, and 73.8±7.1 vessels/mm$^2$) for fibrin, −US ARSs, and +US ARSs, respectively. On day 10, the blood vessel density within an ARS exposed to US was significantly higher than in a fibrin scaffold. Although not statistically significant (p=0.057), blood vessel density in the −US ARSs was trending higher than in fibrin. The thickness of the granulation layer in each type of implant is quantified in FIG. 17B. The thickness of the granulation layer increased with time, with the greatest thickness observed on day 10 (141.5±7.8, 377.0±29.2, and 376.4±28.7 μm for fibrin, −US ARS, and +US ARS, respectively). Significant differences were observed on day 10 between fibrin and both ARS conditions.

Discussion

Figure 17B:
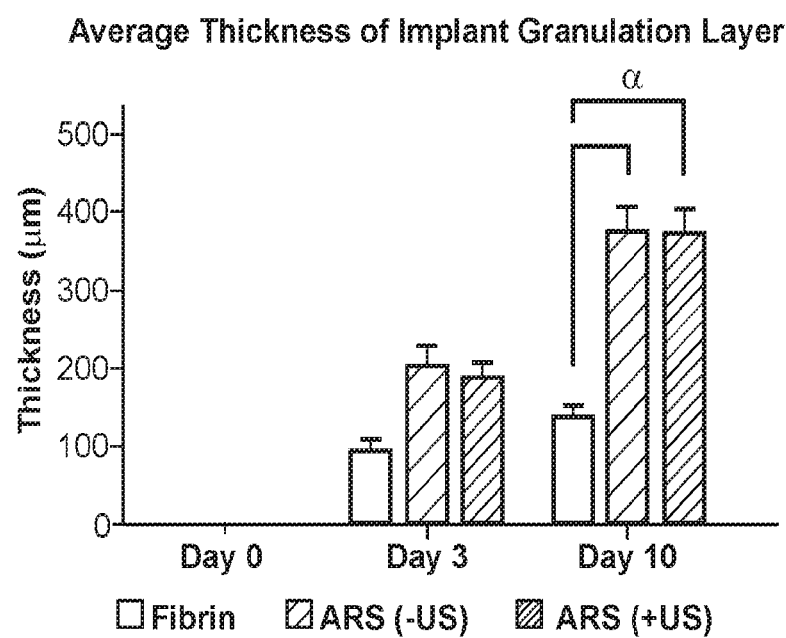

Greater blood vessel formation and granulation layer thickness were observed in ARSs versus fibrin by day 10 (FIGS. 17A-17B), which suggests that vascularization and cell invasion was enhanced by the presence of C6 emulsion in the fibrin matrix. PFCs are known for having high gas solubility, especially oxygen, with lower boiling point PFCs exhibiting higher oxygen solubilization [5-7]. As such, cells co-encapsulated in hydrogel scaffolds with PFC display higher viability than cells encapsulated without PFC [8, 9]. The PFC within the ARS may be serving as oxygen depots that could attract cells into the ARS. Previous work has shown no statistical difference in blood vessel formation between a conventional fibrin scaffold and a fibrin scaffold loaded with poly(lactic-co-glycolic) acid (PLGA) particles [10]. This suggests that the PFC within the ARS is the likely cause of enhanced angiogenesis. In addition, the presence of emulsion within the ARS may have facilitated cell invasion into the ARS as seen in FIG. 17B. This is demonstrated by H&E images of tissue samples taken on day 3 and 10 (FIG. 15), where greater cell invasion is seen in ARSs versus fibrin implants. It is important to note that the granulation layer mentioned in this work is not a fibrous capsule, as fibrous capsules are chronic and impermeable to cells [11]. Additionally, the morphology of the granulation layer observed here is similar to the morphology seen in prior studies [12]. Overall, the finding that ARSs increase vascularization is interesting, given that no growth factors were released in these experiments, and potentially useful in future studies involving angiogenesis.

REFERENCES CITED IN EXAMPLE 3

[1] Fabiilli M L, Lee J A, Kripfgans O D, Carson P L, Fowlkes J B. Delivery of water-soluble drugs using acoustically triggered perfluorocarbon double emulsions. Pharm Res. 2010; 27:2753-65.

[2] Wolbank S, Pichler V, Ferguson J C, Meinl A, van Griensven M, Goppelt A, et al. Non-invasive in vivo tracking of fibrin degradation by fluorescence imaging. Journal of Tissue Engineering and Regenerative Medicine. 2015; 9:973-6.

[3] Nor J E, Peters M C, Christensen J B, Sutorik M M, Linn S, Khan M K, et al. Engineering and characterization of functional human microvessels in immunodeficient mice. Laboratory Investigation. 2001; 81:453-63.

[4] Vigen M, Ceccarelli J, Putnam A J. Protease-Sensitive P E G Hydrogels Regulate Vascularization In Vitro and In Vivo. Macromolecular Bioscience. 2014; 14:1368-79.

[5] Johnson J L H, Dolezal M C, Kerschen A, Matsunaga T O, Unger E C. \textitIn vitro comparison of dodecafluoropentane (DDFP), perfluorodecalin (PFD), and perfluoroctylbromide (PFOB) in the facilitation of oxygen exchange. Artificial cells, blood substitutes, and biotechnology. 2009; 37:156-62.

[6] Riess J G. Oxygen Carriers ("Blood Substitutes")—Raison d'Etre, Chemistry, and Some Physiology. Chemical Reviews. 2001; 101:2797-919.

[7] Dias A M A, Freire M, Coutinho J A P, Marrucho I M. Solubility of oxygen in liquid perfluorocarbons. Fluid Phase Equilibria. 2004; 222:325-30.

[8] Chin K, Khattak S F, Bhatia S R, Roberts S C. Hydrogel-perfluorocarbon composite scaffold promotes oxygen transport to immobilized cells. Biotechnology Progress. 2008; 24:358-66.

[9] Maillard E, Juszczak M T, Clark A, Hughes S J, Gray D R W, Johnson P R V. Perfluorodecalin-enriched fibrin matrix for human islet culture. Biomaterials. 2011; 32:9282-9.

[10] Chung Y I, Kim S K, Lee Y K, Park S J, Cho K O, Yuk S H, et al. Efficient revascularization by VEGF administration via heparin-functionalized nanoparticle-fibrin complex. Journal of Controlled Release. 2010; 143:282-9.

[11] Thomson K S, Dupras S K, Murry C E, Scatena M, Regnier M. Proangiogenic microtemplated fibrin scaffolds containing aprotinin promote improved wound healing responses. Angiogenesis. 2014; 17:195-205.

[12] Shea L D, Smiley E, Bonadio J, Mooney D J. DNA delivery from polymer matrices for tissue engineering. Nat Biotechnol. 1999; 17:551-4.

What is claimed is:

1. A method of achieving tissue expansion in a patient in need thereof, the method comprising:
injecting the patient with a biodegradable hydrogel scaffold comprising a perfluorocarbon (PFC) emulsion at a site in need of tissue expansion, wherein the PFC emulsion vaporizes from liquid droplets into gas bubbles in response to body heat in the absence of ultrasound, wherein the biodegradable hydrogel scaffold polymerizes to form a solid structure at the site, expands causing tissue expansion, and subsequently degrades in the patient,
wherein the scaffold is not exposed to ultrasound.

2. The method of claim 1, wherein the scaffold comprises a protein or polymer at a density is between about 100 µg/mL to about 100 mg/mL, optionally, wherein the protein is fibrinogen.

3. The method of claim 1, wherein the PFC emulsion contains perfluoropentane (PFP) as the dispersed phase, or the PFC emulsion contains perfluorohexane (PFH) as the dispersed phase.

4. The method of claim 1 wherein the PFC emulsion comprises a mixture of perfluorocarbons, wherein the mixture is 90% PFP:10% PFH, 95% PFP:5% PFH, 80% PFP:20% PFH, or 70% PFP:30% PFH.

5. The method of claim 1, wherein the patient in need of tissue expansion has undergone plastic surgery or the patient has undergone burn surgery.

6. The method of claim 1, wherein the patient in need of tissue expansion has undergone reconstruction of congenital or acquired defects of the scalp, face, ear, neck, trunk, breast, upper limb/extremity, or lower limb/extremity; or
the patient in need of tissue expansion has undergone skin reconstruction following removal of congenital nevus or hemangioma, breast reconstruction for defects resulting from mastectomy or lumpectomy, or tissue reconstruction following surgical resection; or
the patient in need of tissue expansion suffers from congenital anophthalmia or diabetes; or
the patient in need of tissue expansion suffers from facial or breast asymmetry; or
the patient in need of tissue expansion suffers from cleft lip, alveolus, or palate; or
the patient in need of tissue expansion has undergone reconstructive urology.

7. The method of claim 1, wherein the emulsion comprises a surfactant.

8. The method of claim 7, wherein the emulsion comprises a first surfactant which stabilizes a primary emulsion comprising a triblock copolymer, and the emulsion comprises a second surfactant which stabilizes a secondary emulsion comprising an aqueous soluble surfactant, optionally, wherein the triblock copolymer comprises a perfluoroether and polyethylene glycol.

9. The method of claim 8 wherein the aqueous soluble surfactant is selected from the group consisting of a protein, a lipid, an ionic copolymer and a non-ionic copolymer.

10. The method of claim 1, wherein initial pore size of the tissue scaffold is at least about 100 nanometers (nm).

11. The method of claim 1, wherein vaporization of the PFC droplet results in a final pore size of the tissue scaffold of at least about 40 µm and up to about 5 millimeters (mm).

12. The method of claim 2, wherein the scaffold comprises a protein at a density from about 100 µg/mL to about 10 mg/mL or from about 100 µg/mL to about 1 mg/mL.

13. The method of claim 1, wherein the biodegradable hydrogel scaffold degrades by cellular infiltration and enzymatic processes.

14. The method of claim 1, wherein the emulsion has a volume fraction in the scaffold that is about 1% to about 20%.

15. The method of claim 1, wherein the biodegradable hydrogel scaffold comprises one or more proteins.

16. The method of claim 1, wherein the PFC emulsion comprises a PFC having a boiling point lower than 37° C.

17. The method of claim 14, wherein the emulsion has a volume fraction of at least 10%.

18. The method of claim 1, wherein the site in need of tissue expansion is a site in the subcutaneous space of the patient and the tissue expansion is skin expansion.

19. The method of claim 18, wherein the skin expansion occurs for at least 8 days following the time of injecting the patient.

* * * * *